United States Patent
Ohyabu et al.

(10) Patent No.: US 10,233,156 B2
(45) Date of Patent: Mar. 19, 2019

(54) 9-MEMBERED FUSED RING DERIVATIVE

(71) Applicant: Shionogi & Co., Ltd., Osaka (JP)

(72) Inventors: Naoki Ohyabu, Osaka (JP); Kana Kurahashi, Osaka (JP); Yuji Nishiura, Osaka (JP); Manabu Katou, Osaka (JP); Keisuke Miyazaki, Osaka (JP); Yoshikazu Sasaki, Osaka (JP); Toshihiro Wada, Osaka (JP); Masafumi Iwatsu, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 15/557,992

(22) PCT Filed: Mar. 30, 2016

(86) PCT No.: PCT/JP2016/060395
§ 371 (c)(1),
(2) Date: Sep. 13, 2017

(87) PCT Pub. No.: WO2016/159082
PCT Pub. Date: Oct. 6, 2016

(65) Prior Publication Data
US 2018/0079727 A1    Mar. 22, 2018

(30) Foreign Application Priority Data
Mar. 30, 2015 (JP) ................. 2015-068500

(51) Int. Cl.
| C07D 235/04 | (2006.01) |
| C07D 263/56 | (2006.01) |
| C07D 235/26 | (2006.01) |
| C07D 403/12 | (2006.01) |
| A61K 31/4184 | (2006.01) |
| A61K 31/437 | (2006.01) |

(Continued)

(52) U.S. Cl.
CPC ........ *C07D 235/26* (2013.01); *A61K 31/4184* (2013.01); *A61K 31/437* (2013.01); *A61K 31/4439* (2013.01); *A61K 31/454* (2013.01); *A61K 31/506* (2013.01); *A61P 3/06* (2018.01); *A61P 3/08* (2018.01); *A61P 9/00* (2018.01); *C07D 235/28* (2013.01); *C07D 401/04* (2013.01); *C07D 401/12* (2013.01); *C07D 403/04* (2013.01); *C07D 403/12* (2013.01); *C07D 405/12* (2013.01); *C07D 471/04* (2013.01); *C07D 493/04* (2013.01)

(58) Field of Classification Search
CPC .......................... C07D 235/04; C07D 263/56
USPC ...................................................... 548/304.4
See application file for complete search history.

(56) References Cited

U.S. PATENT DOCUMENTS

2002/0156075 A1    10/2002    Childers et al.
2006/0178400 A1    8/2006    Beutel et al.
(Continued)

FOREIGN PATENT DOCUMENTS

JP    2016-79168    5/2016
WO    01/00612    1/2001
(Continued)

OTHER PUBLICATIONS

International Search Report dated Jun. 21, 2016 in International (PCT) Application No. PCT/JP2016/060395.
Clark et al., "Structure-activity relationships for a novel series of thiazolyl phenyl ether derivatives exhibiting potent and selective acetyl-CoA carboxylase 2 inhibitory activity", Bioorganic & Medicinal Chemistry Letters, vol. 16, 2006, pp. 6078-6081.
(Continued)

*Primary Examiner* — Niloofar Rahmani
(74) *Attorney, Agent, or Firm* — Wenderoth, Lind & Ponack, L.L.P.

(57) ABSTRACT

The purpose of the present invention is to provide novel compounds having ACC2 selective inhibitory activity. In addition, the present invention provides a pharmaceutical composition comprising the compound.
A compound of Formula:

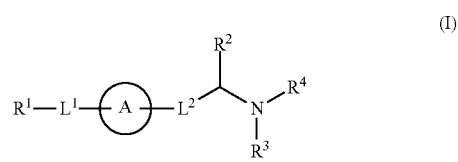

(I)

or its pharmaceutically acceptable salt,
wherein, $R^1$ is substituted or unsubstituted fused aromatic heterocyclyl represented by Formula:

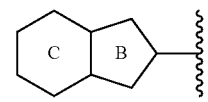

wherein,
ring B is 5-membered ring, ring C is 6-membered ring;
ring A is substituted or unsubstituted non-aromatic carbocycle or the like;
—$L^1$— is —O—$(CR^6R^7)$m— or the like;
—$L^2$— is —O—$(CR^6R^7)$n— or the like;
each $R^6$ is independently hydrogen or the like;
each $R^7$ is independently hydrogen or the like;
each m is independently an integer of 0, 1, 2 or 3;
each n is independently an integer of 1, 2 or 3;
$R^2$ is substituted or unsubstituted alkyl;
$R^3$ is hydrogen or substituted or unsubstituted alkyl;
$R^4$ is substituted or unsubstituted alkylcarbonyl or the like.

15 Claims, No Drawings

(51) Int. Cl.
*A61K 31/4439* (2006.01)
*A61K 31/454* (2006.01)
*A61K 31/506* (2006.01)
*C07D 401/04* (2006.01)
*C07D 401/12* (2006.01)
*C07D 235/28* (2006.01)
*C07D 403/04* (2006.01)
*C07D 405/12* (2006.01)
*C07D 471/04* (2006.01)
*C07D 493/04* (2006.01)
*A61P 3/06* (2006.01)
*A61P 3/08* (2006.01)
*A61P 9/00* (2006.01)

(56) References Cited

U.S. PATENT DOCUMENTS

| | | |
|---|---|---|
| 2012/0010247 A1 | 1/2012 | Kamata et al. |
| 2015/0246938 A1 | 9/2015 | Matsumura et al. |
| 2016/0257641 A1* | 9/2016 | Kobayashi ........... C07D 403/12 |

FOREIGN PATENT DOCUMENTS

| | | |
|---|---|---|
| WO | 01/00615 | 1/2001 |
| WO | 2007/095601 | 8/2007 |
| WO | 2007/095602 | 8/2007 |
| WO | 2007/095603 | 8/2007 |
| WO | 2008/079610 | 7/2008 |
| WO | 2010/000611 | 1/2010 |
| WO | 2010/000612 | 1/2010 |
| WO | 2010/000615 | 1/2010 |
| WO | 2010/003624 | 1/2010 |
| WO | 2010/111634 | 9/2010 |
| WO | 2011/009084 | 1/2011 |
| WO | 2011/136385 | 11/2011 |
| WO | 2012/074126 | 6/2012 |
| WO | 2012/173099 | 12/2012 |
| WO | 2013/142369 | 9/2013 |
| WO | 2014/061693 | 4/2014 |

OTHER PUBLICATIONS

Gu et al., "Synthesis and Structure-Activity Relationships of N-{3-[2-(4-Alkoxyphenoxy)thiazol-5-yl]-1-methylprop-2-ynyl}carboxy Derivatives as Selective Acetyl-CoA Carboxylase 2 Inhibitors", J. Med. Chem., vol. 49, 2006, pp. 3770-3773.

Xu et al., "The synthesis and structure—activity relationship studies of selective acetyl-CoA carboxylase inhibitors containing 4-(thiazol-5-yl) but-3-yn-2-amino motif: Polar region modifications", Bioorganic & Medicinal Chemistry Letters, vol. 17, 2007, pp. 1803-1807.

Clark et al., "Phenoxy thiazole derivatives as potent and selective acetyl-CoA carboxylase 2 inhibitors: Modulation of isozyme selectivity by incorporation of phenyl ring substituents", Bioorganic & Medicinal Chemistry Letters, vol. 17, 2007, pp. 1961-1965.

Gu et al., "N-{3-[2-(4-Alkoxyphenoxy)thiazol-5-yl]-1-methylprop-2-ynyl}carboxy Derivatives as Acetyl-CoA Carboxylase Inhibitors-Improvement of Cardiovascular and Neurological Liabilities via Structural Modifications", J. Med. Chem., vol. 50, 2007, pp. 1078-1082.

Haque et al., "Potent biphenyl- and 3-phenyl pyridine-based inhibitors of acetyl-CoA carboxylase", Bioorganic & Medicinal Chemistry Letters, vol. 19, 2009, pp. 5872-5876.

Keil et al., "Identification and Synthesis of Novel Inhibitors of Acetyl-CoA Carboxylase with in Vitro and in Vivo Efficacy on Fat Oxidation", J. Med. Chem., vol. 53, 2010, pp. 8679-8687.

Bhadauriya et al., "Identification of dual Acetyl-CoA carboxylases 1 and 2 inhibitors by pharmacophore based virtual screening and molecular docking approach", Mol. Divers, vol. 17, 2013, pp. 139-149.

International Preliminary Report on Patentability dated Oct. 12, 2017 in International Application No. PCT/JP2016/060395.

Extended European Search Report, dated Jul. 12, 2018 in corresponding European Patent Application No. 16772963.1.

* cited by examiner

9-MEMBERED FUSED RING DERIVATIVE

FIELD OF THE INVENTION

The present invention relates to a compound having an acetyl CoA carboxylase 2 (hereinafter referred to as ACC2) inhibitory activity.

BACKGROUND

Acetyl-CoA carboxylase (hereinafter referred to as ACC) is an enzyme that converts malonyl-CoA by carboxylation of acetyl-CoA. It is involved in the metabolism of fatty acids. The ACC has two isoforms called acetyl-CoA carboxylase 1 (hereinafter referred to as ACC1) and ACC2.

ACC2 is mainly expressed in heart and skeletal muscle, and malonyl-CoA produced by ACC2 inhibits the oxidation of fatty acids by inhibiting carnitine palmitoyl transferase I (CPT-I).

ACC2 deficient mice reduce the amount of malonyl-CoA in heart and skeletal muscle. As a result, fatty acids in the mice continuously are oxidized, and the mice lose their weight regardless of the increase in food intake. In addition, it is reported that ACC2 deficient mice develop tolerance to diabetes and obesity induced by the administration of high fatty/high carbohydrate food.

In view of the above information, ACC2 relates to disorders such as diabetes, obesity and the like. It is suggested that the inhibitor is expected as an anti-diabetes and anti-obesity drug.

On the other hand, since ACC1 deficient mice are fetal in fetal life, the drug inhibiting ACC2 selectively without inhibiting ACC1 is anticipated.

ACC2 inhibitors are disclosed in Patent Documents 1 to 7. For example, the following two compounds having oxymethylene structure are disclosed in Patent Document 1.

[Formula 1]

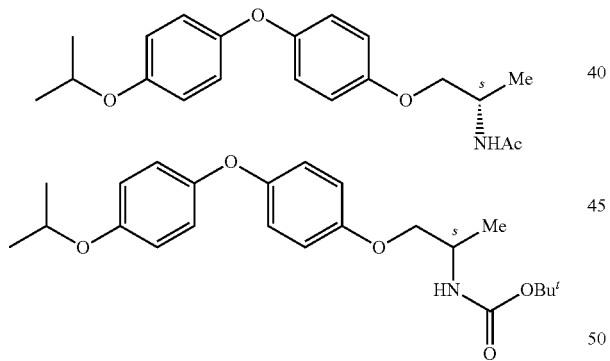

Ten compounds shown below having oxymethylene structure are disclosed in Patent Document 3.

[Formula 2]

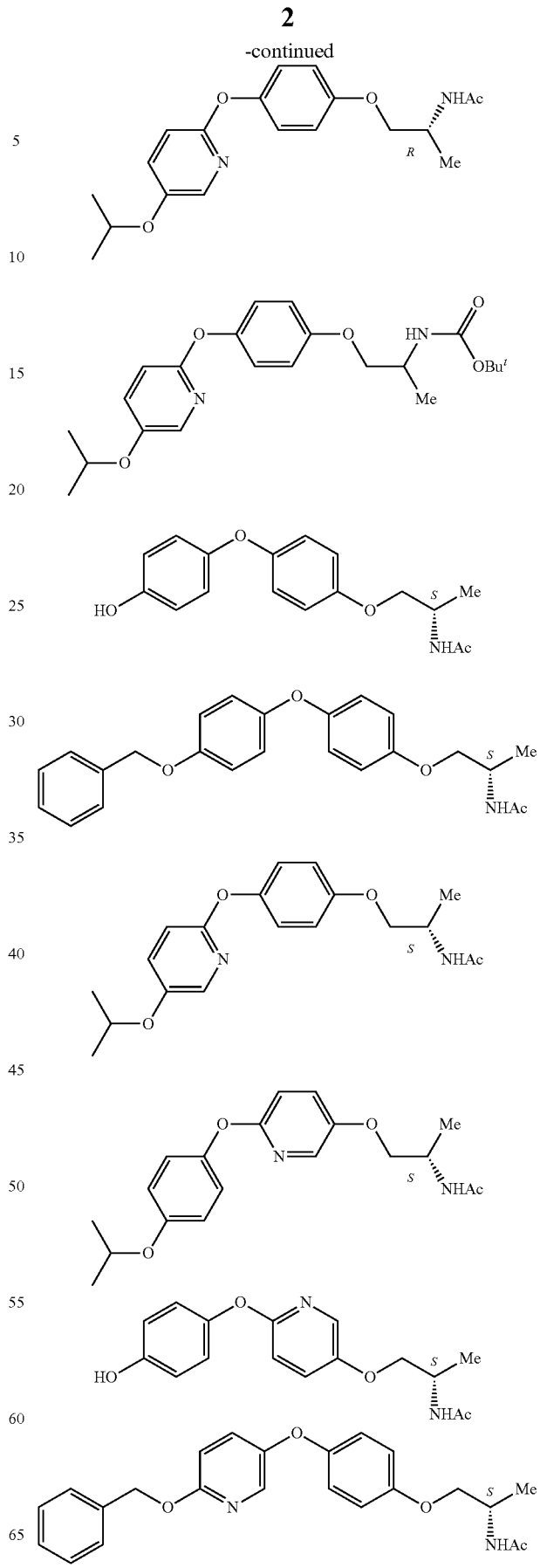

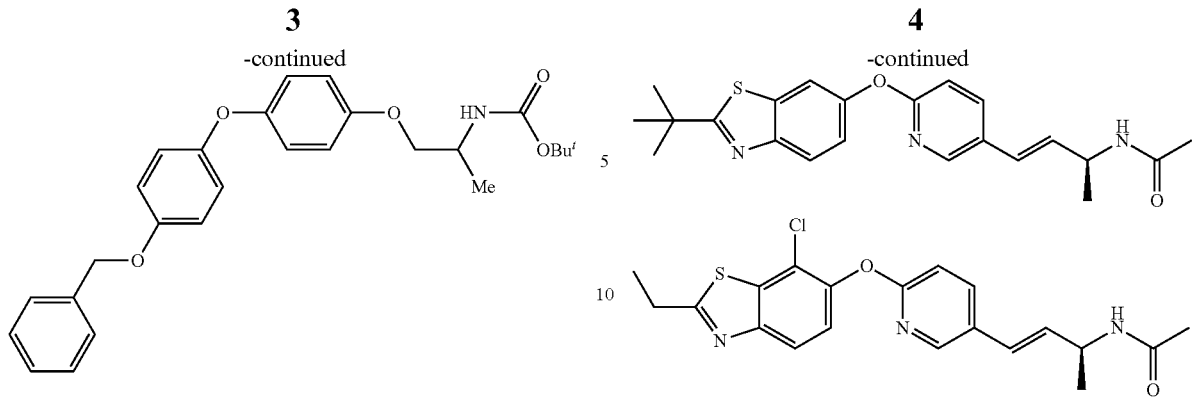

Although every these compounds has substituted or unsubstituted alkyloxy group at the para position of the terminal ring, there is no substituent at the ortho position.

The compound shown below is disclosed as a compound having olefinic structure in Patent Document 3.

[Formula 3]

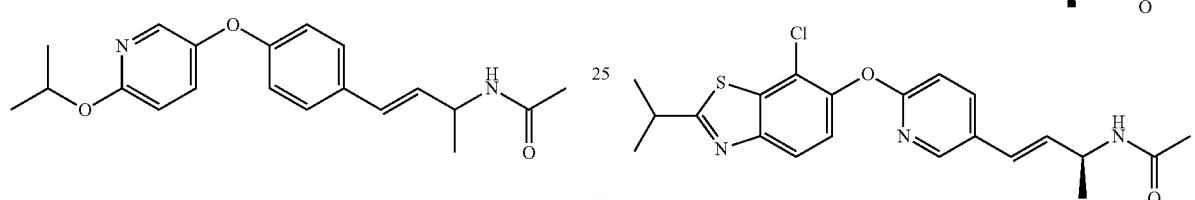

Thiazole phenyl ether derivatives specifically-inhibiting ACC2 are disclosed in non-Patent Documents 1 to 5. Biphenyl or 3-phenyl-pyridine derivatives exhibiting an ACC1 and ACC2 receptor inhibitory activity are disclosed in non-Patent Document 6. The compound shown below exhibiting an ACC2 receptor inhibitory activity and having preferable pharmacokinetic parameters is disclosed in non-Patent Document 7.

[Formula 4]

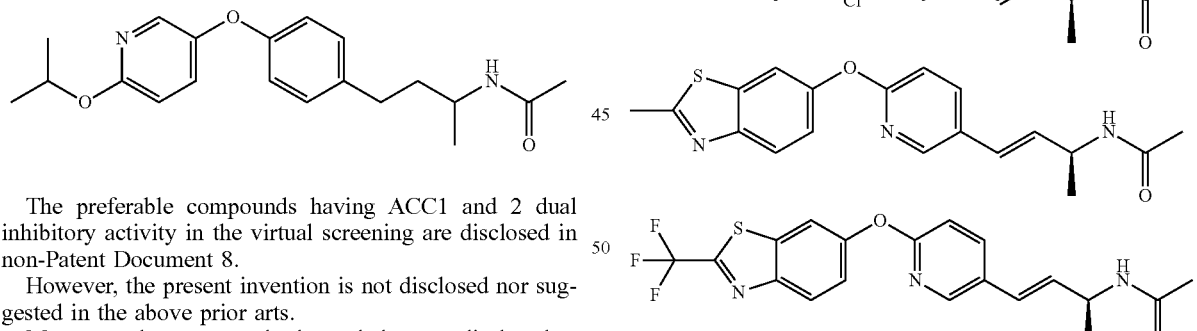

The preferable compounds having ACC1 and 2 dual inhibitory activity in the virtual screening are disclosed in non-Patent Document 8.

However, the present invention is not disclosed nor suggested in the above prior arts.

Moreover, the compounds shown below are disclosed as a compound having ACC2 receptor inhibitory activity in Patent Document 8.

[Formula 5]

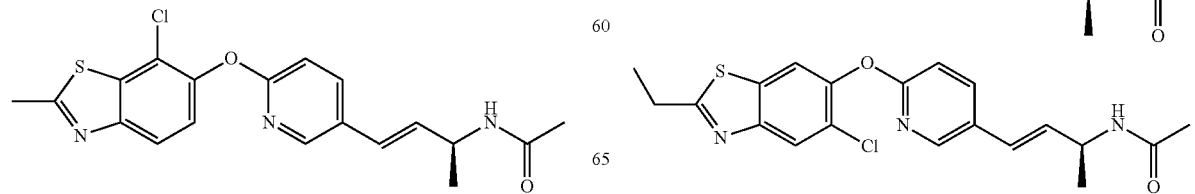

-continued
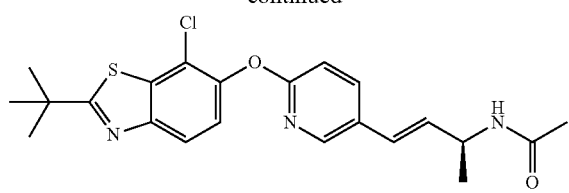
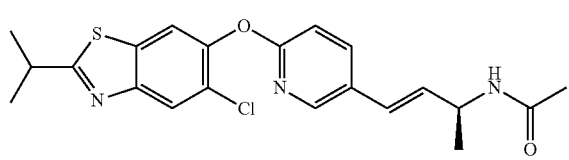
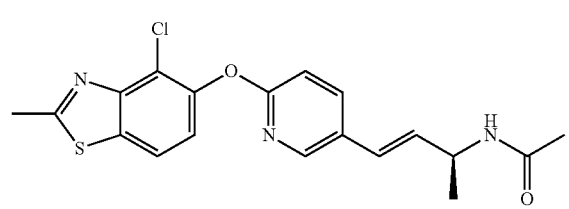
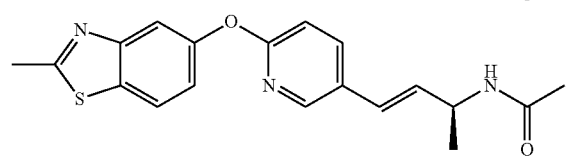
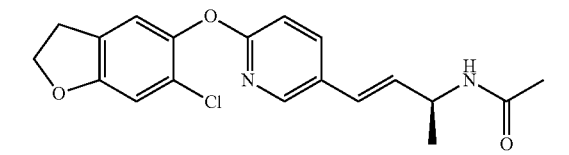
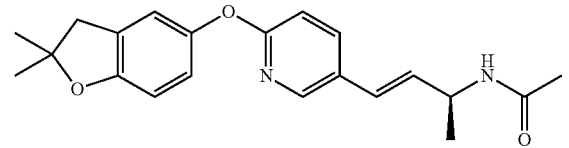
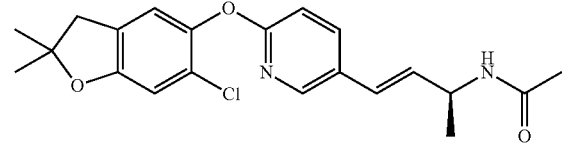
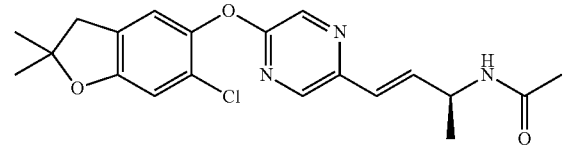
[Formula 6]
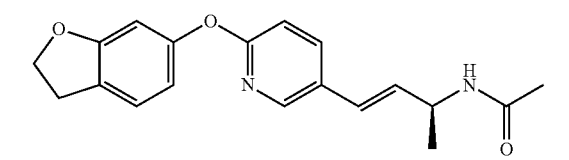
-continued
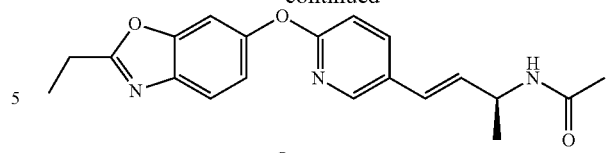
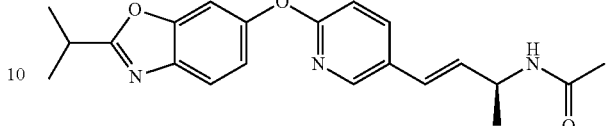
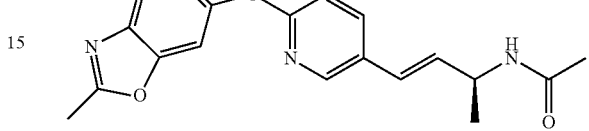
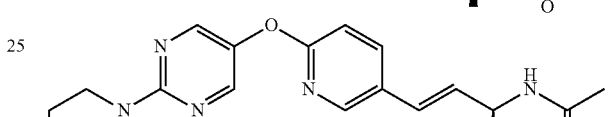
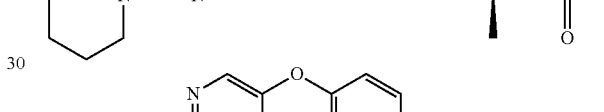
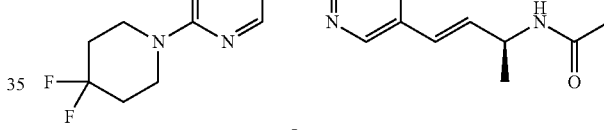
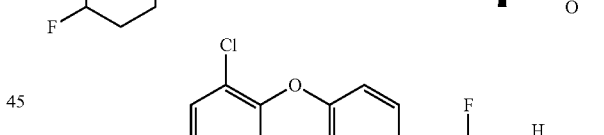
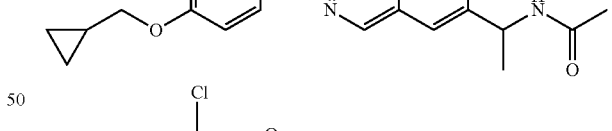
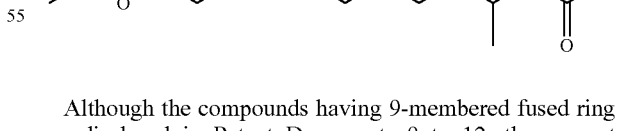
Although the compounds having 9-membered fused ring are disclosed in Patent Documents 9 to 12, the present invention is snot disclosed nor suggested in these prior arts.
PRIOR ART DOCUMENTS
Patent Documents
[Patent Document 1] WO2008/079610
[Patent Document 2] WO2010/050445

[Patent Document 3] WO2010/003624
[Patent Document 4] WO2007/095601
[Patent Document 5] WO2007/095602
[Patent Document 6] WO2007/095603
[Patent Document 7] US2006/178400
[Patent Document 8] WO2013/035827
[Patent Document 9] WO2013/142369
[Patent Document 10] WO2010/000615
[Patent Document 11] WO2010/000612
[Patent Document 12] WO2010/000611

Non-Patent Documents

[Non-patent Document 1] Bioorganic & Medicinal Chemistry Letters, (2006), Vol. 16, 6078-6081
[Non-patent Document 2] Journal of Medicinal Chemistry, (2006), Vol. 49, 3770-3773
[Non-patent Document 3] Bioorganic & Medicinal Chemistry Letters, (2007), Vol. 17, 1803-1807
[Non-patent Document 4] Bioorganic & Medicinal Chemistry Letters, (2007), Vol. 17, 1961-1965
[Non-patent Document 5] Journal of Medicinal Chemistry, (2007), Vol. 50, 1078-1082
[Non-patent Document 6] Bioorganic & Medicinal Chemistry Letters, (2009), Vol. 19, 5872-5876
[Non-patent Document 7] Journal of Medicinal Chemistry, (2010), Vol. 53, 8679-8687
[Non-patent Document 8] Molecular Diversity, (2013), Vol. 17, 139-149

DISCLOSURE OF INVENTION

Problems to be Solved by the Invention

The object of the present invention is to provide novel compounds having ACC2 selective inhibitory activity. In addition, the present invention provides a pharmaceutical composition comprising the compound.

Means for Solving the Problem

The present invention includes the followings.
(1) A compound of Formula (I):

[Formula 7]

$$R^1-L^1-\underset{}{\boxed{A}}-L^2-\underset{R^3}{\overset{R^2}{\underset{|}{C}}}-N\underset{}{\overset{R^4}{\diagdown}} \qquad (I)$$

or its pharmaceutically acceptable salt,
wherein
R$^1$ is substituted or unsubstituted fused aromatic heterocyclyl represented by Formula:

[Formula 8]

wherein
ring B is 5-membered ring, ring C is 6-membered ring;
ring A is substituted or unsubstituted non-aromatic carbocycle, substituted or unsubstituted non-aromatic heterocycle, substituted or unsubstituted aromatic carbocycle or substituted or unsubstituted aromatic heterocycle;
—L$^1$— is —O—(CR$^6$R$^7$)m—, —N(R$^8$)—(CR$^6$R$^7$)m— or —(CR$^6$R$^7$)m—, wherein the bond of left side is attached to R$^1$, the bond of right side is attached to ring A;
—L$^2$— is —O—(CR$^6$R$^7$)n—, —O—CR$^6$=CR$^7$—, —CR$^6$=CR$^7$— or —(CR$^6$R$^7$)n—, wherein the bond of left side is attached to ring A, the bond of right side is attached to the group represented by Formula:

[Formula 9]

$$\underset{}{\overset{R^2}{\underset{|}{\diagup}}}\underset{R^3}{\overset{}{\underset{|}{N}}}\diagdown R^4;$$

wherein
each R$^6$ is independently hydrogen, halogen, cyano, substituted or unsubstituted alkyl, substituted or unsubstituted alkenyl or substituted or unsubstituted alkynyl;
each R$^7$ is independently hydrogen, halogen, cyano, substituted or unsubstituted alkyl, substituted or unsubstituted alkenyl or substituted or unsubstituted alkynyl;
R$^6$ and R$^7$ on the same carbon atom may be taken together with the carbon atom to form ring;
R$^8$ is hydrogen or substituted or unsubstituted alkyl;
each m is independently an integer of 0, 1, 2 or 3;
each n is independently an integer of 1, 2 or 3;
R$^2$ is substituted or unsubstituted alkyl;
R$^3$ is hydrogen or substituted or unsubstituted alkyl;
R$^4$ is substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl, substituted or unsubstituted aromatic heterocyclylsulfonyl or substituted or unsubstituted sulfamoyl;
provided that the following compounds (i) and (ii) are excluded,
(i) the compounds wherein R$^1$ is benzimidazolyl or imidazopyridyl substituted with substituted or unsubstituted aromatic heterocyclylalkyl or substituted or unsubstituted non-aromatic heterocyclylalkyl; ring A is piperidine; —L$^1$— is —NH—; —L$^2$— is —CH$_2$—; and R$^4$ is tert-butyloxycarbonyl, and
(ii) the following compounds represented by Formula:

[Formula 10]
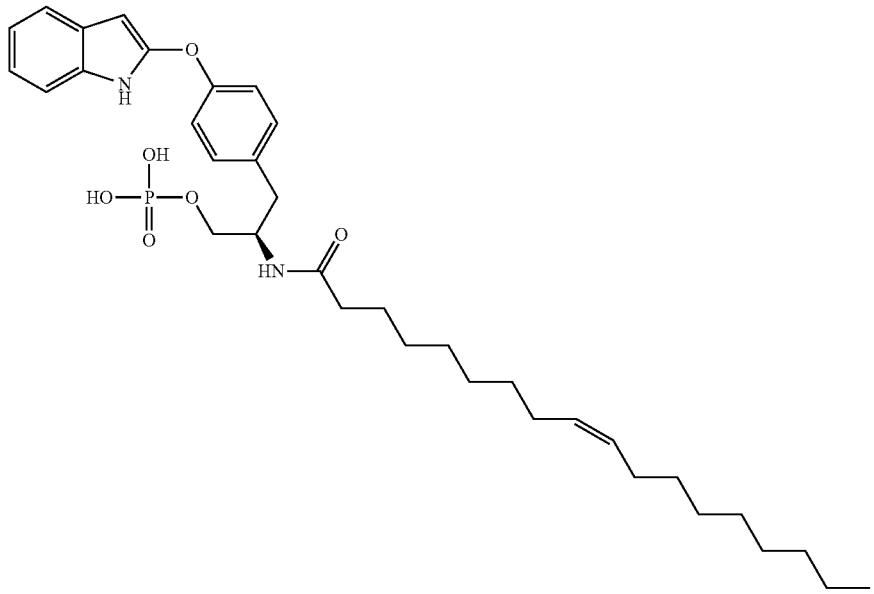
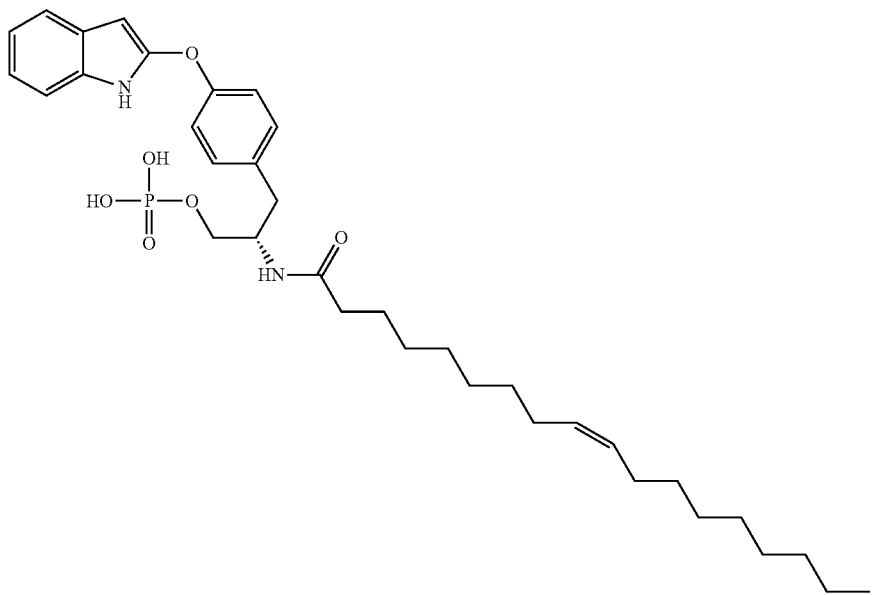
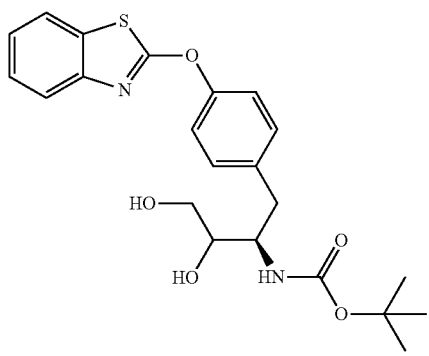

(2) The compound or its pharmaceutical acceptable salt according to the above (1), wherein $R^1$ is the group represented by Formula:

[Formula 11]

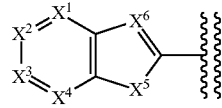

wherein
$X^1$ is N or $C(R^{x1})$;
$X^2$ is N or $C(R^{x2})$;
$X^3$ is N or $C(R^{x3})$;
$X^4$ is N or $C(R^{x4})$;
$X^5$ is $N(R^{x5})$, O or S;
$X^6$ is N or $C(R^{x6})$;
each $R^{x1}$, $R^{x2}$, $R^{x3}$, $R^{x4}$, $R^{x5}$ and $R^{x6}$ is independently hydrogen, halogen, hydroxy, carboxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted amino, substituted or unsubstituted carbamoyl, substituted or unsubstituted sulfamoyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted alkylsulfonyl, substituted or unsubstituted alkenylsulfonyl, substituted or unsubstituted alkynylsulfonyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted non-aromatic carbocyclylsulfonyl, substituted or unsubstituted aromatic carbocyclylsulfonyl, substituted or unsubstituted non-aromatic heterocyclylsulfonyl, substituted or unsubstituted aromatic heterocyclylsulfonyl, substituted or unsubstituted non-aromatic carbocyclyloxy, substituted or unsubstituted aromatic carbocyclyloxy, substituted or unsubstituted non-aromatic heterocyclyloxy, or substituted or unsubstituted aromatic heterocyclyloxy.

(3) The compound or its pharmaceutical acceptable salt according to the above (2), wherein $X^5$ is $N(R^{x5})$, and $X^6$ is N.

(4) The compound or its pharmaceutical acceptable salt according to the above (2), wherein $X^5$ is S, and $X^6$ is N.

(5) The compound or its pharmaceutical acceptable salt according to the above (2), wherein $R^1$ is the group represented by Formula:

[Formula 12]

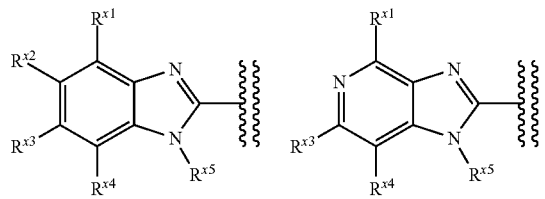 or

-continued

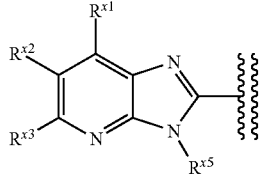

wherein the symbols are the same in the above (2).

(6) The compound or its pharmaceutical acceptable salt according to the above (2), wherein $R^1$ is the group represented by Formula:

[Formula 13]

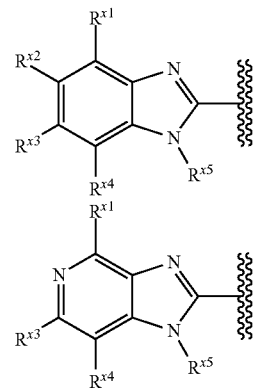

wherein the symbols are the same in the above (2).

(7) The compound or its pharmaceutical acceptable salt according to the above (5) or (6), wherein $R^{x1}$ is hydrogen, halogen or cyano; $R^{x2}$ is hydrogen, halogen or cyano; $R^{x3}$ is substituted or unsubstituted alkyloxy, substituted or unsubstituted non-aromatic carbocyclyloxy, substituted or unsubstituted aromatic carbocyclyloxy, substituted or unsubstituted non-aromatic heterocyclyloxy or substituted or unsubstituted aromatic heterocyclyloxy; $R^{x4}$ is hydrogen, halogen or cyano, and $R^{x5}$ is substituted or unsubstituted alkyl.

(8) The compound or its pharmaceutical acceptable salt according to any one of the above (1) to (7), wherein —$L^1$— is —O—$(CR^6R^7)m$—.

(9) The compound or its pharmaceutical acceptable salt according to any one of the above (1) to (7), wherein —$L^1$— is —$N(R^8)$—$(CR^6R^7)m$—.

(10) The compound or its pharmaceutical acceptable salt according to the above (8) or (9), wherein m is 0.

(11) The compound or its pharmaceutical acceptable salt according to any one of the above (1) to (10), wherein —$L^2$— is —O—$(CR^6R^7)n$— or —$(CR^6R^7)n$—.

(12) The compound or its pharmaceutical acceptable salt according to the above (11), wherein —$L^2$— is —O—$(CR^6R^7)n$—.

(13) The compound or its pharmaceutical acceptable salt according to any one of the above (1) to (12), wherein ring A is substituted or unsubstituted non-aromatic carbocycle or substituted or unsubstituted non-aromatic heterocycle.

(14) The compound or its pharmaceutical acceptable salt according to any one of the above (1) to (13), wherein the group represented by Formula: —$L^1$— ring A—$L^2$— is a group selected from the following formula:

[Formula 14]

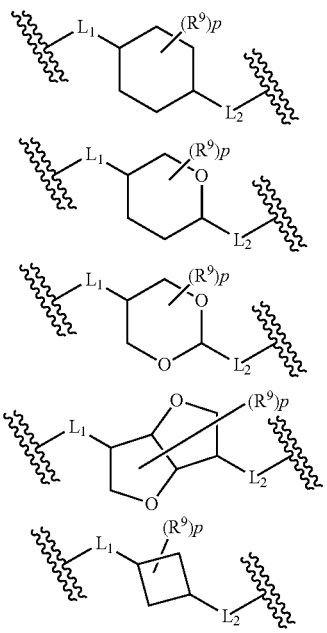

wherein

R⁹ is halogen, cyano, hydroxy, carboxy, oxo, substituted or unsubstituted alkyl, substituted or unsubstituted alkyloxy or substituted or unsubstituted amino;

p is an integer of 0 to 4.

(10') The compound or its pharmaceutical acceptable salt according to any one of the above (1) to (9), wherein —L¹— is —O—(CR⁶R⁷)m—.

(11') The compound or its pharmaceutical acceptable salt according to any one of the above (1) to (9), wherein —L¹— is —N(R⁸)—(CR⁶R⁷)m—.

(12') The compound or its pharmaceutical acceptable salt according to the above (10') or (11'), wherein m is 0.

(13') The compound or its pharmaceutical acceptable salt according to any one of the above (1) to (9) and (10') to (12'), wherein —L²— is a group of Formula: —O—(CR⁶R⁷)n—, wherein n is 1, or a group of Formula: —(CR⁶R⁷)n—.

(14') The compound or its pharmaceutical acceptable salt according to the above (1) to (9) and (10') to (12'), wherein —L²— is —(CR⁶R⁷)n— and n is 2.

(15) The compound or its pharmaceutical acceptable salt according to any one of the above (1) to (14) and (10') to (14'), wherein R⁴ is substituted or unsubstituted alkylcarbonyl, substituted or unsubstituted alkenylcarbonyl, substituted or unsubstituted alkyloxycarbonyl, substituted or unsubstituted carbamoyl, substituted or unsubstituted alkylsulfonyl or substituted or unsubstituted sulfamoyl.

(16) The compound or its pharmaceutical acceptable salt according to the above (15), wherein R⁴ is substituted or unsubstituted alkylcarbonyl.

(17) The compound or its pharmaceutical acceptable salt according to any one of the above (1) to (16) and (10') to (14'), wherein Formula (I) is Formula:

[Formula 15]

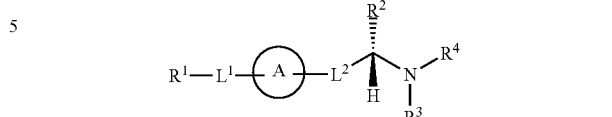

(I')

(18) The compound or its pharmaceutical acceptable salt according to any one of the above (1) to (17) and (10') to (14'), wherein Formula (I) is Formula:

[Formula 16]

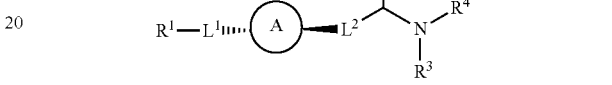

(I'')

(18') A compound of Formula (I):

[Formula 17]

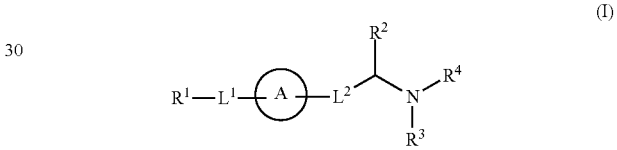

(I)

or its pharmaceutically acceptable salt,
wherein,
R¹ is a group represented by the formula:

[Formula 18]

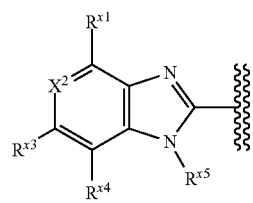

wherein X² is N or C(H),
R^{x1} is halogen,
R^{x3} is non-aromatic carbocyclyloxy,
R^{x4} is hydrogen,
R^{x5} is alkyl,
ring A is a group represented by the formula:

[Formula 19]

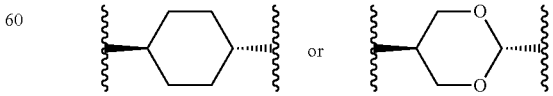

—L¹— is —O—,
—L²— is —O—(CH₂)— or —(CH₂)₂—, wherein, the left bond binds to ring A, the right bond binds to a group represented by the formula:

[Formula 20]

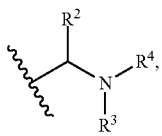

R² is alkyl or haloalkyl,
R³ is hydrogen,
R⁴ is alkylcarbonyl or carbamoyl,
provided that, the following compound is excluded

[Formula 21]

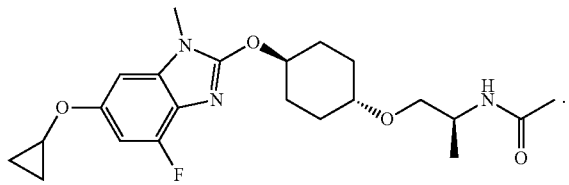

(19) The compound or its pharmaceutical acceptable salt according to the above (1), wherein the compound is selected from the group consisting of Examples I-200, I-201, I-205, I-219, I-221, I-222, I-231, I-234, I-237, I-243, and I-249.
(20) A pharmaceutical composition, which comprises a compound or its pharmaceutical acceptable salt according to any one of the above (1) to (19), (10') to (14') and (18').
(21) A pharmaceutical composition according to the above (20) for treatment or prevention of a disease associated with ACC2.
(22) A method for treatment or prevention of a disease associated with ACC2 characterized by administering the compound its pharmaceutical acceptable salt according to any one of the above (1) to (19), (10') to (14') and (18').
(23) Use of the compound or its pharmaceutical acceptable salt according to any one of the above (1) to (19), (10') to (14') and (18') for treatment or prevention of a disease associated with ACC2.
(24) The compound or its pharmaceutically acceptable salt according to any one of the above (1) to (19), (10') to (14') and (18') for treatment or prevention of a disease associated with ACC2.
(25) A pharmaceutical composition according to the above (20) having ACC2 inhibitory activity.

Effect of the Invention

The compound of this invention has ACC2 inhibitory activity. A pharmaceutical composition comprising the compound of this invention is very useful as a medicine for preventing or treating disease associated with ACC2, e.g. metabolic syndrome, obesity, diabetes, insulin resistance, abnormal glucose tolerance, diabetic peripheral neuropathy, diabetic nephropathy, diabetic retinal disease, diabetic macroangiopathy, hyperlipidemia, hypertension, cardiovascular illness, arterial sclerosis, atherosclerotic cardiovascular disease, cardiac arrest, cardiac infarction, infectious disease, neoplasm and the like (Journal of Cellular Biochemistry, (2006), vol. 99, 1476-1488, EXPERT OPINION ON THERAPEUTIC TARGETS, (2005), Vol. 9, 267-281, WO2005/108370, JP2009-196966, JP2010-081894, JP2009-502785).

MODE FOR CARRYING OUT THE INVENTION

Terms used in the present description are explained below. In this description, even when each term is used individually or used with other terms, the term has the same meaning.
"Halogen" includes fluorine atom, chlorine atom, bromine atom, and iodine atom. Especially preferred is fluorine atom, or chlorine atom.
"Alkyl" includes C1 to C15, preferably C1 to C10, more preferably C1 to C6, even more preferably C1 to C4 linear or branched alkyl group. Examples include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, n-decyl and the like.
A preferable embodiment of "alkyl" includes methyl, ethyl, n-propyl, isopropyl, n-butyl, isobutyl, sec-butyl, tert-butyl, n-pentyl and the like. More preferably is methyl, ethyl, n-propyl, isopropyl, tert-butyl and the like.
A preferable embodiment of "alkyl" of R² includes methyl and the like.
A preferable embodiment of "alkyl" of $R^{x1}$, $R^{x2}$, $R^{x3}$, $R^{x4}$, $R^{x5}$ and $R^{x6}$ includes methyl, ethyl, n-propyl, isopropyl, n-butyl, isobutyl, sec-butyl, tert-butyl and the like. More preferably is methyl, ethyl, n-propyl, isopropyl and the like.
A preferable embodiment of "alkyl" of $R^{x2}$ includes methyl, ethyl, n-propyl, isopropyl and the like.
A preferable embodiment of "alkyl" of $R^{x3}$ includes methyl, ethyl, n-propyl, isopropyl and the like.
A preferable embodiment of "alkyl" of $R^{x5}$ includes methyl, ethyl, n-propyl, isopropyl and the like.
"Alkyloxy" means the above "alkyl" bonded to the oxygen atom. Examples are methyloxy, ethyloxy, n-propyloxy, isopropyloxy, n-butyloxy, tert-butyloxy, isobutyloxy, sec-butyloxy, pentyloxy, isopentyloxy, hexyloxy and the like. A preferable embodiment of "alkyloxy" includes methyloxy, ethyloxy, n-propyloxy, isopropyloxy, tert-butyloxy and the like.
A preferable embodiment of "alkyloxy" of $R^{x1}$, $R^{x2}$, $R^{x3}$ and $R^{x4}$ includes methyloxy, ethyloxy, n-propyloxy, isopropyloxy, n-butyloxy, isobutyloxy, sec-butyloxy, tert-butyloxy and the like. More preferably is methyloxy, ethyloxy, n-propyloxy, isopropyloxy and the like.
A preferable embodiment of "alkyloxy" of $R^{x1}$ includes methyloxy, ethyloxy, n-propyloxy, isopropyloxy and the like.
A preferable embodiment of "alkyloxy" of $R^{x2}$ includes methyloxy, ethyloxy, n-propyloxy, isopropyloxy, isobutyloxy and the like.
A preferable embodiment of "alkyloxy" of $R^{x3}$ includes methyloxy, ethyloxy, n-propyloxy, isopropyloxy and the like.
A preferable embodiment of "alkyloxy" of $R^{x4}$ includes methyloxy, ethyloxy, n-propyloxy, isopropyloxy and the like.
"Alkyloxycarbonyl" means a carbonyl group to which the above "alkyloxy" is bonded. Examples are methyloxycarbonyl, ethyloxycarbonyl, propyloxycarbonyl, isopropyloxycarbonyl, tert-butyloxycarbonyl, isobutyloxycarbonyl, sec-butyloxycarbonyl, pentyloxycarbonyl, isopentyloxycarbonyl, hexyloxycarbonyl and the like. A more preferable embodiment of "alkyloxycarbonyl" includes methyloxycarbonyl, ethyloxycarbonyl, propyloxycarbonyl and the like.

Especially preferable embodiment of "alkyloxycarbonyl" of $R^4$ includes methyloxycarbonyl and the like.

"Alkenyl" includes linear or branched alkenyl containing one or more double bond at any position having C2 to C15, preferable C2 to C10, more preferably C2 to C6, even more preferably C2 to C4. Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, toridecenyl, tetradecenyl, pentadecenyl and the like.

A preferable embodiment of "alkenyl" includes vinyl, allyl, propenyl, isopropenyl, butenyl.

A preferable embodiment of "alkenyl" of $R^{x1}$, $R^{x2}$, $R^{x3}$, $R^{x4}$, $R^{x5}$ and $R^{x6}$ includes vinyl and the like.

A preferable embodiment of "alkenyl" of $R^{x2}$ includes vinyl.

A preferable embodiment of "alkenyl" of $R^{x3}$ includes vinyl.

"Alkynyl" includes linear or branched alkynyl containing one or more triple bond at any position having C2 to C10, preferably C2 to C8, more preferably C2 to C6, even more preferably C2 to C4. Examples include ethynyl, propynyl, buthynyl, pentynyl, hexynyl, heptynyl, octynyl, nonynyl, decynyl and the like. Alkynyl can have double bond(s) at any arbitrary position(s).

A preferable embodiment of "alkynyl" includes ethynyl, propynyl, butynyl, pentynyl and the like.

"Alkenyloxy" means the above "alkenyl" bonded to the oxygen atom. Examples include vinyloxy, allyloxy, 1-propenyloxy, 2-butenyloxy, 2-pentenyloxy, 2-hexenyloxy, 2-heptenyloxy, 2-octenyloxy and the like.

"Alkynyloxy" means the above "alkynyl" bonded to the oxygen atom. Examples include ethynyloxy, 1-propynyloxy, 2-propynyloxy, 2-butynyloxy, 2-pentynyloxy, 2-hexynyloxy, 2-heptynyloxy, 2-octynyloxy and the like.

"Alkylsulfanyl" means a sulfanyl group the hydrogen atom of which is replaced by the above "alkyl". Examples are methylsulfanyl, ethylsulfanyl, n-propylsulfanyl, isopropylsulfanyl, n-butylsulfanyl, tert-butylsulfanyl, isobutylsulfanyl, sec-butylsulfanyl, pentylsulfanyl, isopentylsulfanyl, hexylsulfanyl and the like. A preferable embodiment of "alkylsulfanyl" includes methylsulfanyl, ethylsulfanyl, n-propylsulfanyl, isopropylsulfanyl, tert-butylsulfanyl.

An embodiment of "alkylsulfanyl" of $R^{x1}$, $R^{x2}$, $R^{x3}$ and $R^{x4}$ includes methylsulfanyl, ethylsulfanyl, n-propylsulfanyl, isopropylsulfanyl and the like. A preferable embodiment includes methylsulfanyl and the like.

A preferable embodiment of "alkylsulfanyl" of $R^{x2}$ includes methylsulfanyl, ethylsulfanyl and the like.

A preferable embodiment of "alkylsulfanyl" of $R^{x3}$ includes methylsulfanyl, ethylsulfanyl, isobutylsulfanyl and the like.

"Alkenylsulfanyl" means a sulfanyl group the hydrogen atom of which is replaced by the above "alkenyl". Examples include vinylsulfanyl, allylsulfanyl, 1-propenylsulfanyl, 2-butenylsulfanyl, 2-pentenylsulfanyl, 2-hexenylsulfanyl, 2-heptenylsulfanyl, 2-octenylsulfanyl and the like.

"Alkynylsulfanyl" means a sulfanyl group the hydrogen atom of which is replaced by the above "alkynyl". Examples include ethynylsulfanyl, 1-propynylsulfanyl, 2-propynylsulfanyl, 2-butynylsulfanyl, 2-pentynylsulfanyl, 2-hexynylsulfanyl, 2-heptynylsulfanyl, 2-octynylsulfanyl and the like.

"Alkylcarbonyl" means a carbonyl group to which above "alkyl" is bonded. Examples include methylcarbonyl, ethylcarbonyl, propylcarbonyl, isopropylcarbonyl, tert-butylcarbonyl, isobutylcarbonyl, sec-butylcarbonyl, pentylcarbonyl, isopentylcarbonyl, hexylcarbonyl and the like. A preferable embodiment of "alkylcarbonyl" includes methylcarbonyl, ethylcarbonyl, n-propylcarbonyl and the like.

Especially preferable embodiment of "alkylcarbonyl" of $R^4$ includes methyl carbonyl and the like.

"Alkenylcarbonyl" means a carbonyl group to which above "alkenyl" is bonded. Examples include vinylcarbonyl, propenylcarbonyl and the like.

"Alkynylcarbonyl" means a carbonyl group to which above "alkynyl" is bonded. Examples include ethynylcarbonyl, propynylcarbonyl and the like.

"Cycloalkyl" means C3 to C8 cyclic saturated hydrocarbon group and the cyclic saturated hydrocarbon group fused with one or two 3- to 8-membered ring(s). Examples of C3 to C8 cyclic saturated carbocyclyl include cyclopropyl, cyclobutyl, cyclopentyl, cyclohexyl, cycloheptyl, cyclooctyl and the like. Especially preferable examples include C3 to C6 cycloalkyl, or C5 to C6 cycloalkyl. Furthermore, C3 cycloalkyl is preferable.

The 3- to 8-membered ring fused with C3 to C8 cyclic saturated hydrocarbons group includes cycloalkane ring (e.g.: cyclohexane ring, cyclopentane ring etc.), cycloalkene ring (e.g.: cyclohexene ring, cyclopentene ring etc.), non-aromatic heterocycle (e.g.: piperidine ring, piperazine ring, morpholine ring etc.). At the above ring, the bond(s) can be attached to C3 to C8 cyclic saturated hydrocarbon group.

For example, the following groups are also exemplified as a cycloalkyl, and included in cycloalkyl. These groups can be substituted at any arbitrary position(s). When cycloalkyl is substituted, the substituent(s) on the cycloalkyl can be substituted on either C3 to C8 cyclic saturated hydrocarbon group or 3- to 8-membered ring fused C3 to C8 cyclic saturated hydrocarbon group.

[Formula 22]

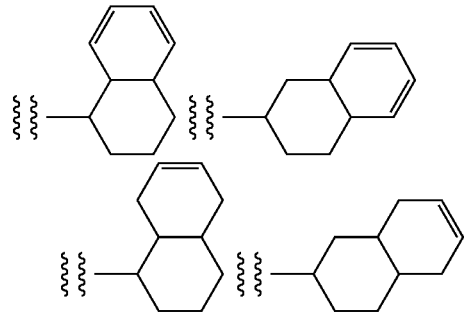

[Formula 23]

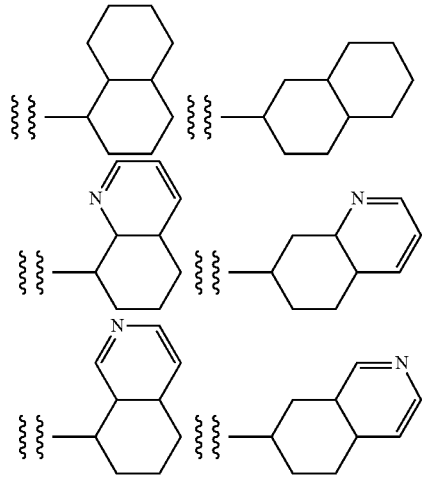

[Formula 24]

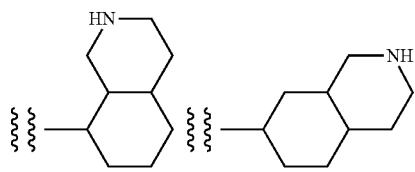

Furthermore, "cycloalkyl" includes a bridged group or a group to form spiro ring as follows.

[Formula 25]

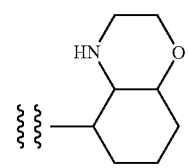

"Cycloalkyl substituted with carboxy" means the above "cycloalkyl" substituted with one or more carboxy.

"Cycloalkenyl" means C3 to C8 cyclic unsaturated aliphatic hydrocarbon group and the cyclic unsaturated aliphatic hydrocarbon group fused with one or two 3- or 8-membered cycle(s). "C3 to C8 cyclic unsaturated aliphatic hydrocarbon group" preferably means that C3 to C8 cyclic unsaturated aliphatic hydrocarbon group has 1 to 3 double bond(s) between carbon atom and carbon atom in the ring. Specifically, preferred is cyclopropenyl, cyclobutenyl, cyclopentenyl, cyclohexenyl, cycloheptenyl, cyclohexadienyl and the like. Especially preferred is C5 or C6 cycloalkenyl.

The ring fused with C3 to C8 cyclic unsaturated aliphatic hydrocarbon group includes carbocycle (aromatic carbocycle (e.g.: benzene ring, naphthalene ring etc.), cycloalkane ring (e.g.: cyclohexane ring, cyclopentane ring etc.), cycloalkene ring (e.g.: cyclohexene ring, cyclopentene ring etc.) and the like), heterocycle (aromatic heterocycle (pyridine ring, pyrimidine ring, pyrrole ring, imidazole ring etc.), non-aromatic heterocycle (e.g.: piperidine ring, piperazine ring, morpholine ring etc.)).

At the above ring, the bond(s) can be attached to C3 to C8 cyclic unsaturated aliphatic hydrocarbon group.

For example, the following groups are also exemplified as a cycloalkenyl and include in cycloalkenyl. These groups can be substituted at any arbitrary position(s). When cycloalkenyl is substituted, the substituent(s) on the cycloalkenyl can be substituted on either C3 to C8 cyclic unsaturated aliphatic hydrocarbon group or 3- to 8-membered ring fused C3 to C8 cyclic unsaturated aliphatic hydrocarbon group.

[Formula 26]

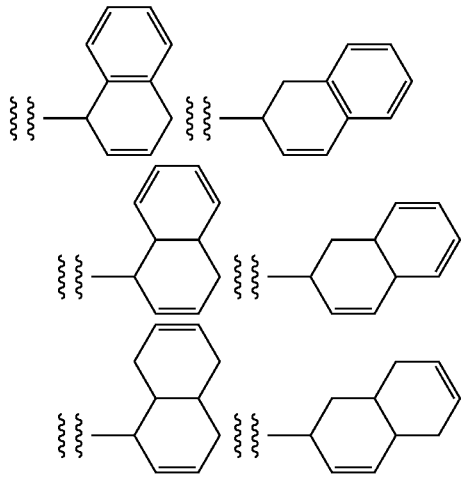

[Formula 27]

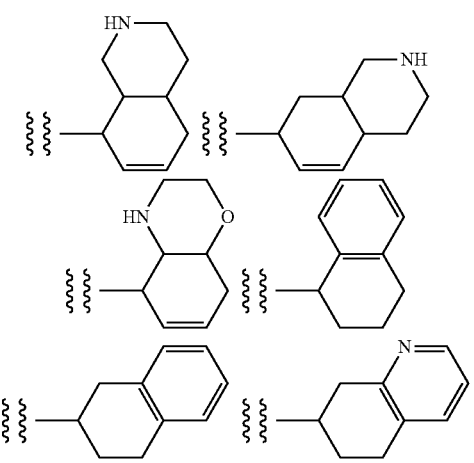

[Formula 28]

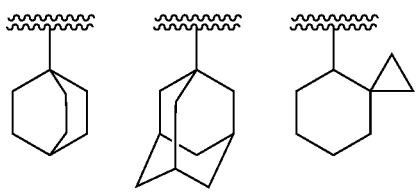

[Formula 29]

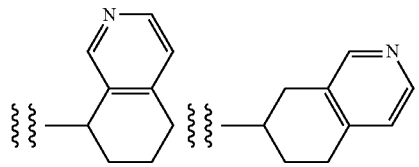

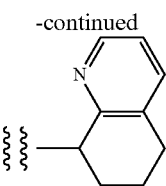

In addition, the "cycloalkenyl" also includes a group to form a spiro ring as follows:

[Formula 30]

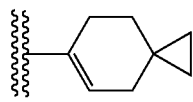

"Non-aromatic carbocyclyl" includes above "cycloalkyl" and "cycloalkenyl".

Examples of "non-aromatic carbocyclyl" of $R^{x1}$, $R^{x2}$, $R^{x3}$, $R^{x4}$, $R^{x5}$ and $R^{x6}$ include cyclopropyl, cyclobutyl, cyclopentyl, cyclohexyl and the like. Preferable examples include cyclopropyl, cyclobutyl and the like.

Examples of "non-aromatic carbocyclyl" of $R^{x1}$ include cycloalkyl. Preferable examples include cyclopropyl, cyclobutyl and the like.

Examples of "non-aromatic carbocyclyl" of $R^{x2}$ include cycloalkyl. Preferable examples include cyclopropyl, cyclobutyl and the like.

Examples of "non-aromatic carbocyclyl" of $R^{x3}$ include cycloalkyl. Preferable examples include cyclopropyl, cyclobutyl and the like.

Examples of "non-aromatic carbocyclyl" of $R^{x4}$ include cycloalkyl. Preferable examples include cyclopropyl, cyclobutyl and the like.

"Cycloalkane" means C3 to C8 cyclic saturated hydrocarbon and the cyclic saturated hydrocarbon fused with one or two 3- to 8-membered ring(s). Examples of C3 to C8 cyclic saturated hydrocarbon group include cyclopropane, cyclobutane, cyclopentane, cyclohexane, cycloheptane, cyclooctan. Especially, C3 to C6 cycloalkane is preferable.

For example, the ring fused with C3 to C8 cyclic saturated hydrocarbon group include cycloalkane ring (e.g.: cyclohexane ring, cyclopentane ring etc.), cycloalkene ring (e.g.: cyclohexene ring, cyclopentene ring etc.), non-aromatic heterocycle (e.g.: piperidine ring, piperazine ring, morpholine ring etc.).

"Cycloalkene" means C3 to C8 cyclic unsaturated aliphatic hydrocarbon and the cyclic unsaturated aliphatic hydrocarbon fused with one or two 3- to 8-membered ring(s). "C3 to C8 cyclic unsaturated aliphatic hydrocarbon" preferably means that C3 to C8 cyclic unsaturated aliphatic hydrocarbon has 1 to 3 double bond(s) between carbon atom and carbon atom in the ring. Specifically, preferred is cyclopropene, cyclobutene, cyclopentene, cyclohexene, cycloheptene, cyclohexadiene and the like. Especially, C5 or C6 cycloalkene is preferred.

The ring fused with C3 to C8 cyclic unsaturated aliphatic hydrocarbon includes carbocycle (aromatic carbocycle (e.g.: benzene ring, naphthalene ring etc.), cycloalkane ring (e.g.: cyclohexane ring, cyclopentane ring etc.), cycloalkene ring (e.g.: cyclohexene ring, cyclopentene ring etc.) and the like), heterocycle (aromatic heterocycle (pyridine ring, pyrimidine ring, pyrrole ring, imidazole ring etc.), non-aromatic heterocycle (e.g.: piperidine ring, piperazine ring, morpholine ring etc.)).

"Non-aromatic carbocycle" includes above "cycloalkane" and "cycloalkene". Specifically, preferred is cyclopropane, cyclobutane, cyclopentane, cyclohexane, cycloheptane, cyclooctane, cyclopropene, cyclobutene, cyclopentene, cyclohexene, cycloheptene, cyclohexadiene and the like.

Examples of "non-aromatic carbocycle" of ring A include cycloalkane and the like. Preferred is cyclobutane, cyclohexane and the like.

"Aromatic carbocyclyl" means monocyclic or polycyclic aromatic carbocyclyl and the monocyclic or polycyclic aromatic carbocyclyl fused with one or two 3- to 8-membered ring. Examples of "monocyclic or polycyclic aromatic carbocyclyl include phenyl, naphthyl, anthryl, phenanthryl. Especially phenyl is preferred.

The ring fused with monocyclic or polycyclic aromatic carbocyclyl includes non-aromatic carbocycle (e.g.: cycloalkane ring (e.g.: cyclohexane ring, cyclopentane ring etc.), cycloalkene ring (e.g.: cyclohexene ring, cyclopentene ring etc.) and the like), non-aromatic heterocycle (e.g.: piperidine ring, piperazine ring, morpholine ring etc.).

At the above ring, the bond(s) can be attached to monocyclic or polycyclic aromatic carbocycle.

For example, the following groups are also exemplified as an aromatic carbocyclyl and included in aromatic carbocyclyl. These groups can be substituted at any arbitrary position(s). When aromatic carbocyclyl is substituted, the substituent(s) on the aromatic carbocyclyl group can be substituted on either monocyclic or polycyclic aromatic carbocyclyl or 3- to 8-membered ring fused monocyclic or polycyclic aromatic carbocyclyl group.

[Formula 31]

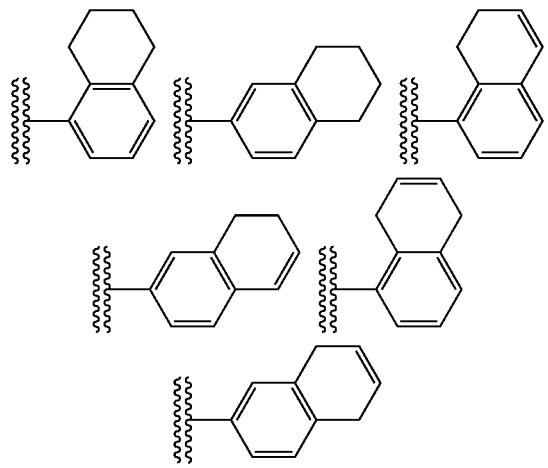

[Formula 32]

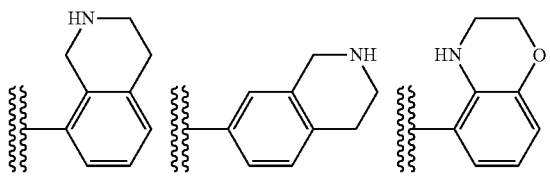

-continued

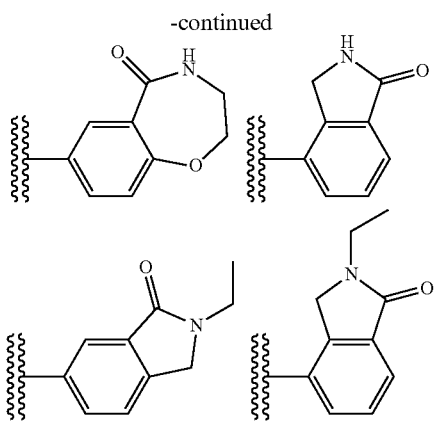

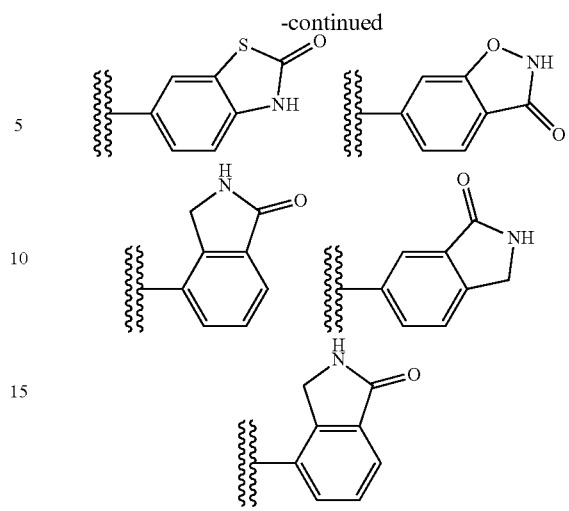

are exemplified.

Example of "6-membered aromatic carbocycle" includes benzene ring.

Example of "aromatic carbocyclyl" of $R^{x1}$ includes phenyl.

"Fused aromatic carbocyclyl" means polycyclic aromatic carbocyclyl, monocyclic or polycyclic aromatic carbocyclyl fused with one or two 3- to 8-membered ring. Examples of monocyclic or polycyclic aromatic carbocyclyl include phenyl, naphthyl, anthryl, phenanthryl. Especially, preferable example is phenyl.

"Substituted aromatic carbocyclyl" includes an aromatic carbocyclyl substituted with oxo. "Substituted fused aromatic carbocyclyl" include a fused aromatic carbocyclyl substituted with oxo. "Aromatic carbocyclyl substituted with oxo" and "fused aromatic carbocyclyl substituted with oxo" mean that two hydrogen atoms on 3- to 8-membered ring fused with monocyclic or polycyclic aromatic carbocyclyl constituting aromatic carbocyclyl are substituted with =O group.

As "aromatic carbocyclyl substituted with oxo" and "fused aromatic carbocyclyl substituted with oxo", the following formula:

[Formula 33]

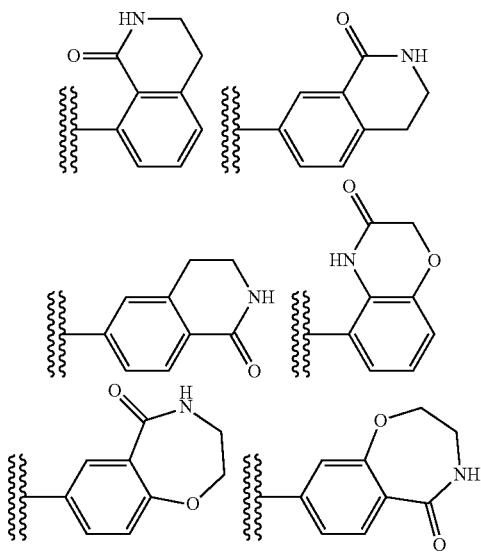

"Aromatic heterocyclyl" means monocyclic or polycyclic aromatic heterocyclyl containing one or more heteroatom(s) arbitrarily selected from O, S and N on the ring or the monocyclic or polycyclic aromatic heterocyclyl fused with one or two 3- to 8-membered ring(s), and includes "monocyclic aromatic heterocyclyl" and "fused aromatic heterocyclyl".

Especially preferable examples of "monocyclic aromatic heterocyclyl" are 5- or 6-membered aromatic heterocyclyl. Examples of "5-membered aromatic heterocyclyl" include pyrrolyl, imidazolyl, pyrazolyl, tetrazolyl, isooxazolyl, oxazolyl, oxadiazolyl, isothiazolyl, thiazolyl, thiadiazolyl, furyl, thienyl and the like. Examples of "6-membered aromatic heterocyclyl" include pyridyl, pyridazinyl, pyrimidinyl, pyrazinyl, triazoryl, triazinyl and the like.

Examples of the ring fused with monocyclic aromatic heterocyclyl include cycloalkane ring (e.g.: cyclohexane ring, cyclopentane ring etc.), cycloalkene ring (e.g.: cyclohexene ring, cyclopentene ring etc.), non-aromatic heterocycle (e.g.: piperidine ring, piperazine ring, morpholine ring etc.) and the like. At the above ring, the bond(s) can be attached to monocyclic or fused aromatic heterocyclyl containing one or more heteroatom(s) arbitrarily selected from O, S and N on the ring.

For example, the following groups are also exemplified as aromatic heterocyclyl and included in aromatic heterocyclyl. These groups can be substituted at any arbitrary position(s). When aromatic heterocyclyl is substituted, the substituent(s) on the aromatic heterocyclyl can be substituted on either monocyclic or fused aromatic heterocyclyl or 3- to 8-membered ring fused with monocyclic or fused aromatic heterocyclyl.

[Formula 34]

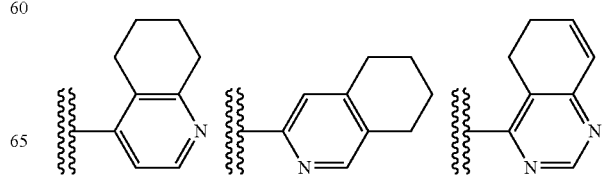

-continued

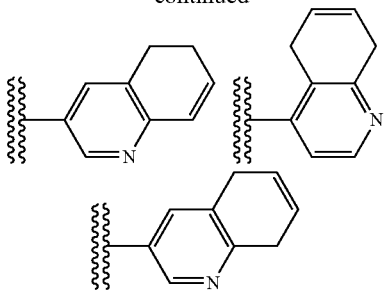

[Formula 35]

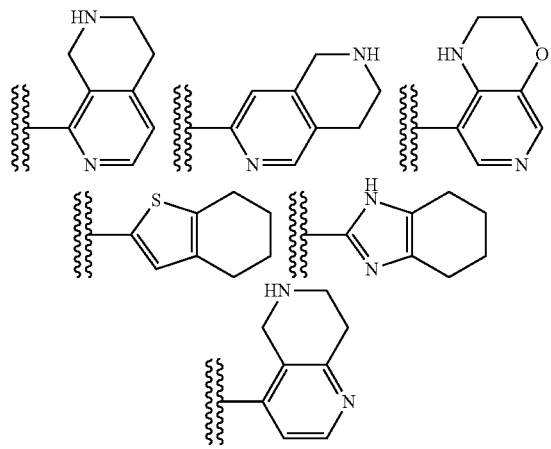

Substituted aromatic heterocyclyl includes aromatic heterocyclyl substituted with oxo. "Aromatic heterocyclyl substituted with oxo" means that two hydrogen atoms bonded to the carbon atom on 3- to 8-membered ring fused with monocyclic or polycyclic aromatic heterocycle constituting aromatic heterocyclyl are substituted with =O group.

As "aromatic heterocyclyl substituted with oxo" and "fused aromatic heterocyclyl substituted with oxo", the following formula:

[Formula 36]

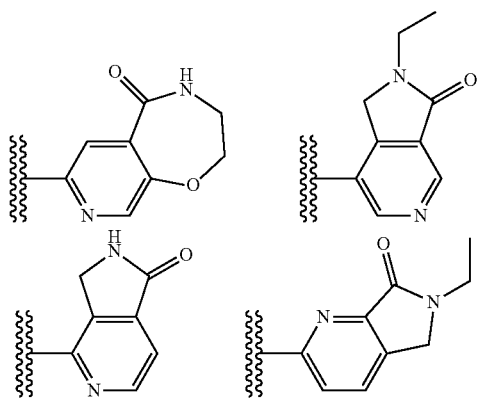

are exemplified.

Especially preferable examples of "fused aromatic heterocyclyl" are aromatic heterocyclyl fused with 5- or 6-membered ring. Examples include bicyclic aromatic heterocyclyl: e.g., indolyl, isoindolyl, indazolyl, indolizinyl, quinolinyl, isoquinolinyl, cinnolinyl, phthalazinyl, quinazolinyl, naphthylidinyl, quinoxalinyl, purinyl, pteridinyl, benzimidazolyl, benzisooxazolyl, benzoxazolyl, benzoxadiazoryl, benzisothiazolyl, benzothiazolyl, benzothiadiazolyl, benzofuryl, isobenzofuryl, benzothienyl, benzotriazoryl, imidazopyridyl, triazolopyridyl, imidazothiazolyl, pyrazinopyridazinyl, oxazolopyridyl, thiazolopyridyl and the like.

Examples of "fused aromatic heterocyclyl of $R^1$ include indolyl, isoindolyl, indazolyl, indolizinyl, benzimidazolyl, benzisooxazolyl, benzoxazolyl, benzoxadiazolyl, benzoisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, thiazolopyridyl and the like. Preferred is indolyl, benzimidazolyl, benzisooxazolyl, benzoxazolyl, benzoxadiazolyl, benzoisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyradinopyridazinyl, oxazolopyridyl, thiazolopyridyl and the like. Especially, preferable examples include benzimidazolyl, benzoxazolyl, benzthiazolyl, imidazopyridyl, imidazothiazolyl and the like. More preferable examples include benzimidazolyl, imidazopyridyl and the like.

Especially preferable embodiments of "fused aromatic heterocycyl" of $R^1$ include tetrobenzoxazepinyl, tetrahydroisoquinolyl, benzothiazolyl, dihydrobenzothiazolyl, dihydrobenzoisoxazolyl and the like.

"Non-aromatic heterocyclyl" means a monocyclic non-aromatic heterocyclyl containing one or more heteroatom(s) arbitrarily selected from O, S and N on the ring and the monocyclic non-aromatic heterocyclyl fused with one or two 3- to 8-membered ring(s) (polycyclic non-aromatic heterocyclyl groups).

Preferable examples of "monocyclic non-aromatic heterocyclyl" are a monocyclic 3- to 8-membered non-aromatic heterocyclyl group containing 1 to 4 heteroatom(s) arbitrarily selected from O, S and N on the ring. Specifically, dioxanyl, thiiranyl, oxiranyl, oxathiolanyl, azetidinyl, thianyl, pyrrolidinyl, pyrrolinyl, imidazolidinyl, imidazolinyl, pyrazolidinyl, pyrazolinyl, piperidyl, piperidino, piperazinyl, piperadino, morpholinyl, morpholino, oxadiazinyl, dihydropyridyl, thiomorpholinyl, thiomorpholino, tetrahydrofuryl, tetrahydropyranyl, tetrahydrothiazolyl, tetrahydroisothiazolyl, oxazolidyl, thiazolidyl, oxetanyl, thiazolidinyl, tetrahydropyridyl, dihydrothiazolyl, dihydrooxazinyl, hexahydroazepinyl, tetrahydrodiazepinyl, tetrahydropyridazinyl, hexahydropyrimidinyl, dioxolanyl, dioxazinyl, aziridinyl, dioxolinyl, oxepanyl, thiolanyl, thiazinyl, thiazinyl and the like are exemplified.

As a ring fused with monocyclic non-aromatic heterocyclyl containing one or more heteroatom(s) arbitrarily selected from O, S and N on the ring, for example, carbocycle (aromatic hydrocarbon ring (e.g.: benzene ring, naphthalene ring etc.), cycloalkane ring (e.g.: cyclohexane ring, cyclopentane ring etc.), cycloalkene ring (e.g.: cyclohexene ring, cyclopenten ring etc.) and the like), heterocycle (aromatic heterocycle (pyridine ring, pyrimidine ring, pyrrole ring, imidazole ring etc), non-aromatic heterocycle (e.g.: piperidine ring, piperazine ring, morpholine ring etc.) are exemplified.

As a polycyclic non-aromatic heterocyclyl, for example, indolinyl, isoindolinyl, chromanyl, isochromanyl and the like are exemplified.

When "non-aromatic heterocyclyl" is polycyclic non-aromatic heterocyclyl, the bond(s) can be attached to non-aromatic heterocyclyl containing one or more heteroatom(s) arbitrarily selected from O, S and N on the ring. For example, the following groups include also non-aromatic heterocyclyl. These groups can be substituted at any arbitrary position(s). When non-aromatic heterocyclyl is substituted, the substituent(s) on the non-aromatic heterocyclyl can be substituted on either monocyclic non-aromatic heterocyclyl containing one or more heteroatom(s) arbitrarily selected from O, S and N on the ring or 3- to 8-membered ring fused with monocyclic non-aromatic heterocyclyl group.

[Formula 37]

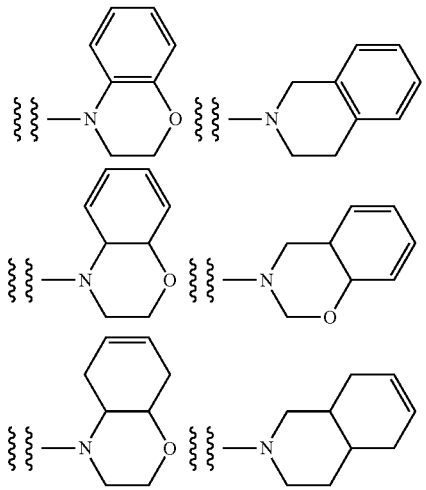

[Formula 38]

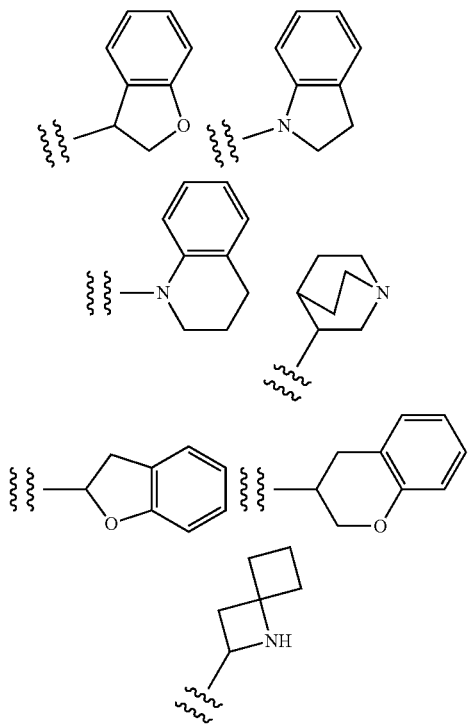

[Formula 39]

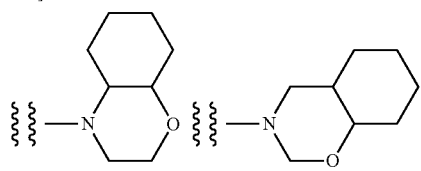

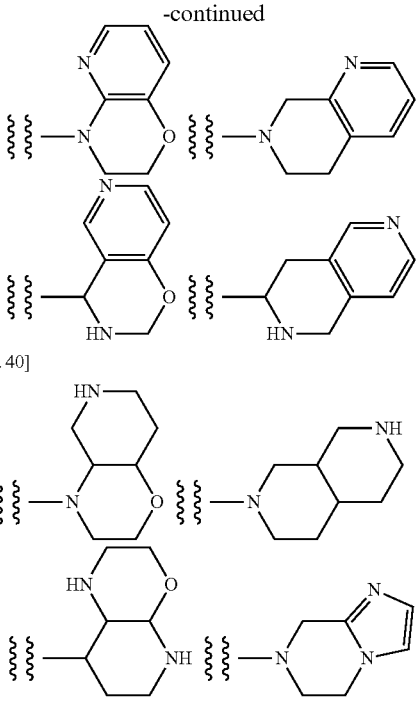

[Formula 40]

"Non-aromatic heterocyclyl" includes a ring having a bridge or a ring to form a spiro ring.

[Formula 41]

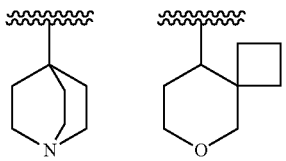

Examples of "non-aromatic heterocyclyl" of $R^{x3}$ include azetidinyl and the like.

"Non-aromatic heterocycle" means a monocyclic non-aromatic heterocycle containing one or more heteroatom(s) arbitrarily selected from O, S, and N on the ring, or the monocyclic non-aromatic heterocycle fused with one or two 3- to 8-membered ring(s) (polycyclic non-aromatic heterocycle).

Preferable examples of "monocyclic non-aromatic heterocycle" are monocyclic 3- to 8-membered non-aromatic heterocycle containing 1 to 4 heteroatom(s) arbitrarily selected from O, S and N on the ring. For example, dioxane, thiirane, oxyrane, oxathiolane, azetidine, thiane, pyrrolidine, pyrroline, imidazolidine, imidazoline, pyrazolidine, pyrazoline, piperidine, piperazine, morpholine, oxadiazine, dihydropyridine, thiomorpholine, tetrahydrofuran, tetrahydropyran, tetrahydrothiazole, tetrahydroisothiazole, oxazolidine, thiazolidine, oxetane, thiazolidine, tetrahydropyridine, dihydrothiazole, dihydrooxazine, hexahydroazepine, tetrahydrodiazepine, tetrahydropyridazine, hexahydropyrimidine, dioxolane, dioxazine, aziridine, dioxoline, oxepane, thiolane, thiazine and the like.

Examples of "non-aromatic heterocycle" of ring A include tetrahydrofuran, dioxolane. Preferred examples are tetrahydrofuran, 1, 3-dioxolane and the like.

Regarding the above "cycloalkyl", "cycloalkenyl", "non-aromatic carbocyclyl", "aromatic carbocyclyl", "aromatic heterocyclyl" and "non-aromatic heterocyclyl", "non-aromatic carbocycle", "non-aromatic heterocycle", "aromatic carbocycle", "aromatic heterocycle", "carbocycle" and "heterocycle" which are defined as "fused ring" mean as follows. When the ring is substituted, the ring may have the substitutent on the fused ring. "Non-aromatic carbocycle" and "non-aromatic heterocycle" may be substituted with oxo.

"Non-aromatic carbocycle" means C3 to C8 cyclic saturated hydrocarbon ring and C3 to C8 cyclic unsaturated aliphatic hydrocarbon ring. For example, cyclohexane ring, cyclopentane ring, cyclohexene ring, cyclopentene ring and the like are exemplified.

"Non-aromatic heterocycle" means 3- to 8-membered non-aromatic heterocycle containing one to four heteroatom(s) arbitrarily selected from O, S and N on the ring. For example, piperidine ring, piperazine ring, morpholine ring and the like are exemplified.

"Aromatic carbocycle" means monocyclic or polycyclic aromatic carbocycle. For example, benzene ring, naphthalene ring and the like are exemplified.

"Aromatic heterocycle" means monocyclic or polycyclic aromatic heterocycle containing one or more heteroatom(s) arbitrarily selected from O, S and N on the ring. For example, pyridine ring, pyrimidine ring, pyrrole ring, imidazole ring and the like are exemplified.

"Carbocycle" includes the above "non-aromatic carbocycle" and "aromatic carbocycle".

"Heterocycle" includes the above "non-aromatic heterocycle" and "aromatic heterocycle".

"Non-aromatic carbocyclyloxy" means the above "non-aromatic carbocyclyl" bonded to an oxygen atom. For example, cyclopropyloxy, cyclohexyloxy, cyclohexenyloxy, cyclopropenyloxy, cyclobutenyloxy, cyclopentenyloxy, cyclohexenyloxy, cycloheptenyloxy, cyclohexadienyloxy and the like are exemplified.

Examples of "non-aromatic carbocyclyloxy" of $R^{x3}$ include cycloalkyloxy. Preferred are cyclopropyloxy, cyclobutyloxy and the like.

"Aromatic carbocyclyloxy" means the above "aromatic carbocyclyl" bonded to an oxygen atom. For example, phenyloxy, naphthyloxy and the like are exemplified.

"Aromatic heterocyclyloxy" means the above "aromatic heterocyclyl" bonded to an oxygen atom. For example, pyridyloxy, oxazolyloxy and the like are exemplified.

Examples of "aromatic heterocyclyloxy" of $R^{x3}$ include pyrimidiloxy.

"Non-aromatic heterocyclyloxy" means the above "non-aromatic heterocyclyl" bonded to an oxygen atom. For example, piperidinyloxy, tetrahydro furyloxy and the like are exemplified.

Examples of "non-aromatic heterocyclyloxy" of $R^{x3}$ include oxetanyloxy and the like.

"Non-aromatic carbocyclylcarbonyl" means the above "cycloalkyl" or "cycloalkenyl" bonded to a carbonyl group. For example, cyclopropylcarbonyl, cyclohexylcarbonyl, cyclohexenylcarbonyl, cyclohexenylcarbonyl and the like are exemplified.

"Aromatic carbocyclylcarbonyl" means the above "aromatic carbocyclyl" bonded to a carbonyl group. For example, phenylcarbonyl, naphthylcarbonyl and the like are exemplified.

"Aromatic heterocyclylcarbonyl" means the above "aromatic heterocyclyl" bonded to a carbonyl group. For example, pyridylcarbonyl, pyrazolylcarbonyl, oxazolylcarbonyl, isoxazolylcarbonyl, furylcarbonyl and the like are exemplified.

Examples of "aromatic heterocyclylcarbonyl" of $R^4$ include pyrazolylcarbonyl and the like.

"Non-aromatic heterocyclylcarbonyl" means the above "non-aromatic heterocyclyl" bonded to a carbonyl group. For example, oxetanylcarbonyl, piperidinylcarbonyl, tetrahydrofurylcarbonyl and the like are exemplified.

"Alkylsulfonyl" means the above "alkyl" bonded to a sulfonyl group. For example, methylsulfonyl, ethylsulfonyl, propylsulfonyl, isopropylsulfonyl, tert-butylsulfonyl, isobutylsulfonyl, sec-butylsulfonyl and the like are exemplified.

A preferable embodiment of "alkylsulfonyl" includes methylsulfonyl, ethylsulfonyl.

Examples of "alkylsulfonyl" of $R^{x3}$ include isobutylsulfonyl and the like are exemplified.

Examples of "alkylsulfonyl" of $R^4$ include methylsulfonyl and the like.

"Alkenylsulfonyl" means the above "alkenyl" bonded to a sulfonyl group. For example, ethylenylsulfonyl, propenylsulfonyl and the like are exemplified.

"Alkynylsulfonyl" means the above "alkynyl" bonded to a sulfonyl group. For example, ethynylsulfonyl, propynylsulfonyl and the like are exemplified.

"Non-aromatic carbocyclylsulfonyl" means the above "non-aromatic carbocyclyl" bonded to a sulfonyl group. For example, cyclopropylsulfonyl, cyclopentanylsulfonyl, cyclohexylsulfonyl, cyclopropenylsulfonyl, cyclopentenylsulfonyl, cyclohexenylsulfonyl and the like are exemplified.

"Aromatic carbocyclylsulfonyl" means the above "aromatic carbocyclyl" bonded to a sulfonyl group. For example, phenylsulfonyl, naphthylsulfonyl and the like are exemplified.

"Aromatic heterocyclylsulfonyl" means the above "aromatic heterocyclyl" bonded to a sulfonyl group. For example, pyridylsulfonyl, oxazolylsulfonyl and the like are exemplified.

"Non-aromatic heterocyclylsulfonyl" means the above "non-aromatic heterocyclyl" bonded to a sulfonyl group. For example, piperidinylsulfonyl, tetrahydrofurylsulfonyl and the like are exemplified.

"Alkenyloxycarbonyl" means the above "alkenyloxy" bonded to a carbonyl group. For example, ethylenyloxycarbonyl, propenyloxycarbonyl and the like are exemplified.

"Alkynyloxycarbonyl" means the above "alkynyloxy" bonded to a carbonyl group. For example, ethynyloxycarbonyl, propynyloxycarbonyl and the like are exemplified.

"Aromatic carbocyclyloxycarbonyl" means the above "aromatic carbocyclyloxy" bonded to a carbonyl group. For example, phenyloxycarbonyl, naphthyloxycarbonyl and the like are exemplified.

"Non-aromatic carbocyclyloxycarbonyl" means the above "non-aromatic carbocyclyloxy" bonded to a carbonyl group. For example, cyclopropylox carbonyl, cyclohexylox carbonyl, cyclohexenylox carbonyl, cyclopropenylox carbonyl and the like are exemplified.

"Aromatic heterocyclyloxycarbonyl" means the above "aromatic heterocyclyloxy" bonded to a carbonyl group. For example, pyridyloxycarbonyl, oxazolyloxycarbonyl and the like are exemplified.

"Non-aromatic heterocyclyloxycarbonyl" means the above "non-aromatic heterocyclyloxy" bonded to a carbonyl group. For example, piperidinyloxycarbonyl, tetrahydrofuryloxycarbonyl and the like are exemplified.

"Non-aromatic carbocyclylsulfanyl" means a sulfanyl group the hydrogen atom of which is replaced by the above "non-aromatic carbocyclyl". For example, cyclopropylsulfanyl, cyclohexylsulfanyl, cyclohexenylsulfanyl, cyclopropenylsulfanyl, cyclobutenylsulfanyl, cyclopentenylsulfanyl, cycloheptenylsulfanyl, cyclohexadienylsulfanyl and the like are exemplified.

"Aromatic carbocyclylsulfanyl" means a sulfanyl group the hydrogen atom of which is replace by the above "aromatic carbocyclyl". For example, phenylsulfanyl, naphthylsulfanyl and the like are exemplified.

"Aromatic heterocyclylsulfanyl" means a sulfanyl group the hydrogen atom of which is replaced by the above "aromatic heterocyclyl". For example, pyridylsulfanyl, oxazolylsulfanyl and the like are exemplified.

"Non-aromatic heterocyclylsulfanyl" means a sulfanyl group the hydrogen atom of which is replaced by the above "non-aromatic heterocyclyl". For example, piperidinylsulfanyl, tetrahydrofurylsulfanyl and the like are exemplified.

"Alkylsulfinyl" means the above "alkyl" bonded to a sulfinyl group. For example, methylsulfinyl, ethylsulfinyl, n-propylsulfinyl, isopropylsulfinyl and the like are exemplified.

"Alkenylsulfinyl" means the above "alkenyl" bonded to a sulfinyl group. For example, ethylenylsulfinyl, propenylsulfinyl and the like are exemplified.

"Alkynylsulfinyl" means the above "alkynyl" bonded to a sulfinyl group. For example, ethynylsulfinyl, propynylsulfinyl and the like are exemplified.

"Non-aromatic carbocyclylsulfinyl" means the above "non-aromatic carbocyclyl" bonded to a sulfinyl group. For example, cyclopropylsulfinyl, cyclohexylsulfinyl, cyclohexenylsulfinyl, cyclopropenylsulfinyl, cyclobutenylsulfinyl, cyclopentenylsulfinyl, cycloheptenylsulfinyl, cyclohexadienylsulfinyl and the like are exemplified.

"Aromatic carbocyclylsulfinyl" means the above "aromatic carbocyclyl" bonded to a sulfinyl group. For example, phenylsulfinyl, naphthylsulfinyl and the like are exemplified.

"Aromatic heterocyclyl sulfinyl" means the above "aromatic heterocyclyl" bonded to a sulfinyl group. For example, pyridylsulfinyl, oxazolylsulfinyl and the like are exemplified.

"Non-aromatic heterocyclyl sulfinyl" means the above "non-aromatic heterocyclyl" bonded to a sulfinyl group. For example, piperidinylsulfinyl, tetrahydrofurylsulfinyl and the like are exemplified.

"Aminosulfinyl" means an amino group bonded to a sulfinyl group.

"Alkylsulfonyloxy" means the above "alkylsulfonyl" bonded to an oxygen atom. For example, methylsulfonyloxy, ethylsulfonyloxy, propylsulfonyloxy, isopropylsulfonyloxy, tert-butylsulfonyloxy, isobutylsulfonyloxy, sec-butylsulfonyloxy and the like are exemplified.

A preferable embodiment of "alkylsulfonyloxy" includes methylsulfonyloxy, ethylsulfonyloxy and the like.

"Alkenylsulfonyloxy" means the above "alkenylsulfonyl" bonded to an oxygen atom. For example, ethylenylsulfonyloxy, propenylsulfonyloxy and the like are exemplified.

"Alkynylsulfonyloxy" means the above "alkynylsulfonyl" bonded to an oxygen atom. For example, ethynylsulfonyloxy, propynylsulfonyloxy and the like are exemplified.

"Non-aromatic carbocyclylsulfonyloxy" means the above "non-aromatic carbocyclylsulfonyl" bonded to an oxygen atom. For example, cyclopropylsulfonyloxy, cyclohexylsulfonyloxy, cyclohexenylsulfonyloxy, cyclopropenylsulfonyloxy and the like are exemplified.

"Aromatic carbocyclylsulfonyloxy" means the above "aromatic carbocyclylsulfonyl" bonded to an oxygen atom. For example, phenylsulfonyloxy, naphthylsulfonyloxy and the like are exemplified.

"Aromatic heterocyclylsulfonyloxy" means the above "aromatic heterocyclylsulfonyl" bonded to an oxygen atom. For example, pyridylsulfonyloxy, oxazolylsulfonyloxy and the like are exemplified.

"Non-aromatic heterocyclylsulfonyloxy" means the above "non-aromatic heterocyclylsulfonyl" bonded to an oxygen atom. For example, piperidinylsulfonyloxy, tetrahydrofurylsulfonyloxy and the like are exemplified.

"Alkylcarbonyloxy" means the above "alkylcarbonyl" bonded to an oxygen atom. Examples of "alkyl carbonyloxy" include methylcarbonyloxy, ethylcarbonyloxy, propylcarbonyloxy, isopropylcarbonyloxy, tert-butylcarbonyloxy, isobutylcarbonyloxy, sec-butylcarbonyloxy and the like.

A preferable embodiment of "alkylcarbonyloxy" includes methylcarbonyloxy, ethylcarbonyloxy and the like.

"Alkenylcarbonyloxy" means the above "alkenylcarbonyl" bonded to an oxygen atom. For example, ethylenylcarbonyloxy, propenylcarbonyloxy and the like are exemplified.

"Alkynylcarbonyloxy" means the above "alkynylcarbonyl" bonded to an oxygen atom. For example, ethynylcarbonyloxy, propynylcarbonyloxy and the like are exemplified.

"Non-aromatic carbocyclylcarbonyloxy" means the above "non-aromatic carbocyclylcarbonyl" bonded to an oxygen atom. Examples of "cycloalkylcarbonyloxy" include cyclopropylcarbonyloxy, cyclohexylcarbonyloxy, cyclohexenylcarbonyloxy and the like.

"Aromatic carbocyclylcarbonyloxy" means the above "aromatic carbocyclylcarbonyl" bonded to an oxygen atom. Examples of "aromatic carbocyclylcarbonyloxy" include phenylcarbonyloxy, naphthylcarbonyloxy and the like.

"Aromatic heterocyclylcarbonyloxy" means the above "aromatic heterocyclylcarbonyl" bonded to an oxygen atom. Example of "aromatic heterocyclylcarbonyloxy" include pyridylcarbonyloxy, oxazolylcarbonyloxy and the like are exemplified.

"Non-aromatic heterocyclylcarbonyloxy" means the above "non-aromatic heterocyclylcarbonyl" bonded to an oxygen atom. Examples of "non-aromatic heterocyclylcarbonyloxy" include piperidinylcarbonyloxy, tetrahydrofurylcarbonyloxy and the like are exemplified.

"Alkyloxycarbonyl" means the above "alkyloxy" bonded to a carbonyl group. Examples of "alkyloxycarbonyl" include methyloxycarbonyl, ethyloxycarbonyl, propyloxycarbonyl, isopropyloxycarbonyl, tert-butyloxycarbonyl, isobutyloxycarbonyl, sec-butyloxycarbonyl, pentyloxycarbonyl, isopentyloxycarbonyl, hexyloxycarbonyl and the like are exemplified. A preferable embodiment of "alkyloxycarbonyl" includes methyloxycarbonyl, ethyloxycarbonyl, propyloxycarbonyl and the like.

"Alkenyloxycarbonyl" means the above "alkenyloxy" bonded to a carbonyl group. Examples of "alkenyloxycarbonyl" include ethylenyloxycarbonyl, propenyloxycarbonyl and the like.

"Alkynyloxycarbonyl" means the above "alkynyloxy" bonded to a carbonyl group. Examples of "alkynyloxycarbonyl" include ethynyloxycarbonyl, propynyloxycarbonyl and the like.

"Non-aromatic carbocyclyloxycarbonyl" means the above "non-aromatic carbocyclyloxy" bonded to a carbonyl group. For example, cyclopropyloxycarbonyl, cyclopentynyloxycarbonyl, cyclohexyloxycarbonyl, cyclopropenyloxycarbonyl, cyclopentenyloxycarbonyl, cyclohexenyloxycarbonyl and the like are exemplified.

"Aromatic carbocyclyloxycarbonyl" means the above "aromatic carbocyclyloxy" bonded to a carbonyl group. For example, phenyloxycarbonyl, naphthyloxycarbonyl and the like are exemplified.

"Aromatic heterocyclyloxycarbonyl" means the above "aromatic heterocyclyloxy" bonded to a carbonyl group. For example, pyridyloxycarbonyl, oxazolyloxycarbonyl and the like are exemplified.

"Non-aromatic heterocyclyloxycarbonyl" means the above "non-aromatic heterocyclyloxy" bonded to a carbonyl group. For example, piperidinyloxycarbonyl, tetrahydrofuryloxycarbonyl and the like are exemplified.

"Alkylcarbonylsulfanyl" means the above "alkylcarbonyl" bonded to a sulfur atom. For example, methylcarbonylsulfanyl, ethylcarbonylsulfanyl, n-propylcarbonylsulfanyl, isopropylcarbonylsulfanyl, n-butylcarbonylsulfanyl, tert-butylcarbonylsulfanyl, isobutylcarbonylsulfanyl, sec-butylcarbonylsulfanyl, pentylcarbonylsulfanyl, isopentylcarbonylsulfanyl, hexylcarbonylsulfanyl and the like are exemplified. A preferable embodiment of "alkylcarbonylsulfanyl" includes methylcarbonylsulfanyl, ethylcarbonylsulfanyl, propylcarbonylsulfanyl, isopropylcarbonylsulfanyl, tert-butylcarbonylsulfanyl, isobutylcarbonylsulfanyl, sec-butylcarbonylsulfanyl and the like.

"Haloalkyl" means the above "alkyl" the one or more arbitrary hydrogen(s) of which is(are) substituted with the above "halogen". For example, monofluoromethyl, monofluoroethyl, monofluoropropyl, 2, 2, 3, 3, 3-pentafluoropropyl, monochloromethyl, trifluoromethyl, trichloromethyl, 2, 2, 2-trifluoroethyl, 2, 2, 2-trichloroethyl, 1, 2-dibromoethyl, 1, 1, 1-trifluoropropane-2-yl and the like are exemplified.

"Haloalkylcarbonyl" means the above "haloalkyl" bonded to a carbonyl group. For example, monofluoromethylcarbonyl, difluoromethylcarbonyl, monofluoroethylcarbonyl, monofluoropropylcarbonyl, 2, 2, 3, 3, 3-pentafluoropropylcarbonyl, monochloromethylcarbonyl, trifluoromethylcarbonyl, trichloromethylcarbonyl, 2, 2, 2-trifluoroethylcarbonyl, 2, 2, 2-trichloroethylcarbonyl, 1, 2-dibromoethylcarbonyl, 1, 1, 1-trifluoropropane-2-ylcarbonyl and the like are exemplified.

"Haloalkenyl" means the above "alkenyl" the one or more arbitrary hydrogen(s) of which is (are) substituted with the above "halogen".

"Hydroxyalkyl" means the above "alkyl" the one or more arbitrary hydrogen(s) of which is (are) substituted with "hydroxyl".

"Trialkylsilyl" means silicon atom bonded to above three "alkyl" group. Three alkyl groups may be same or different. For example, trimethylsilyl, triethylsilyl, tert-butyldimethylsilyl, triisopropylsilyl and the like are exemplified.

"Trialkylsilyloxy" means the above "trialkylsilyl" bonded to an oxygen atom. For example, trimethylsilyloxy, triethylsilyloxy, tert-butyldimethylsilyloxy, triisopropylsilyloxy and the like are exemplified.

"Cyanoalkyl" means the above "alkyl" the one or more arbitrary hydrogen(s) of which is (are) substituted with cyano. For example, cyanomethyl and the like are exemplified.

"Cyanoalkyloxy" means the above "cyanoalkyl" bonded to an oxygen atom. For example, cyanomethyloxy and the like are exemplified.

"Haloalkyloxy" means the above "haloalkyl" bonded to an oxygen atom. For example, monofluoromethyloxy, monofluoroethyloxy, trifluoromethyloxy, trichloromethyloxy, trifluoroethyloxy, trichloroethyloxy and the like are exemplified.

A preferable embodiment of "haloalkyloxy" includes trifluoromethyloxy, trichloromethyloxy and the like.

"Carbamoylalkylcarbonyl" means the above "alkylcarbonyl" substituted with carbamoyl. For example, carbamoylmethylcarbonyl, carbamoylethylcarbonyl and the like are exemplified.

"Monoalkylamino" means an amino group one hydrogen atom bonded to the nitrogen atom of which is substituted with the above "alkyl". Examples of "monoalkylamino" include methylamino, ethylamino and the like.

"Dialkylamino" means an amino group two hydrogen atoms bonded to the nitrogen atom of which are substituted with the above "alkyl". Two alkyl groups may be same or different. For example, dimethylamino, diethylamino, N, N-diisopropylamino, N-methyl-N-ethylamino, N-isopropyl-N-ethylamino and the like are exemplified.

A preferable embodiment of "dialkylamino" includes dimethylamino, diethylamino and the like.

"Monoalkylcarbonylamino" means an amino group one hydrogen atom bonded to the nitrogen atom of which is replaced with the above "alkylcarbonyl". For example, methylcarbonylamino, ethylcarbonylamino, propylcarbonylamino, isopropylcarbonylamino, tert-butylcarbonylamino, isobutylcarbonylamino, sec-butylcarbonylamino and the like are exemplified.

A preferable embodiment of "monoalkylcarbonyl amino" includes methylcarbonylamino, ethylcarbonylamino and the like.

"Dialkylcarbonylamino" means an amino group two hydrogen atoms bonded to the nitrogen atom of which are replaced with the above "alkylcarbonyl". Two alkylcarbonyl groups may be same or different. For example, dimethylcarbonylamino, diethylcarbonylamino, N,N-diisopropylcarbonylamino and the like are exemplified.

A preferable embodiment of "dialkylcarbonylamino" includes dimethylcarbonylamino, diethylcarbonylamino and the like.

"Monoalkyloxycarbonylamino" means an amino group one hydrogen atom bonded to the nitrogen atom of which is replaced with the above "alkyloxycarbonyl". A preferable embodiment of "monoalkyloxycarbonylamino" includes methyloxycarbonylamino, ethyloxycarbonylamino and the like.

"Dialkyloxycarbonylamino" means an amino group two hydrogen atoms bonded to the nitrogen atom of which are replaced with the above "alkyloxycarbonyl". Two alkyloxycarbonyl groups may be same or different.

"Monoalkylsulfonylamino" means an amino group one hydrogen atom bonded to the nitrogen atom of which is replaced with the above "alkylsulfonyl". For example, methylsulfonylamino, ethylsulfonylamino, propylsulfonylamino, isopropylsulfonylamino, tert-butylsulfonylamino, isobutylsulfonylamino, sec-butylsulfonylamino and the like are exemplified.

A preferable embodiment of "monoalkylsulfonylamino" includes methylsulfonylamino, ethylsulfonylamino and the like.

"Dialkylsulfonylamino" means an amino group two hydrogen atoms bonded to the nitrogen atom of which are replaced with the above "alkylsulfonyl". Two alkylsulfonyl groups may be same or different. For example, dimethylsulfonylamino, diethylsulfonylamino, N, N-diisopropylsulfonylamino and the like are exemplified.

A preferable embodiment of "dialkylsulfonylamino" includes dimethylsulfonylamino, diethylsulfonylamino and the like.

"Alkylimino" means an imino group a hydrogen atom bonded to the nitrogen atom of which is replaced with the above "alkyl". For example, methylimino, ethylimino, n-propylimino, isopropylimino and the like are exemplified.

"Alkenylimino" means an imino group a hydrogen atom bonded to the nitrogen atom of which is replaced with the above "alkenyl". For example, ethylenylimino, propenylimino and the like are exemplified.

"Alkynylimino" means an imino group a hydrogen atom bonded to the nitrogen atom of which is replaced with the above "alkynyl". For example, ethynylimino, propynylimino and the like are exemplified.

"Alkylcarbonylimino" means an imino group a hydrogen atom bonded to the nitrogen atom of which is replaced with the above "alkylcarbonyl". For example, methylcarbonylimino, ethylcarbonylimino, n-propylcarbonylimino, isopropylcarbonylimino and the like are exemplified.

"Alkenylcarbonylimino" means an imino group a hydrogen atom bonded to the nitrogen atom of which is replaced with the above "alkenylcarbonyl". For example, ethylenylcarbonylimino, propenylcarbonylimino and the like are exemplified.

"Alkynylcarbonylimino" means an imino group a hydrogen atom bonded to the nitrogen atom of which is replaced with the above "alkynylcarbonyl". For example, ethynylcarbonylimino, propynylcarbonylimino and the like are exemplified.

"Alkyloxyimino" means an imino group a hydrogen atom bonded to the nitrogen atom of which is replaced with the above "alkyloxy". For example, methyloxyimino, ethyloxyimino, n-propyloxyimino, isopropyloxyimino and the like are exemplified.

"Alkenyloxyimino" means an imino group a hydrogen atom bonded to the nitrogen atom of which is replaced with the above "alkenyloxy". For example, ethylenyloxyimino, propenyloxyimino and the like are exemplified.

"Alkynyloxyimino" means an imino group a hydrogen atom bonded to the nitrogen atom of which is replaced with the above "alkynyloxy". For example, ethynyloxyimino, propynyloxyimino and the like are exemplified.

"Monoalkylcarbamoyl" means a carbomoyl group a hydrogen atom bonded to the nitrogen atom of which is replaced with the above "alkyl". For example, methylcarbamoyl, ethylcarbamoyl and the like are exemplified.

"Monoalkylcarbamoylalkyloxy" means the above "alkyloxy" substituted with one or more the above "monoalkylcarbamoyl". For example, methylcarbamoylmethyloxy and the like are exemplified.

"Mono(hydroxyalkyl)carbamoyl" means the above "monoalkylcarbamoyl" the arbitrary hydrogen atoms of which is replaced with a hydroxyl group. For example, hydroxymethylcarbamoyl, hydroxyethylcarbamoyl and the like are exemplified.

"Dialkylcarbamoyl" means a carbamoyl group two hydrogen atoms bonded to the nitrogen atom of which are replaced with the above "alkyl". Two alkyl groups may be same or different. For example, dimethylcarbamoyl, diethylcarbamoyl and the like are exemplified.

"Alkyloxycarbonylalkyl" means the above "alkyl" substituted with one or more the above "alkyloxycarbonyl".

"Monoalkyloxycarbonylalkylcarbamoyl" means a carbamoyl group one hydrogen atom bonded to nitrogen atom of which is replaced with the above "alkyloxycarbonylalkyl". For example, methyloxycarbonylmethylcarbamoyl, ethyloxycarbonylmethylcarbamoyl and the like are exemplified.

"Dialkyloxycarbonylalkylcarbamoyl" means a carbamoyl group two hydrogen atoms bonded to the nitrogen atom of which is replaced with the above "alkyloxycarbonylalkyl".

"Carboxyalkyl" means the above "alkyl" substituted with one or more above "carboxy".

"Carboxyalkylcarbamoyl" means a carbamoyl group one or more two hydrogen atom(s) bonded to the nitrogen atom of which is (are) replaced with one or more above "carboxyalkyl". For example, carboxymethylcarbamoyl and the like are exemplified.

"Dialkylaminoalkyl" means the above "alkyl" substituted with one or more above "dialkylamino". For example, dimethylaminomethyl, dimethylaminoethyl and the like are exemplified.

"Mono(dialkylaminoalkyl)carbamoyl" means a carbamoyl group one hydrogen atom bonded to the nitrogen atom of which is replaced with the above "dialkylaminoalkyl". For example, dimethylaminomethylcarbamoyl, dimethylaminoethylcarbamoyl and the like are exemplified.

"Di(dialkylaminoalkyl)carbamoyl" means a carbamoyl group two hydrogen atoms bonded to the nitrogen atom of which are replaced with the above "dialkylaminoalkyl". For example, di(methyloxycarbonylmethyl)carbamoyl, di(ethyloxycarbonylmethyl)carbamoyl and the like are exemplified.

"Non-aromatic carbocyclylcarbamoyl" means a carbamoyl group one or two hydrogen atom(s) bonded to nitrogen atom of which is(are) replaced with one or more above "non-aromatic carbocyclyl". For example, cyclopropylcarbamoyl and the like are exemplified.

"Non-aromatic heterocyclylcarbamoyl" means a carbamoyl group the hydrogen atom bonded to nitrogen atom of which is replaced with one or more above "non-aromatic heterocyclyl". Examples include a group represented by the following formula:

[Formula 42]

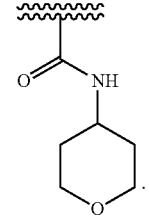

"Monoalkyloxycarbamoyl" means a carbamoyl group one hydrogen atom bonded to the nitrogen atom of which is replaced with the above "alkyloxy". For example, methyloxycarbamoyl and the like are exemplified.

"Dialkyloxycarbamoyl" means a carbomoyl group two hydrogen atoms bonded to the nitrogen of which are replaced with the above "alkyloxy". For example, di(methyloxy)carbamoyl and the like are exemplified.

"Monoalkylsulfamoyl" means a sulfamoyl group one hydrogen atom bonded to nitrogen atom of which is replaced with the above "alkyl". For example, methylsulfamoyl, ethylsulfamoyl and the like are exemplified.

"Dialkylsulfamoyl" means a sulfamoyl group two hydrogen atoms bonded to the nitrogen atom of which are replaced with the above "alkyl". Two alkyl groups may be same or different. For example, dimethylsulfamoyl, diethylsulfamoyl and the like are exemplified.

"Aromatic carbocyclylalkyl" means the above "alkyl" substituted with one or more above "aromatic carbocyclyl".

For example, benzyl, phenethyl, phenylpropyl, benzhydryl, trityl, naphthylmethyl, a group represented by the following formula:

[Formula 43]

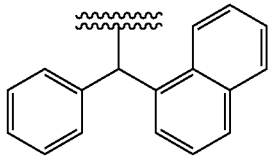

and the like are exemplified.

A preferable embodiment of "aromatic carbocyclylalkyl" includes benzyl, phenethyl, benzhydryl and the like.

"Cycloalkylalkyl" means the above "alkyl" substituted with one or more above "cycloalkyl". "Cycloalkylalkyl" includes "cycloalkylalkyl" which the alkyl part is further substituted with the above "aromatic carbocyclyl". For example, cyclopentylmethyl, cyclohexylmethyl, a group represented by the following formula:

[Formula 44]

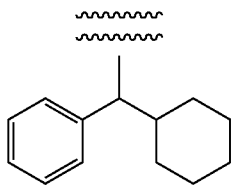

and the like are exemplified.

"Cycloalkenylalkyl" means the above "alkyl" substituted with one or more above "cycloalkenyl". "Cycloalkenylalkyl" includes "cycloalkenylalkyl" which the alkyl part is further substituted with the above "aromatic carbocyclyl". For example, cyclopropenylmethyl, cyclobutenylmethyl, cyclopentenylmethyl, cyclohexenylmethyl, and the like are exemplified.

"Aromatic heterocyclylalkyl" means the above "alkyl" substituted with one or more above "aromatic carbocyclyl". "Aromatic heterocyclylalkyl" includes "aromatic heterocyclylalkyl" which the alkyl part is further substituted with the above "aromatic carbocyclyl" and/or "non-aromatic carbocyclyl". For example, pyridylmethyl, furanylmethyl, imidazolylmethyl, indolylmethyl, benzothiophenylmethyl, oxazolylmethyl, isoxazolylmethyl, thiazolylmethyl, isothiazolylmethyl, pyrazolylmethyl, isopyrazolylmethyl, pyrrolidinylmethyl, benzoxazolylmethyl, a group represented by the following formula:

[Formula 45]

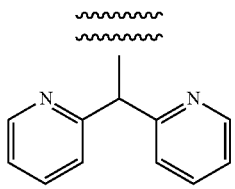

-continued

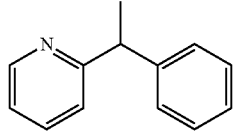

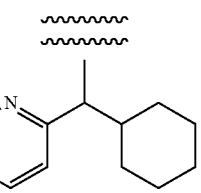

and the like are exemplified.

"Non-aromatic heterocyclylalkyl" means the above "alkyl" substituted with one or more above "non-aromatic heterocyclyl". "Non-aromatic heterocyclylalkyl" includes "non-aromatic heterocyclylalkyl" which the alkyl part is further substituted with the above "aromatic carbocyclyl", "non-aromatic carbocyclyl" and/or "aromatic heterocyclyl". For example, tetrahydropyranylmethyl, morpholinylethyl, piperidinylmethyl, piperazinylmethyl, a group represented by the following formula:

[Formula 46]

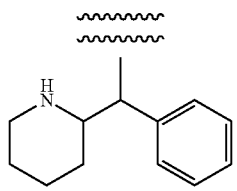

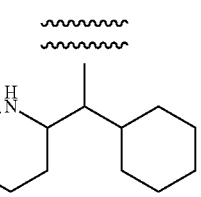

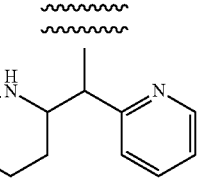

and the like are exemplified.

"Non-aromatic heterocyclylalkylcarbamoyl" means a carbamoyl group one or two hydrogen atom(s) bonded to nitrogen atom of which is replaced with one or two above "non-aromatic heterocyclylalkyl". For example, a group represented by the following formula is exemplified:

[Formula 47]

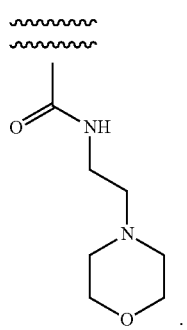

"Aromatic carbocyclylalkyloxy" means the above "alkyloxy" substituted with one or more above "aromatic carbocycle". For example, benzyloxy, phenethyloxy, phenylpropynyloxy, benzhydryloxy, trityloxy, naphthylmethyloxy, a group represented by the following formula:

[Formula 48]

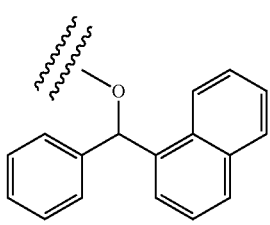

and the like are exemplified.

"Non-aromatic carbocyclylalkyloxy" means the above "alkyloxy" substituted with one or more above "non-aromatic carbocyclyl". "Non-aromatic carbocyclylalkyloxy" includes "non-aromatic carbocyclylalkyloxy" which the alkyl part are further substituted with the above "aromatic carbocyclyl". For example, cyclopeopylmethyloxy, cyclobutylmethyloxy, cyclopenthylmethyloxy, cyclohexylmethyloxy, cyclopropylmethyloxy, cyclobutylmethyloxy, cyclopenthylmethyloxy, cyclohexylmethyloxy, a group represented by the following formula:

[Formula 49]

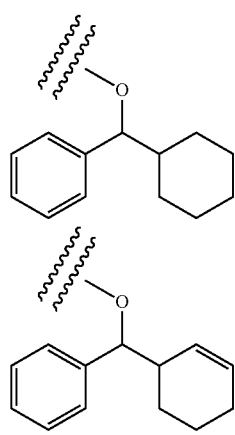

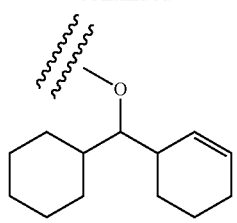

and the like are exemplified.

"Aromatic heterocyclylalkyloxy" means the above "alkyloxy" substituted with one or more above "aromatic heterocyclyl". "Aromatic heterocyclylalkyloxy" includes "aromatic heterocyclylalkyloxy" which the alkyl part is further substituted with the above "aromatic carbocyclyl" and/or "non-aromatic carbocyclyl". For example, pyridylmethyloxy, furanylmethyloxy, imidazolylmethyloxy, indolylmethyloxy, benzothiophenylmethyloxy, oxazolylmethyloxy, isoxazolylmethyloxy, thiazolylmethyloxy, isothiazolylmethyloxy, pyrazolylmethyloxy, isopyrazolylmethyloxy, pyrrolidinylmethyloxy, benzoxazolylmethyloxy, a group represented by the following formula:

[Formula 50]

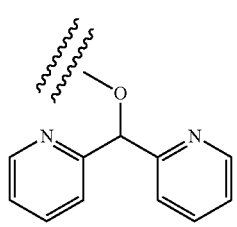

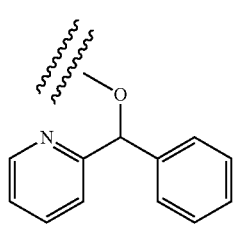

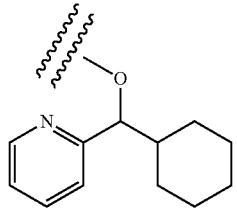

and the like are exemplified.

"Non-aromatic heterocyclylalkyloxy" means the above "alkyloxy" substituted with one or more above "non-aromatic heterocyclyl". "Non-aromatic heterocyclylalkyloxy" includes "non-aromatic heterocyclylalkyloxy" which the alkyl part is further substituted with the above "aromatic carbocyclyl", "non-aromatic carbocyclyl" and/or "aromatic heterocyclyl". For example, tetrahydropyranylmethyloxy, morpholinylethyloxy, piperidinylmethyloxy, piperazinylmethyloxy, a group represented by the following formula:

[Formula 51]

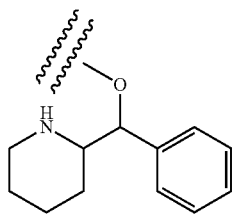

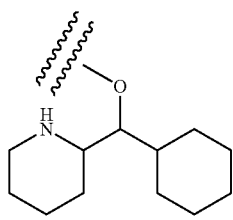

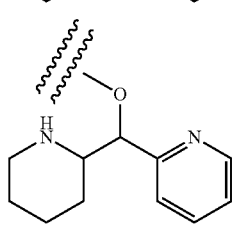

and the like are exemplified.

"Aromatic carbocyclylalkyloxycarbonyl" means the above "alkyloxycarbonyl" substituted with one or more above "aromatic carbocyclyl". For example, benzyloxycarbonyl, phenethyloxycarbonyl, phenylpropynyloxycarbonyl, benzhydryloxycarbonyl, trityloxycarbonyl, naphthylmethyloxycarbonyl, a group represented by the following formula:

[Formula 52]

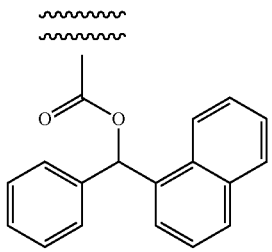

and the like are exemplified.

"Non-aromatic carbocyclylalkyloxycarbonyl" means the above "alkyloxycarbonyl" substituted with one or more above "non-aromatic carbocyclyl". "Non-aromatic carbocyclylalkyloxycarbonyl" includes "non-aromatic carbocyclylalkyloxycarbonyl" which the alkyl part is further substituted with the above "aromatic carbocyclyl". For example, cyclopropylmethyloxycarbonyl, cyclobutylmethyloxycarbonyl, cyclopentylmethyloxycarbonyl, cyclohexylmethyloxycarbonyl, cyclopropenylmethyloxycarbonyl, cyclobutenylmethyloxycarbonyl, cyclopentenylmethyloxycarbonyl, cyclohexenylmethyloxycarbonyl, a group represented by the following formula:

[Formula 53]

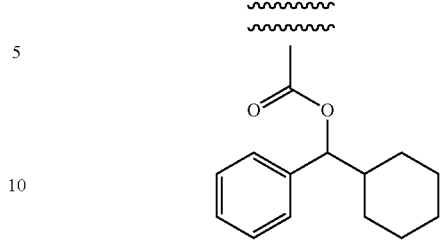

and the like are exemplified.

"Aromatic heterocyclylalkyloxycarbonyl" means the above "alkyloxycarbonyl" substituted with one or more above "aromatic heterocyclyl". "Aromatic heterocyclylalkyloxycarbonyl" includes "aromatic heterocyclylalkyloxycarbonyl" which the alkyl part is further substituted with the above "aromatic carbocyclyl" and/or "non-aromatic carbocyclyl". For example, pyridylmethyloxycarbonyl, furanylmethyloxycarbonyl, imidazolylmethyloxycarbonyl, indolylmethyloxycarbonyl, benzothiophenylmethyloxycarbonyl, oxazolylmethyloxycarbonyl, isoxazolylmethyloxycarbonyl, thiazolylmethyloxycarbonyl, isothiazolylmethyloxycarbonyl, pyrazolylmethyloxycarbonyl, isopyrazolylmethyloxycarbonyl, pyrrolidinylmethyloxycarbonyl, benzoxazolylmethyloxycarbonyl, a group represented by the following formula:

[Formula 54]

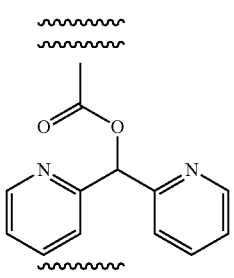

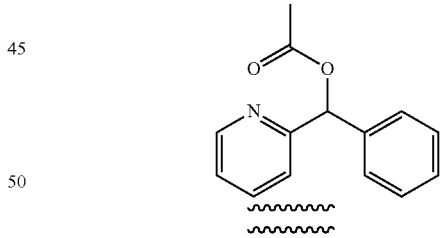

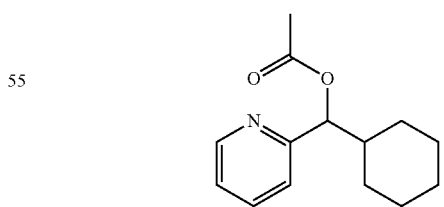

and the like are exemplified.

"Non-aromatic heterocyclylalkyloxycarbonyl" means the above "alkyloxycarbonyl" substituted with one or more above "non-aromatic heterocyclyl". "Non-aromatic heterocyclylalkyloxycarbonyl" includes "non-aromatic heterocyclylalkyloxycarbonyl" which the alkyl part is further substituted with the above "aromatic carbocyclyl", "non-aromatic carbocyclyl" and/or "aromatic heterocycle". For example, tetrahydropyranylmethyloxy, morpholinylethyloxy, piperidinylmethyloxy, piperazinylmethyloxy, a group represented by the following formula:

[Formula 55]

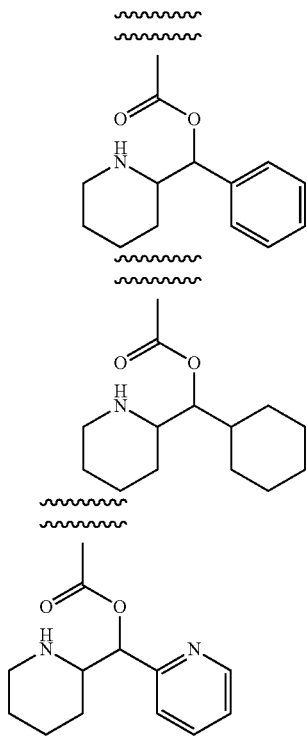

and the like are exemplified.

"Aromatic carbocyclylalkylamino" means an amino group one or two hydrogen atom(s) bonded to the nitrogen atom of which is (are) replaced with the above "aromatic carbocyclylalkyl". For example, benzylamino, phenethylamino, phenylpropynylamino, benzhydrylamino, tritylamino, naphthylmethylamino, dibenzylamino and the like are exemplified.

"Non-aromatic carbocyclylalkylamino" means an amino group one or two hydrogen atom(s) bonded to the nitrogen atom of which is (are) replaced with the above "non-aromatic carbocyclylalkyl". For example, cyclopropylmethylamino, cyclobutylmethylamino, cyclopentylmethylamino, cyclohexylmethylamino, cyclopropenylmethylamino, cyclobutenylmethylamino, cyclopentenylmethylamino, cyclohexenylmethylamino and the like are exemplified.

"Aromatic heterocyclylalkylamino" means an amino group one or two hydrogen atom(s) bonded to the nitrogen atom of which is (are) replaced with the above "aromatic heterocyclylalkyl". For example, pyridylmethylamino, franylmethylamino, imidazolylmethylamino, indolylmethylamino, benzothiophenylmethylamino, oxazolylmethylamino, isoxazolylmethylamino, thiazolylmethylamino, isothiazolylmethylamino, pyrazolylmethylamino, isopyrazolylmethylamino, pyrrolidinylmethylamino, benzoxazolylmethylamino and the like are exemplified.

"Non-aromatic heterocyclylalkylamino" means an amino group one or two hydrogen atom(s) bonded to the nitrogen atom of which is (are) replaced with the above "non-aromatic heterocyclylalkyl". For example, tetrahydropyranylmethylamino, morpholinylethylamino, piperidinylmethylamino, piperazinylmethylamino and the like are exemplified.

"Alkyloxyalkyl" means the above "alkyl" substituted with one or two above "alkyloxy". For example, methyloxymethyl, methyloxyethyl, ethyloxymethyl and the like are exemplified.

"Aromatic carbocyclylalkyloxyalkyl" means the above "alkyloxyalkyl" substituted with one or more above "aromatic carbocyclyl". For example, benzyloxymethyl, phenethyloxymethyl, phenylpropynyloxymethyl, benzhydryloxymethyl, trityloxymethyl, naphthylmethyloxymethyl, a group represented by the following formula:

[Formula 56]

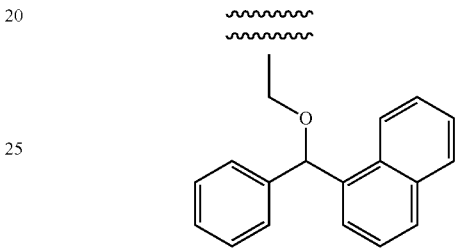

and the like are exemplified.

"Non-aromatic carbocyclylalkyloxyalkyl" means the above "alkyloxyalkyl" substituted with one or more above "non-aromatic carbocyclyl". "Non-aromatic carbocyclylalkyloxyalkyl" includes "non-aromatic carbocyclylalkyloxyalkyl" which the alkyl part bonded to the non-aromatic heterocycle is further substituted with the above "aromatic carbocyclyl". For example, cyclopropylmethyloxymethyl, cyclobutylmethyloxymethyl, cyclopentylmethyloxymethyl, cyclohexylmethyloxymethyl, cyclopropenylmethyloxymethyl, cyclobutenylmethyloxymethyl, cyclopentenylmethyloxymethyl, cyclohexenylmethyloxymethyl, groups represented by the following formula:

[Formula 57]

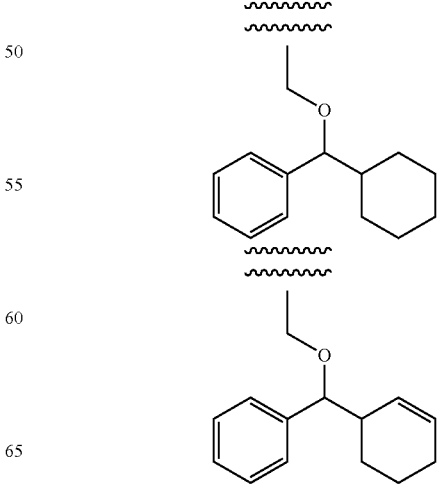

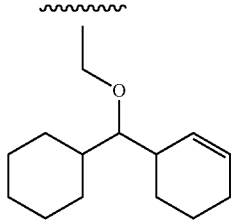

and the like are exemplified.

"Aromatic heterocyclylalkyloxyalkyl" means the above "alkyloxyalkyl" substituted with one or more above "aromatic heterocyclyl". "Aromatic heterocyclylalkyloxyalkyl" includes "aromatic heterocyclylalkyloxyalkyl" which the alkyl part bonded to the aromatic heterocycle is further substituted with the above "aromatic carbocyclyl" and/or "non-aromatic carbocyclyl". For example, pyridylmethyloxymethyl, franylmethyloxymethyl, imidazolylmethyloxymethyl, indolylmethyloxymethyl, benzothiophenylmethyloxymethyl, oxazolylmethyloxymethyl, isoxazolylmethyloxymethyl, thiazolylmethyloxymethyl, isothiazolylmethyloxymethyl, pyrazolylmethyloxymethyl, isopyrazolylmethyloxymethyl, pyrrolidinylmethyloxymethyl, benzoxazolylmethyloxymethyl, groups represented by the following formula:

[Formula 58]

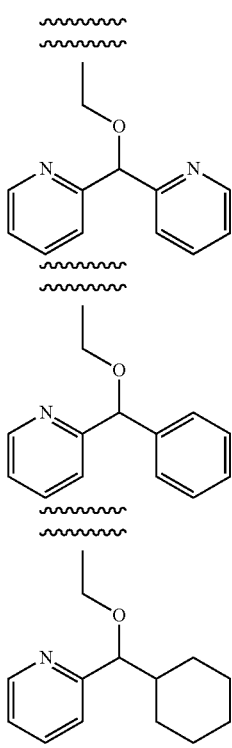

and the like are exemplified.

"Non-aromatic heterocyclylalkyloxyalkyl" means the above "alkyloxyalkyl" substituted with one or more above "non-aromatic heterocyclyl". "Non-aromatic heterocyclylalkyloxyalkyl" includes "non-aromatic heterocyclylalkyloxyalkyl" which the alkyl part bonded to the non-aromatic heterocycle is further substituted with the above "aromatic carbocyclyl", "non-aromatic carbocyclyl" and/or "aromatic heterocyclyl". For example, tetrahydropyranylmethyloxymethyl, morpholinylethyloxymethyl, piperidinylmethyloxymethyl, piperazinylmethyloxymethyl, groups represented by the following formula:

[Formula 59]

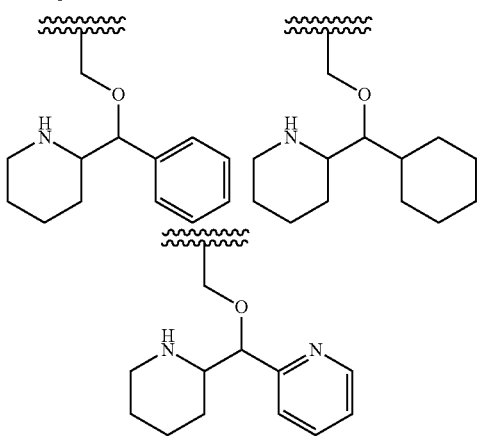

and the like are exemplified.

"Alkyloxyalkyloxy" means the above "alkyloxyalkyl" bonded to an oxygen atom.

Substitutents on the nitrogen atom in the above "substituted or unsubstituted amino", "substituted or unsubstituted carbamoyl", "substituted or unsubstituted sulfamoyl", "substituted or unsubstituted amidino" and "substituted or unsubstituted aminosulfinyl" include the following substituents. Hydrogen on the nitrogen atom can be replaced with one or two substituents selected from the following substituents.

Substituents:

alkyl, alkenyl, alkynyl, haloalkyl, haloalkenyl, halogen, hydroxy, carboxy, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azido, hydradino, ureido, amidino, guanidino, trialkylsilyl, alkyloxy, alkyloxyalkyloxy, alkenyloxy, alkynyloxy, haloalkyloxy, trialkylsilyloxy, cyanoalkyloxy, alkylcarbonyl, haloalkylcarbonyl, carbamoylalkylcarbonyl, alkenylcarbonyl, alkynylcarbonyl, monoalkylamino, dialkylamino, alkylsulfonyl, alkenylsulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, monoalkyloxycarbonylamino, dialkyloxycarbonylamino, alkenyloxycarbonyl, alkynyloxycarbonyl, alkylsulfanyl, alkylcarbonylsulfanyl, alkenylsulfanyl, alkynylsulfanyl, alkylsulfinyl, alkenylsulfinyl, alkynylsulfinyl, monoalkylcarbamoyl, mono(hydroxyalkyl)carbamoyl, dialkylcarbamoyl, hydroxycarbamoyl, cyanocarbamoyl, carboxyalkylcarbamoyl, mono(dialkylaminoalkyl)carbamoyl, di(dialkylaminoalkyl) carbamoyl, non-aromatic carbocyclylalkylcarbamoyl, non-aromatic carbocyclylcarbamoyl, non-aromatic heterocyclylalkylcarbamoyl, non-aromatic heterocyclylcarbamoyl, monoalkyloxycarbamoyl, dialkyloxycarbamoyl, monoalkyloxycarbonylalkylcarbamoyl, dialkyloxycarbonylalkylcarbamoyl, monoalkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, non-aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, non-aromatic carbocyclylcarbonyloxy, aromatic carbocyclylcarbonyloxy, aromatic heterocyclylcarbonyloxy, non-aromatic heterocyclylcarbonyloxy, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalkyl, non-aromatic carbocyclylalkyl, aromatic heterocyclylalkyl, non-aromatic heterocyclylalkyl, aromatic carbocyclylalkyloxy, non-aromatic carbocyclylalkyloxy, aromatic heterocyclylalkyloxy, non-aromatic heterocyclylalkyloxy, aromatic carbocyclylalkyloxycarbonyl, non-aromatic carbocyclylalkyloxycarbonyl, aromatic heterocyclylalkyloxycarbonyl, non-aromatic heterocyclylalkyloxycarbonyl, aromatic carbocyclylalkylamino, non-aromatic carbocyclylalkylamino, aromatic heterocyclylalkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, aromatic carbocyclylsulfonyl, non-aromatic carbocyclylsulfonyl, aromatic heterocyclylsulfonyl, non-aromatic heterocyclylsulfonyl, alkylsulfonyloxy, alkenylsulfonyloxy, alkynylsulfonyloxy, non-aromatic carbocyclylsulfonyloxy, aromatic carbocyclylsulfonyloxy, aromatic heterocyclylsulfonyloxy, non-aromatic heterocyclylsulfonyloxy, alkyloxycarbonylalkyl, carboxyalkyl, hydroxyalkyl, dialkylaminoalkyl, hydroxyalkyl, alkyloxyalkyl, aromatic carbocyclylalkyloxyalkyl, non-aromatic carbocyclylalkyloxyalkyl, aromatic heterocyclylalkyloxyalkyl, and non-aromatic heterocyclylalkyloxyalkyl.

Substituents of the above "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylsulfanyl", "substituted or unsubstituted alkenylsulfanyl", "substituted or unsubstituted alkynylsulfanyl", "substituted or unsubstituted alkylcarbonyl", "substituted or unsubstituted alkenylcarbonyl", "substituted or unsubstituted alkynylcarbonyl", "substituted or unsubstituted alkylsulfonyl", "substituted or unsubstituted alkenylsulfonyl", "substituted or unsubstituted alkynylsulfonyl", "substituted or unsubstituted alkyloxycarbonyl", "substituted or unsubstituted alkenyloxycarbonyl", "substituted or unsubstituted alkynyloxycarbonyl", "substituted or unsubstituted alkylsulfinyl", "substituted or unsubstituted alkenylsulfinyl", "substituted or unsubstituted alkynylsulfinyl", "substituted or unsubstituted alkylsulfonyloxy", "substituted or unsubstituted alkenylsulfonyloxy", "substituted or unsubstituted alkynylsulfonyloxy", "substituted or unsubstituted alkylcarbonyloxy", "substituted or unsubstituted alkenylcarbonyloxy" and "substituted or unsubstituted alkynylcarbonyloxy" include the following substituents. Hydrogen atom on the carbon atom at arbitrary position(s) can be replaced with one or more substituents selected from the following substituents.

Substituents:
halogen, hydroxy, carboxy, amino, imino, hydroxy amino, hydroxy imino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azido, hydradino, ureido, amidino, guanidino, trialkylsilyl, alkyloxy, alkyloxyalkyloxy, alkenyloxy, alkynyloxy, haloalkyloxy, trialkylsilyloxy, cyanoalkyloxy, alkylcarbonyl, haloalkylcarbonyl, carbamoylalkylcarbonyl, alkenylcarbonyl, alkynylcarbonyl, monoalkylamino, dialkylamino, alkylsulfonyl, alkenylsulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, monoalkyloxycarbonylamino, dialkyloxycarbonylamino, alkenyloxycarbonyl, alkynyloxycarbonyl, alkylsulfanyl, alkylcarbonylsulfanyl, alkenylsulfanyl, alkynylsulfanyl, alkylsulfinyl, alkenylsulfinyl, alkynylsulfinyl, monoalkylcarbamoyl, mono(hydroxyalkyl)carbamoyl, dialkylcarbamoyl, hydroxycarbamoyl, cyanocarbamoyl, carboxyalkylcarbamoyl, mono(dialkylaminoalkyl)carbamoyl, di(dialkylaminoalkyl)carbamoyl, non-aromatic carbocyclylcarbamoyl, non-aromatic heterocyclylalkylcarbamoyl, non-aromatic heterocyclylcarbamoyl, mono alkyloxycarbamoyl, dialkyloxycarbamoyl, monoalkyloxycarbonylalkylcarbamoyl, dialkyloxycarbonylalkylcarbamoyl, monoalkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, non-aromatic carbocyclylcarbonyloxy, aromatic carbocyclylcarbonyloxy, aromatic heterocyclylcarbonyloxy, non-aromatic heterocyclylcarbonyloxy, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalkyloxy, non-aromatic carbocyclylalkyloxy, aromatic heterocyclylalkyloxy, non-aromatic heterocyclylalkyloxy, aromatic carbocyclylalkyloxycarbonyl, non-aromatic carbocyclylalkyloxycarbonyl, aromatic heterocyclylalkyloxycarbonyl, non-aromatic heterocyclylalkyloxycarbonyl, aromatic carbocyclylalkylamino, non-aromatic carbocyclylalkylamino, aromatic heterocyclylalkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, non-aromatic carbocyclylsulfonyl, aromatic carbocyclylsulfonyl, aromatic heterocyclylsulfonyl, non-aromatic heterocyclylsulfonyl, alkylsulfonyloxy, alkenyl sulfonyloxy, alkynylsulfonyloxy, non-aromatic carbocyclylsulfonyloxy, aromatic carbocyclylsulfonyloxy, aromatic heterocyclylsulfonyloxy and non-aromatic heterocyclylsulfonyloxy.

Substituents in the ring of the above "substituted or unsubstituted fused aromatic heterocyclyl", "substituted or unsubstituted non-aromatic carbocycle", "substituted or unsubstituted aromatic carbocycle", "substituted or unsubstituted non-aromatic heterocycle", "substituted or unsubstituted aromatic heterocycle", "substituted or unsubstituted non-aromatic carbocyclyl", "substituted or unsubstituted aromatic carbocyclyl", "substituted or unsubstituted non-aromatic heterocyclyl", "substituted or unsubstituted aromatic heterocyclyl", "substituted or unsubstituted non-aromatic carbocyclylcarbonyl", "substituted or unsubstituted aromatic carbocyclylcarbonyl", "substituted or unsubstituted aromatic heterocyclylcarbonyl", "substituted or unsubstituted non-aromatic heterocyclylcarbonyl", "substituted or unsubstituted non-aromatic carbocyclylsulfonyl", "substituted or unsubstituted aromatic carbocyclylsulfonyl", "substituted or unsubstituted aromatic heterocyclylsulfonyl", "substituted or unsubstituted non-aromatic heterocyclylsulfonyl", "substituted or unsubstituted non-aromatic carbocyclyl", "substituted or unsubstituted aromatic carbocyclyl", "substituted or unsubstituted aromatic heterocyclyl", "substituted or unsubstituted fused aromatic carbocyclyl", "substituted or unsubstituted fused aromatic heterocyclyl", "substituted or unsubstituted non-aromatic heterocyclyl", "substituted or unsubstituted aromatic carbocyclyloxycarbonyl", "substituted or unsubstituted non-aromatic carbocyclyloxycarbonyl", "substituted or unsubstituted aromatic heterocyclyloxycarbonyl", "substituted or unsubstituted non-aromatic heterocyclyloxycarbonyl", "substituted or unsubstituted non-aromatic carbocyclyloxy", "substituted or unsubstituted aromatic carbocyclyloxy", "substituted or unsubstituted aromatic heterocyclyloxy", "substituted or unsubstituted non-aromatic heterocyclyloxy", "substituted or unsubstituted non-aromatic carbocyclylsulfanyl", "substituted or unsubstituted aromatic carbocyclylsulfanyl", "substituted or unsubstituted aromatic heterocyclylsulfanyl", "substituted or unsubstituted non-aromatic heterocyclylsulfanyl", "substituted or unsubstituted non-aromatic carbocyclylsulfinyl", "substituted or unsubstituted aromatic carbocyclylsulfinyl", "substituted or unsubstituted aromatic heterocyclyl sulfinyl", "substituted or unsubstituted non-aromatic heterocyclyl sulfinyl", "substituted or unsubstituted non-aromatic carbocyclylsulfonyloxy", "substituted or unsubstituted aromatic carbocyclylsulfonyloxy", "substituted or unsubstituted aromatic heterocyclylsulfonyloxy", "substituted or unsubstituted non-aromatic heterocyclylsulfonyloxy", "substituted or unsubstituted non-aromatic carbocyclylcarbonyloxy", "substituted or unsubstituted aromatic carbocyclylcarbonyloxy", "substituted or unsubstituted aromatic heterocyclylcarbonyloxy", and "substituted or unsubstituted non-aromatic heterocyclylcarbonyloxy" include the following substituents. Hydrogen atom on the ring at arbitrary position(s) can be replaced with one or more group(s) selected from the following substituents.

Substituent:
alkyl, alkenyl, alkynyl, haloalkyl, haloalkenyl, halogen, hydroxy, carboxy, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azido, hydradino, ureido, amidino, guanidino, trialkylsilyl, alkyloxy, alkyloxyalkyloxy, alkenyloxy, alkynyloxy, haloalkyloxy, trialkylsilyloxy, cyanoalkyloxy, alkylcarbonyl, haloalkylcarbonyl, carbamoylalkylcarbonyl, alkenylcarbonyl, alkynylcarbonyl, monoalkylamino, dialkylamino, alkylsulfonyl, alkenylsulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, monoalkyloxycarbonylamino, dialkyloxycarbonylamino, alkenyloxycarbonyl, alkynyloxycarbonyl, alkylsulfanyl, alkylcarbonylsulfanyl, alkenylsulfanyl, alkynylsulfanyl, alkylsulfinyl, alkenylsulfinyl, alkynylsulfinyl, monoalkylcarbamoyl, mono(hydroxyalkyl)carbamoyl, dialkylcarbamoyl, hydroxycarbamoyl, cyanocarbamoyl, carboxyalkylcarbamoyl, mono(dialkylaminoalkyl)carbamoyl, di(dialkylaminoalkyl)carbamoyl, non-aromatic carbocyclylalkylcarbamoyl, non-aromatic carbocyclylcarbamoyl, non-aromatic heterocyclylalkylcarbamoyl, non-aromatic heterocyclylcarbamoyl, monoalkyloxycarbamoyl, dialkyloxycarbamoyl, monoalkyloxycarbonylalkylcarbamoyl, dialkyloxycarbonylalkylcarbamoyl, monoalkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, non-aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, non-aromatic carbocyclylcarbonyloxy, aromatic carbocyclylcarbonyloxy, aromatic heterocyclylcarbonyloxy, non-aromatic heterocyclylcarbonyloxy, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalkyl, non-aromatic carbocyclylalkyl, aromatic heterocyclylalkyl, non-aromatic heterocyclylalkyl, aromatic carbocyclylalkyloxy, non-aromatic carbocyclylalkyloxy, aromatic heterocyclylalkyloxy, non-aromatic heterocyclylalkyloxy, aromatic carbocyclylalkyloxycarbonyl, non-aromatic carbocyclylalkyloxycarbonyl, aromatic heterocyclylalkyloxycarbonyl, non-aromatic heterocyclylalkyloxycarbonyl, aromatic carbocyclylalkylamino, non-aromatic carbocyclylalkylamino, aromatic heterocyclylalkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, aromatic carbocyclylsulfonyl, non-aromatic carbocyclylsulfonyl, aromatic heterocyclylsulfonyl, non-aromatic heterocyclylsulfonyl, alkylsulfonyloxy, alkenylsulfonyloxy, alkynylsulfonyloxy, non-aromatic carbocyclylsulfonyloxy, aromatic carbocyclylsulfonyloxy, aromatic heterocyclylsulfonyloxy, non-aromatic heterocyclylsulfonyloxy, alkyloxycarbonylalkyl, carboxyalkyl, hydroxyalkyl, dialkylaminoalkyl, hydroxyalkyl, alkyloxyalkyl, aromatic carbocyclylalkyloxyalkyl, non-aromatic carbocyclylalkyloxyalkyl, aromatic heterocyclylalkyloxyalkyl, and non-aromatic heterocyclylalkyloxyalkyl.

Preferably, halogen, cyano, substituted or unsubstituted alkyl (a substituent group: halogen, hydroxy), substituted or unsubstituted alkenyl (a substituent group: halogen, hydroxy), substituted or unsubstituted alkynyl (a substituent group: halogen, hydroxy), substituted or unsubstituted non-aromatic carbocyclyl (a substituent group: halogen), substituted or unsubstituted aromatic carbocyclyl (a substituent group: halogen), substituted or unsubstituted non-aromatic heterocyclyl (a substituent group: halogen), substituted or unsubstituted aromatic heterocyclyl (a substituent group: halogen), substituted or unsubstituted alkyloxy (a substituent group: halogen, non-aromatic carbocyclyl, aromatic carbocyclyl), substituted or unsubstituted alkenyloxy (a substituent group: halogen, non-aromatic carbocyclyl, aromatic carbocyclyl), substituted or unsubstituted alkynyloxy (a substituent group: halogen, non-aromatic carbocyclyl, aromatic carbocyclyl), substituted or unsubstituted non-aromatic carbocyclyloxy (a substituent group: halogen, cyano, alkyl, alkylcarbonyl, alkyloxycarbonyl), substituted or unsubstituted aromatic carbocyclyl(a substituent group: halogen, cyano, alkyl, alkylcarbonyl, alkyloxycarbonyl), substituted or unsubstituted non-aromatic heterocyclyloxy (a substituent group: halogen, cyano, alkyl, alkylcarbonyl, alkyloxycarbonyl), substituted or unsubstituted aromatic heterocyclyloxy (a substituent group: halogen, cyano, alkyl, alkylcarbonyl, alkyloxycarbonyl), alkylsulfanyl, alkenylsulfanyl, alkynylsulfanyl, alkylsulfonyl, alkenylsulfonyl, alkynylsulfonyl, non-aromatic carbocyclylalkylamino, aromatic carbocyclylalkylamino, non-aromatic heterocyclylalkylamino, aromatic heterocyclylalkylamino, carbamoyl are exemplified.

More preferably, halogen, cyano, substituted or unsubstituted alkyl (a substituent group: halogen, hydroxy), alkenyl, non-aromatic carbocyclyl, aromatic carbocyclyl, substituted or unsubstituted non-aromatic heterocyclyl (a substituent group: halogen), aromatic heterocyclyl, substituted or unsubstituted alkyloxy (a substituent group: halogen, non-aromatic carbocyclyl, aromatic carbocyclyl), substituted or unsubstituted non-aromatic carbocyclyloxy (a substituent group: halogen, cyano, alkyl), substituted or unsubstituted aromatic carbocyclyl (a substituent group: halogen), substituted or unsubstituted non-aromatic heterocyclyloxy (a substituent group: alkylcarbonyl, alkyloxycarbonyl), aromatic heterocyclyloxy, alkylsulfanyl, alkylsulfonyl, non-aromatic carbocyclylalkylamino, carbamoyl are exemplified.

The above "substituted or unsubstituted non-aromatic carbocyclyl", "substituted or unsubstituted non-aromatic heterocyclyl", "substituted or unsubstituted fused aromatic carbocyclyl" and "substituted or unsubstituted fused aromatic heterocyclyl" can be substituted with "oxo". In this case, two hydrogen atoms on the carbon atom are replaced with =O group as follows:

[Formula 60]

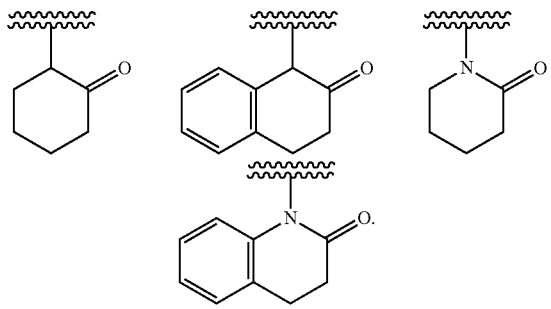

The non-aromatic carbocycle part and the non-aromatic heterocycle part in the above "substituted or unsubstituted non-aromatic heterocyclyl", "substituted or unsubstituted aromatic carbocyclyloxy", "substituted or unsubstituted non-aromatic heterocyclyloxy", "substituted or unsubstituted non-aromatic carbocyclylsulfanyl", "substituted or unsubstituted non-aromatic heterocyclylsulfanyl", "substituted or unsubstituted non-aromatic carbocyclylsulfinyl", "substituted or unsubstituted non-aromatic heterocyclyl sulfinyl", "substituted or unsubstituted non-aromatic carbocyclylsulfonyl", "substituted or unsubstituted non-aromatic heterocyclylsulfonyl", "substituted or unsubstituted non-aromatic carbocyclylsulfonyloxy", "substituted or unsubstituted non-aromatic heterocyclylsulfonyloxy", "substituted or unsubstituted non-aromatic carbocyclylcarbonyl", "substituted or unsubstituted non-aromatic heterocyclylcarbonyl", "substituted or unsubstituted non-aromatic carbocyclylcarbonyloxy", "substituted or unsubstituted non-aromatic heterocyclylcarbonyloxy", "substituted or unsubstituted non-aromatic carbocyclyloxycarbonyl", and "substituted or unsubstituted non-aromatic heterocyclyloxycarbonyl" can be substituted with "oxo" as described above.

Substituents of "substituted alkyl", "substituted alkenyl" and "substituted alkynyl" include hydroxy, halogen, dihalogen, trihalogen, non-aromatic carbocyclyl, substituted non-aromatic carbocyclyl (a substituent: halogen, cyano, alkyl), aromatic carbocyclyl, substituted aromatic carbocyclyl (a substituent: halogen, cyano, alkyl), non-aromatic heterocyclyl, substituted non-aromatic heterocyclyl (a substituent: halogen, cyano, alkyl), aromatic heterocyclyl, substituted aromatic heterocyclyl (a substituent: halogen, cyano, alkyl) and the like.

Substituents of "substituted alkyl" in $R^{x2}$ include halogen, dihalogen, trihalogen, non-aromatic carbocyclyl, substituted non-aromatic carbocyclyl (a substituent: halogen, cyano, alkyl) and the like.

Substituents of "substituted non-aromatic carbocyclyl", "substituted non-aromatic heterocyclyl", "substituted aromatic carbocyclyl" and "substituted aromatic heterocyclyl" include halogen, dihalogen and the like.

Substituents of "substituted non-aromatic heterocyclyl" of $R^{x3}$ include halogen, dihalogen and the like.

Substituents of "substituted alkyloxy", "substituted alkenyloxy" and "substituted alkynyloxy" include halogen, dihalogen, trihalogen, cyano, non-aromatic carbocyclyl, halo non-aromatic carbocyclyl, dihalo non-aromatic carbocyclyl, aromatic carbocyclyl and the like.

Substitutents of "substituted alkyloxy" in $R^{x3}$ include halogen, dihalogen, trihalogen, cyano, non-aromatic carbocyclyl, halo non-aromatic carbocyclyl, dihalo non-aromatic carbocyclyl, aromatic carbocyclyl and the like.

Substituents of "substituted non-aromatic carbocyclyloxy", "substituted non-aromatic heterocyclyloxy", "substituted aromatic carbocyclyloxy" and "substituted aromatic heterocyclyloxy" include halogen, alkyl, hydroxy, hydroxy non-aromatic carbocyclyl, alkylcarbonyl, alkyloxycarbonyl and the like.

Substituents of "substituted non-aromatic heterocyclyloxy" in $R^{x3}$ include alkylcarbonyl, alkyloxycarbonyl and the like.

Substituents of "substituted aromatic carbocyclyloxy" in $R^{x3}$ include halogen, alkyl, hydroxy, hydroxy non-aromatic carbocyclyl and the like.

Substituents of "substituted amino" include non-aromatic carbocyclylalkyl and the like.

Substituents of "substituted amino" in $R^{x3}$ include non-aromatic carbocyclylalkyl and the like.

Substituents of "substituted alkylcarbonyl", "substituted alkenylcarbonyl" and "substituted alkynylcarbonyl" include halogen, dihalogen, cyano, hydroxy and the like.

Substitutents of "substituted alkylcarbonyl" in $R^4$ include halogen, dihalogen, cyano, hydroxy and the like.

Substituents of "substituted carbamoyl" and "substituted sulfamoyl" include alkyl, dialkyl and the like.

Substituents of "substituted carbamoyl" in $R^4$ include alkyl, dialkyl and the like.

Preferable embodiments of $R^1$, $R^2$, $R^3$, $R^4$, $-L^1-$, $-L^2-$ and ring A in the compounds of formula (I) are described below.

[Formula 61]

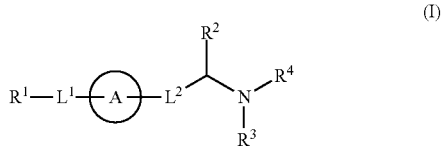

The following possible combinatorial compounds are preferable.

$R^1$ includes substituted or unsubstituted fused aromatic heterocyclyl represented by the following formula:

[Formula 62]

wherein ring B is 5-membered ring, ring C is 6-membered ring.

A preferable embodiment of $R^1$ is a group represented by the formula:

[Formula 63]

wherein
$X^1$ is N or $C(R^{x1})$,
$X^2$ is N or $C(R^{x2})$,
$X^3$ is N or $C(R^{x3})$,
$X^4$ is N or $C(R^{x4})$,
$X^5$ is $N(R^{x5})$, O or S,
$X^6$ is N or $C(R^{x6})$,
$R^{x1}$, $R^{x2}$, $R^{x3}$, $R^{x4}$, $R^{x5}$ and $R^{x6}$ are each independently hydrogen, halogen, hydroxy, carboxy, cyano, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy, substituted or unsubstituted aromatic heterocyclyloxy, substituted or unsubstituted alkylsulfanyl, substituted or unsubstituted or unsubstituted alkenylsulfanyl, substituted or unsubstituted alkynylsulfanyl, substituted or unsubstituted non-aromatic carbocyclylsulfanyl, substituted or unsubstituted aromatic carbocyclylsulfanyl, substituted or unsubstituted non-aromatic heterocyclylsulfanyl, substituted or unsubstituted aromatic heterocyclylsulfanyl, substituted or unsubstituted amino, substituted or unsubstituted carbamoyl, substituted or unsubstituted sulfamoyl, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl, substituted or unsubstituted aromatic heterocyclylsulfonyl, or substituted or unsubstituted sulfamoyl.

Another preferable embodiment of $R^1$ is a group represented by the formula:

[Formula 64]

wherein
$X^1$ is $C(R^{x1})$,
$X^2$ is N or $C(R^{x2})$,
$X^3$ is $C(R^{x3})$,
$X^4$ is $C(R^{x4})$,
$X^5$ is $N(R^{x5})$, O or S,
$X^6$ is N or $C(R^{x6})$,
$R^{x1}$, $R^{x2}$, $R^{x3}$, $R^{x4}$, $R^{x5}$ and $R^{x6}$ are each independently hydrogen, halogen, hydroxy, carboxy, cyano, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy, substituted or unsubstituted aromatic heterocyclyloxy, substituted or unsubstituted alkylsulfanyl, substituted or unsubstituted alkenylsulfanyl, substituted or unsubstituted alkynylsulfanyl, substituted or unsubstituted non-aromatic carbocyclylsulfanyl, substituted or unsubstituted aromatic carbocyclylsulfanyl, substituted or unsubstituted non-aromatic heterocyclylsulfanyl, substituted or unsubstituted aromatic heterocyclylsulfanyl, substituted or unsubstituted amino, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl, substituted or unsubstituted aromatic heterocyclylsulfonyl, or substituted or unsubstituted sulfamoyl.

Furthermore, another preferable embodiment of $R^1$ is a group represented by the formula:

[Formula 65]

wherein
$X^1$ is $C(R^{x1})$,
$X^2$ is N or $C(R^{x2})$,
$X^3$ is $C(R^{x3})$,
$X^4$ is $C(R^{x4})$, $X^5$ is $N(R^{x5})$, O or S,
$X^6$ is N,
$R^{x1}$, $R^{x2}$, $R^{x3}$, $R^{x4}$ and $R^{x5}$ are each independently hydrogen, halogen, hydroxy, carboxy, cyano, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy, or substituted or unsubstituted aromatic heterocyclyloxy.

Furthermore, another preferable embodiment of $R^1$ is a group represented by the formula:

[Formula 66]

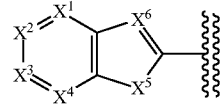

wherein
$X^1$ is $C(R^{x1})$,
$X^2$ is N or $C(R^{x2})$,
$X^3$ is $C(R^{x3})$,
$X^4$ is $C(R^{x4})$,
$X^5$ is $N(R^{x5})$,
$X^6$ is N,
$R^{x1}$ is hydrogen, halogen, cyano, substituted or unsubstituted alkyl, substituted or unsubstituted non-aromatic carbocyclyl, substituted or unsubstituted aromatic carbocyclyl or substituted or unsubstituted alkyloxy,
$R^{x2}$ is hydrogen, halogen, substituted or unsubstituted alkyl, substituted or unsubstituted alkyloxy, substituted or unsubstituted non-aromatic carbocyclyloxy or substituted or unsubstituted non-aromatic heterocyclyloxy,
$R^{x3}$ is hydrogen, halogen, substituted or unsubstituted alkyl, substituted or unsubstituted alkenyl, substituted or unsubstituted non-aromatic carbocyclyl, substituted or unsubstituted non-aromatic heterocyclyl, substituted or unsubstituted aromatic heterocyclyl, substituted or unsubstituted alkyloxy, substituted or unsubstituted non-aromatic carbocyclyloxy, substituted or unsubstituted aromatic carbocyclyloxy, substituted or unsubstituted aromatic heterocyclyloxy, substituted or unsubstituted alkylsulfanyl, substituted or unsubstituted alkylsulfonyl or substituted or unsubstituted amino,
$R^{x4}$ is hydrogen, halogen, cyano, substituted or unsubstituted alkyl, substituted or unsubstituted non-aromatic carbocyclyl, substituted or unsubstituted aromatic carbocyclyl or substituted or unsubstituted carbamoyl,
$R^{x5}$ is hydrogen, substituted or unsubstituted alkyl or substituted or unsubstituted non-aromatic carbocyclyl.

Ring A is substituted or unsubstituted non-aromatic carbocycle, substituted or unsubstituted non-aromatic heterocycle, substituted or unsubstituted aromatic carbocycle or substituted or unsubstituted aromatic heterocycle.

A preferable embodiment of ring A is substituted or unsubstituted non-aromatic carbocycle or substituted or unsubstituted non-aromatic heterocycle.

A more preferable embodiment of ring A is substituted or unsubstituted cyclobutane, substituted or unsubstituted cyclohexane, substituted or unsubstituted tetrahydropyran, or substituted or unsubstituted dioxane.

Another preferable embodiment of ring A is substituted or unsubstituted cyclobutane, substituted or unsubstituted cyclohexane, substituted or unsubstituted tetrahydropyran, or substituted or unsubstituted dioxane.

A preferable embodiment of a group represented by "—$L^1$— ring A—$L^2$—" is any one of groups represented by the following formula:

[Formula 67]

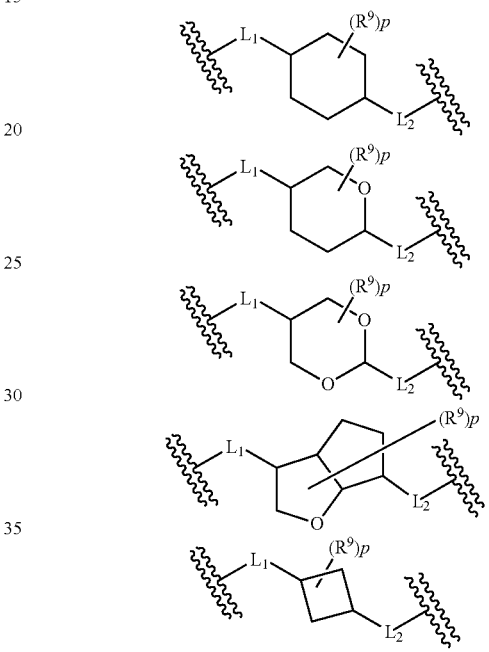

wherein $R^9$ is halogen, cyano, hydroxy, carboxy, oxo, substituted or unsubstituted alkyl, substituted or unsubstituted alkyloxy, or substituted or unsubstituted amino, p is an integer from 0 to 4.

—$L^1$— is —O—$(CR^6R^7)m$— or —$N(R^8)$—$(CR^6R^7)m$—, wherein the left bond binds to $R^1$, the right bond binds to ring A.

A preferable embodiment of —$L^1$— is —O—$(CR^6R^7)m$—, wherein the left bond binds to $R^1$, the right bond binds to ring A.

A preferable embodiment of —$L^1$— is —$N(R^8)$—$(CR^6R^7)m$—, wherein the left bond binds to $R^1$, the right bond binds to ring A.

Another preferable embodiment of —$L^1$— is —O— or —O—$(CR^6R^7)$—, wherein the left bond binds to $R^1$, the right bond binds to ring A.

Another preferable embodiment of —$L^1$— is —NH— or —NH—$(CR^6R^7)$—, wherein the left bond binds to $R^1$, the right bond to ring A.

More preferable embodiment of —$L^1$— is —O—.

Another more preferable embodiment of —$L^1$— is —NH—.

—$L^2$— is —O—$(CR^6R^7)n$—, —O—$CR^6$=$CR^7$— or —$(CR^6R^7)n$—, wherein the left bond binds to ring A, the right bond binds to a group represented by the following formula:

[Formula 68]

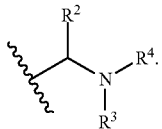

A preferable embodiment of —L$^2$— is —O—(CR$^6$R$^7$)n— or —(CR$^6$R$^7$)n—, wherein the left bond binds to ring A, the right bond binds to a group represented by the following formula:

[Formula 69]

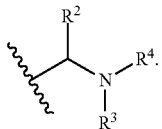

Another preferable embodiment of —L$^2$— is —O—(CR$^6$R$^7$)n—, wherein the left bond binds to ring A, the right bond bind to a group represented by the following formula:

[Formula 70]

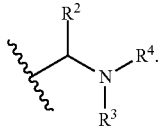

Another preferable embodiment of —L$^2$— is —(CR$^6$R$^7$)n—, wherein the left bond binds to ring A, the right bond binds to a group represented by the following formula:

[Formula 71]

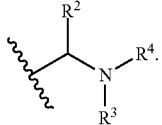

More preferable embodiment of —L$^2$— is —O—(CR$^6$R$^7$)—, wherein the left bond binds to ring A, the right bond binds to a group represented by the following formula:

[Formula 72]

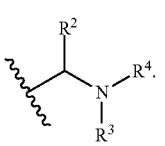

Another more preferable embodiment of —L$^2$— is —(CR$^6$R$^7$)$_2$—, wherein the left bond binds to ring A, the right bond binds to a group represented by the following formula:

[Formula 73]

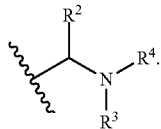

m is each independently an integer of 0, 1, 2 or 3.
A preferable embodiment of m is each independently 0 or 1.
Another preferable embodiment of m is 0.
n is each independently an integer of 1, 2 or 3.
A preferable embodiment of n is each independently 1 or 2.
Another preferable embodiment of n is 1.
Another preferable embodiment of n is 2.
R$^6$ is each independently hydrogen, halogen, cyano, substituted or unsubstituted alkyl, substituted or unsubstituted alkenyl, or substituted or unsubstituted alkynyl.
A preferable embodiment of R$^6$ is each independently hydrogen, halogen, or substituted or unsubstituted alkyl.
Another preferable embodiment of R$^6$ is each independently hydrogen.
p is an integer from 0 to 4.
A preferable embodiment of p is an integer from 0 to 2.
Another preferable embodiment of p is 0.
R$^7$ is each independently hydrogen, halogen, cyano, substituted or unsubstituted alkyl, substituted or unsubstituted alkenyl, or substituted or unsubstituted alkynyl.
A preferable embodiment of R$^7$ is each independently hydrogen, halogen, or substituted or unsubstituted alkyl.
Another preferable embodiment of R$^7$ is hydrogen.
R$^8$ is hydrogen or substituted or unsubstituted alkyl.
A preferable embodiment of R$^8$ is hydrogen or methyl.
Another preferable embodiment of R$^8$ is hydrogen.
R$^2$ is substituted or unsubstituted alkyl.
A preferable embodiment of R$^2$ is substituted or unsubstituted methyl.
Another preferable embodiment of R$^2$ is methyl, hydroxymethyl, or halomethyl.
R$^3$ is hydrogen or substituted or unsubstituted alkyl.
A preferable embodiment of R$^3$ is hydrogen.
R$^4$ is substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl, substituted or unsubstituted aromatic heterocyclylsulfonyl, or substituted or unsubstituted sulfamoyl.

A preferable embodiment of $R^4$ is substituted or unsubstituted alkylcarbonyl, substituted or unsubstituted alkenylcarbonyl, substituted or unsubstituted aromatic heterocyclylcarbonyl, substituted or unsubstituted alkyloxycarbonyl, substituted or unsubstituted carbamoyl, substituted or unsubstituted alkylsulfonyl, or substituted or unsubstituted sulfamoyl.

Another preferable embodiment of $R^4$ is substituted or unsubstituted alkylcarbonyl, substituted or unsubstituted aromatic heterocyclylcarbonyl, substituted or unsubstituted alkyloxycarbonyl, substituted or unsubstituted carbamoyl, substituted or unsubstituted alkylsulfonyl, or substituted or unsubstituted sulfamoyl.

Another more preferable embodiment of $R^4$ is methylcarbonyl, hydroxymethyl carbonyl, monohalomethylcarbonyl, dihalomethylcarbonyl, trihalomethylcarbonyl, cyanomethylcarbonyl, cyanomethylcarbonyl, carbamoyloxymethylcarbonyl, pyrazolylcarbonyl, carbamoyl, methylcarbamoyl, methyloxycarbonylcarbamoyl, methyloxycarbonyl, or methylsulfonyl.

Another preferable embodiments of $R^1$, $R^2$, $R^3$, $R^4$, —$L^1$—, —$L^2$— and ring A in a compound represented by formula (I):

[Formula 74]

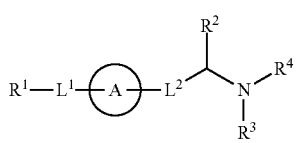

(I)

are shown as follow.
A compound of formula (I), or its pharmaceutically acceptable salt,
wherein,
$R^1$ is a group represented by the formula:

[Formula 75]

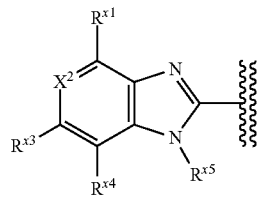

wherein $X^2$ is N or C(H),
$R^{x1}$ is hydrogen, halogen, or cyano,
$R^{x3}$ is haloalkyloxy, non-aromatic carbocyclyloxy, or non-aromatic heterocyclyloxy,
$R^{x4}$ is hydrogen or halogen,
$R^{x5}$ is alkyl,
ring A is a group represented by the formula:

[Formula 76]

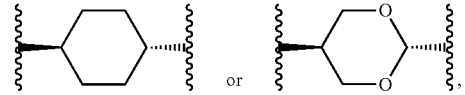

—$L^1$— is —O—,
—$L^2$— is —O—(CH$_2$)— or —(CH$_2$)$_2$—, wherein the left bond binds to ring A, and the right bond binds to a group represented by the formula:

[Formula 77]

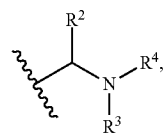

$R^2$ is alkyl or haloalkyl,
$R^3$ is hydrogen,
$R^4$ is alkylcarbonyl or carbamoyl,
provided that, the following compound is excluded,

[Formula 78]

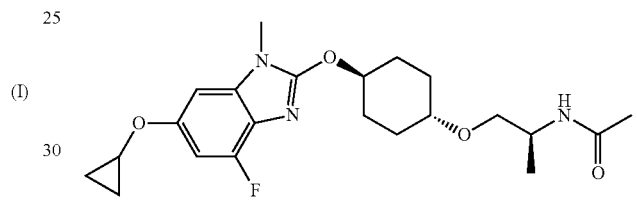

Especially the compound represented by the following formula:

[Formula 79]

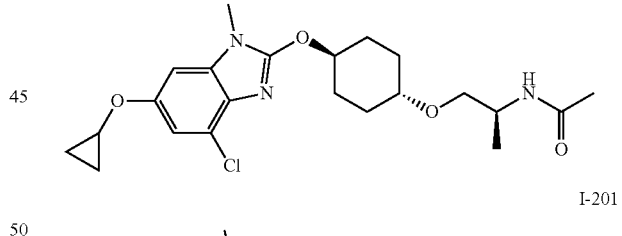

I-200

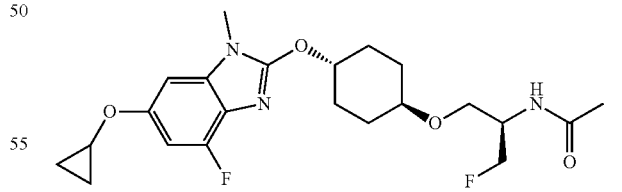

I-201

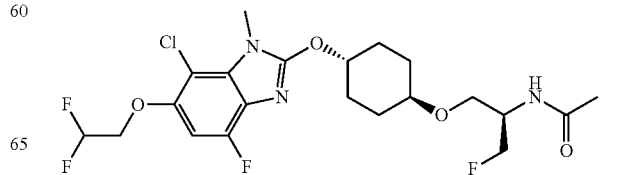

I-205

-continued

[Formula 80]

I-219
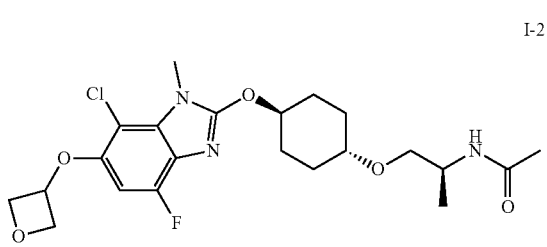

I-221
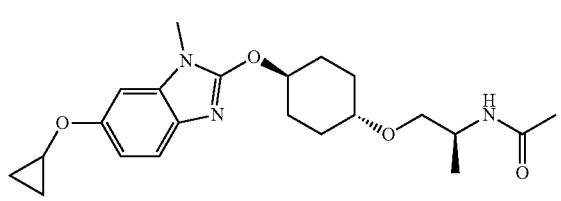

I-222
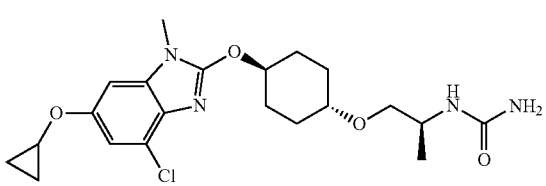

I-231
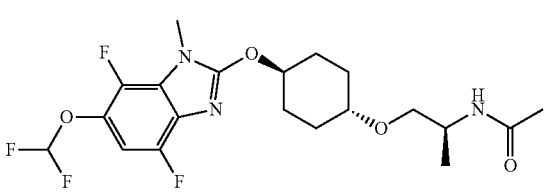

I-234
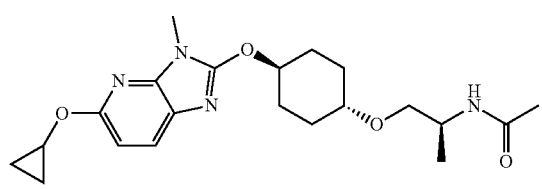

I-237
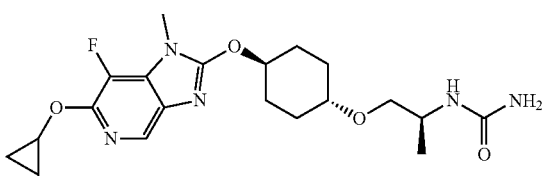

I-243
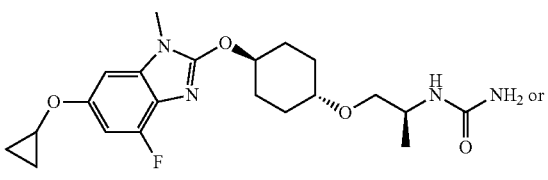

-continued

I-249
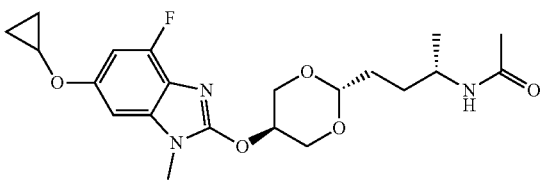

or its pharmaceutical acceptable salt is preferable.

"A disease associated with ACC2" includes metabolic syndrome, obesity, diabetes, insulin resistance, abnormal glucose tolerance, diabetic peripheral neuropathy, diabetic nephropathy, diabetic retinal disease, diabetic macroangiopathy, hyperlipidemia, hypertension, cardiovascular illness, arterial sclerosis, atherosclerotic cardiovascular disease, cardiac arrest, cardiac infarction, infectious disease, neoplasm and the like.

The compound of formula (I), (I'), and (I") are not limited to the specific isomer, include all possible isomers (for example, keto-enol isomer, imine-enamine isomer, diastereo isomer, enantiomer, rotamer and the like), racemates or mixture thereof, with the exception of a part represented by the chemical structure.

One or more hydrogen, carbon and/or other atoms of the compounds of formula (I), (I'), and (I") can be replaced by an isotope of the hydrogen, carbon, and/or other atoms. The examples of isotopes include isotopes of hydrogen, carbon, nitrogen, oxygen, phosphorous, sulfur, fluorine and chloride, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$, respectively. The compounds of formula (I), (I'), and (I") include compounds that substituted with the isotopes. And the compounds substituted with the isotopes are useful as medicine, and include radiolabeled forms of the compounds of formula (I), (I'), and (I") "radiolabeled", "radiolabeled form". The process for radiolabeling the compounds thereof to prepare the "radiolabeled form" is encompassed by the invention, is useful as a research and/or diagnostic tool in metabolism pharmacokinetic studies and in binding assays.

Radiolabeled compounds of formula (I), (I'), and (I") can be prepared by methods known in the art. For example, tritiated compounds of formula (I), (I'), and (I") can be prepared by introducing tritium into the particular compound of formula (I), (I'), and (I"), for example, by catalytic dehalogenation with tritium. This method may include reacting a suitably halogen-substituted precursor of a compound of formula (I), (I'), and (I") with tritium gas in the presence of a suitable catalyst such as Pd/C, in the presence or absence of a base. Other suitable methods for preparing tritiated compounds can be found in Filer, Isotopes in the Physical and Biomedical Sciences, Vol. 1, Labeled Compounds (Part A), Chapter 6 (1987). $^{14}C$-labeled compounds can be prepared by employing materials having a $^{14}C$ carbon.

Examples of "pharmaceutically acceptable salts" include salt such as a compound of formula (I), (I'), and (I") with alkaline metals (e.g.: lithium, sodium, potassium etc.), alkaline earth metals (e.g., calcium, barium etc.), magnesium, transition metals (e.g. zinc, iron etc.), ammonium, organic bases (e.g. trimethylamine, triethylamine, dicyclohexylamine, ethanolamine, diethanolamine, triethanolamine, meglumine, diethanolamine, ethylenediamine, pyridine, picoline, quinolone etc.) and amino acids, and salts with inorganic acids (e.g. hydrochloric, sulfuric acid, nitric acid, carbonic acids, hydrobromic acid, phosphoric acid, hydroiodic acid etc.), or organic acids (e.g. formic acid, acetic acid, propionic acid, trifluoroacetic acid, citric acid, lactic acid, tartaric acid, oxalic acid, maleic acid, fumaric acid, maldelic acid, glutaric acid, malic acid, benzoic acid, phthalic acid, ascorbic acid, benzenesulfonic acid, p-toluenesulfonic acid, methanesulfonic acid, ethanesulfonic acid etc.). Especially, preferable examples are salts with hydrochloric acid, sulfuric acid, phosphoric acid, tartaric acid, or methanesulfonic acid. These salts may be formed by a routine method.

The compounds of the invention of formula (I), (I'), and (I") or its pharmaceutically acceptable salts can be prepared in a form of solvate thereof (for example, hydrate etc.) and/or its crystal polymorph, the present invention includes such solvate and polymorph. Any number of solvent molecules can be coordinated to form such solvate to the compounds of formula (I), (I'), and (I"). When the compounds of formula (I), (I'), and (I") or its pharmaceutically acceptable salt are left in the atmosphere, it can absorb moisture to attach the absorbed water or to form the hydrate. Also, the compounds of formula (I), (I'), and (I") or its pharmaceutically acceptable salt can be recrystallized to form the crystal polymorph.

The compounds of the invention of formula (I), (I'), and (I") or its pharmaceutically acceptable salts can be formed the prodrug, the present invention includes the various prodrug. The prodrug is the derivatives of the compounds for this invention having the group decomposed by chemical or metabolic method, and are compounds that prepared by solvolysis or under physiological condition, and are compounds having an activity in vivo. The prodrug includes compounds converted to the compounds for this invention of formula (I), (I'), and (I") by oxidation, reduction or hydrolysis under physiological conditions in vivo and compounds hydrolyzed to the compounds for this invention of formula (I), (I'), and (I") by gastric acid and the like. The methods for selecting suitable prodrug derivatives and preparing thereof can be found in filer, for example, Design of Prodrugs, Elsevier, Amsterdam 1985. The prodrug may have an activity in its own.

When the compounds of the invention of formula (I), (I'), and (I") or its pharmaceutically acceptable salt has hydroxy, for example, it is reacted with the suitable acyl halide, the suitable acid anhydride, the suitable sulfonyl chloride, the suitable sulfonyl anhydride and mixed anhydride or with condensation agent to afford the prodrug such as the acyloxy derivatives or sulfonyloxy derivatives.

Examples of the prodrug are $CH_3COO-$, $C_2H_5COO-$, t-BuCOO—, $C_{15}H_{31}COO-$, PhCOO—, (m-NaOOCPh)COO—, $NaOOCCH_2CH_2COO-$, $CH_3CH(NH_2)COO-$, $CH_2N(CH_3)_2COO-$, $CH_3SO_3-$, $CH_3CH_2SO_3-$, $CF_3SO_3-$, $CH_2FSO_3-$, $CF_3CH_2SO_3-$, p-$CH_3$—O—$PhSO_3-$, $PhSO_3-$, p-$CH_3PhSO_3-$ and the like.

The general procedures for producing the compounds of the present invention are described as follows. Any starting materials and reaction reagents are commercially available or can be prepared using compounds which are commercially available by techniques and procedures readily available to one skilled in the art.

For example, the compound of the present invention represented by formula (I), (I') and (I") can be prepared by the following synthetic route.

A method for preparing the compound b2

[Formula 81]

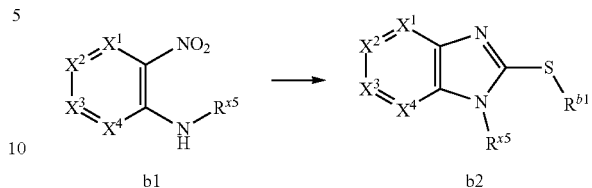

wherein $X^1$ is N or $C(R^{x1})$,
$X^2$ is N or $C(R^{x2})$,
$X^3$ is N or $C(R^{x3})$,
$X^4$ is N or $C(R^{x4})$,
$R^{x1}$, $R^{x2}$, $R^{x3}$, $R^{x4}$ and $R^{x5}$ are each independently hydrogen, halogen, hydroxy, carboxy, cyano, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy, substituted or unsubstituted aromatic heterocyclyloxy, substituted or unsubstituted alkylsulfanyl, substituted or unsubstituted alkenylsulfanyl, substituted or unsubstituted alkynylsulfanyl, substituted or unsubstituted non-aromatic carbocyclylsulfanyl, substituted or unsubstituted aromatic carbocyclylsulfanyl, substituted or unsubstituted non-aromatic heterocyclylsulfanyl, substituted or unsubstituted aromatic heterocyclylsulfanyl, substituted or unsubstituted amino, substituted or unsubstituted carbamoyl, substituted or unsubstituted sulfamoyl, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl, substituted or unsubstituted aromatic heterocyclylsulfonyl, or substituted or unsubstituted sulfamoyl, and $R^{b1}$ is substituted or unsubstituted alkyl.

The compound b2 can be obtained by reacting with 1,1'-thiocarbonyldiimidazole after reacting the solution of the compound b1 with a reductant in the presence of an acid.

Examples of the reaction solvent include ethanol, water, methanol and the like, and their mixed solvents can be used as well as the single solvent.

Examples of the reductant include iron, zinc and the like. The amount thereof may be 2 to 10 mole equivalents, preferably 3 to 5 mole equivalents, for 1 mole of the compound b1.

Examples of the acid include ammonium chloride, acetic acid, hydrochloric acid and the like. The amount thereof may be 2 to 10 mole equivalents, preferably 3 to 5 mole equivalents, for 1 mole of the compound b1.

The reaction temperature of the reaction with a reductant may be room temperature to 100° C., preferably room temperature to 80° C.

The reaction time of the reaction with a reductant may be 1 to 12 hour(s), preferably 3 to 6 hours.

The amount of 1,1'-thiocarbonyldiimidazole may be 1 to 3 mole equivalent(s), preferably 1 to 2 mole equivalent(s), for 1 mole equivalent of the compound b1.

The reaction temperature of the reaction with 1,1'-thiocarbonyldiimidazole may be 0° C. to 50° C., preferably 0° C. to room temperature.

The reaction time of reaction with 1,1'-thiocarbonyldiimidazole may be 0.5 to 6 hour(s), preferably 0.5 to 2 hour(s).

A method for preparing the compound b4

[Formula 82]

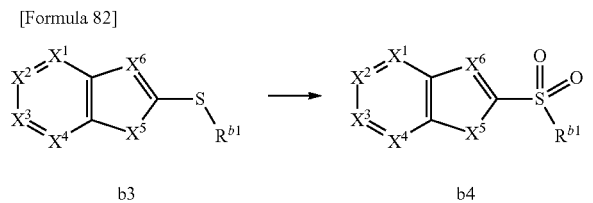

Wherein, $X^6$ is N or $C(R^{x6})$, $R^{x6}$ is hydrogen, halogen, hydroxy, carboxy, cyano, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy, substituted or unsubstituted aromatic heterocyclyloxy, substituted or unsubstituted alkylsulfanyl, substituted or unsubstituted alkenylsulfanyl, substituted or unsubstituted alkynylsulfanyl, substituted or unsubstituted non-aromatic carbocyclylsulfanyl, substituted or unsubstituted aromatic carbocyclylsulfanyl, substituted or unsubstituted non-aromatic heterocyclylsulfanyl, substituted or unsubstituted aromatic heterocyclylsulfanyl, substituted or unsubstituted amino, substituted or unsubstituted carbamoyl, substituted or unsubstituted sulfamoyl, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl, substituted or unsubstituted aromatic heterocyclylsulfonyl, or substituted or unsubstituted sulfamoyl. The other symbols are as defined above.

The compound b4 can be obtained by reacting a solution of the compound b3 with an oxidant.

Examples of the reaction solvent include dichloromethane, chloroform and the like, and their mixed solvents can be used as same as the single solvent.

Examples of the oxidant include m-chloroperbenzoic acid, hydrogen peroxide solution and the like. The amount of the oxidant may be 1 to 5 mole equivalent(s), preferably 1.5 to 2.5 mole equivalents, for 1 mole equivalent of the compound b3.

The reaction temperature may be 0° C. to room temperature, preferably room temperature.

The reaction time may be 0.5 to 12 hour(s), preferable 1 to 6 hour(s).

A method for preparing the compound b6

[Formula 83]

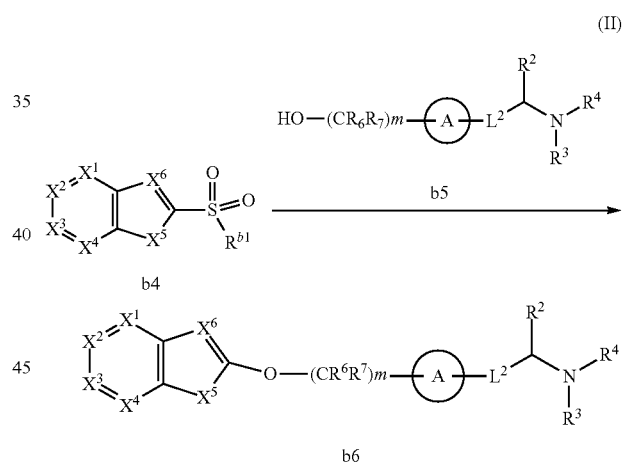

wherein ring A is substituted or unsubstituted non-aromatic carbocycle, substituted or unsubstituted non-aromatic heterocycle, substituted or unsubstituted aromatic carbocycle or substituted or unsubstituted aromatic heterocycle, —$L^2$— is —O—$(CR^6R^7)n$—, —O—$CR^6$=$CR^7$— or —$(CR^6R^7)n$—, $R^6$ and $R^7$ are each independently hydrogen, halogen, cyano, substituted or unsubstituted alkyl, substituted or unsubstituted alkenyl, or substituted or unsubstituted alkynyl, or $R^6$ and $R^7$ on the same carbon atom may be taken together with the carbon atom to form a ring, $R^8$ is hydrogen or substituted or unsubstituted alkyl, m is each independently an integer of 0, 1, 2 or 3, n is each independently an integer of 1, 2 or 3,
$R^2$ is substituted or unsubstituted alkyl,
$R^3$ is hydrogen or substituted or unsubstituted alkyl,
$R^4$ is substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl, substituted or unsubstituted aromatic heterocyclylsulfonyl, or substituted or unsubstituted sulfamoyl, $R^6$ and $R^7$ are each independently hydrogen, halogen, cyano, substituted or unsubstituted alkyl, substituted or unsubstituted alkenyl, or substituted or unsubstituted alkynyl, or $R^6$ and $R^7$ on the same carbon atom may be taken together with the carbon atom to form a ring, $R^8$ is hydrogen or substituted or unsubstituted alkyl, m is each independently an integer of 0, 1, 2 or 3, and the other symbols are as defined above.

The compound b6 can be obtained by reacting a solution of the compound b4 with the compound b5 in the presence of a base.

Examples of the reaction solvent include THF, DMF, dioxane and the like, and their mixed solvents can be used as same as the single solvent.

Examples of the base include potassium tert-butoxide, sodium hydride, potassium carbonate and the like. The amount of the base may be 2 to 5 mole equivalents, preferably 2 to 3 mole equivalents, for 1 mole equivalent of the compound b4.

The amount of the compound b5 may be 1 to 3 mole equivalent(s), preferably 1 to 1.5 mole equivalent(s), for 1 mole equivalent of the compound b4.

The reaction temperature may be 0° C. to room temperature, preferably room temperature.

The reaction time may be 0.5 to 6 hour(s), preferably 1 to 3 hour(s).

A method for preparing the compound b8

[Formula 84]

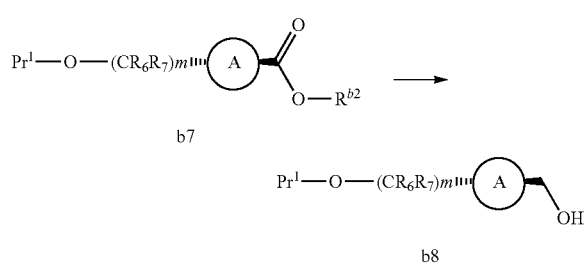

wherein $Pr^1$ is an alcohol-protecting group of alcohol (e.g., TBDPS etc.), $Rb^2$ is substituted or unsubstituted alkyl, and the other symbols are as defined above.

The compound b8 can be obtained by reacting a solution of the compound b7 with a reductant.

Examples of the reaction solvent include THF, methanol, ethanol and the like, and their mixed solvent may be used as same as the single solvent.

Examples of the reductant include sodium borohydride, lithium aluminum hydride and the like. The amount of the reductant may be 1 to 5 mole equivalent(s), preferably 2 to 4 mole equivalents, for 1 mole equivalent of the compound b7.

The reaction temperature may be −78° C. to room temperature, preferably 0° C. to room temperature.

The reaction time may be 0.5 to 24 hours, preferably 3 to 15 hours.

A method for preparing the compound b9

[Formula 85]

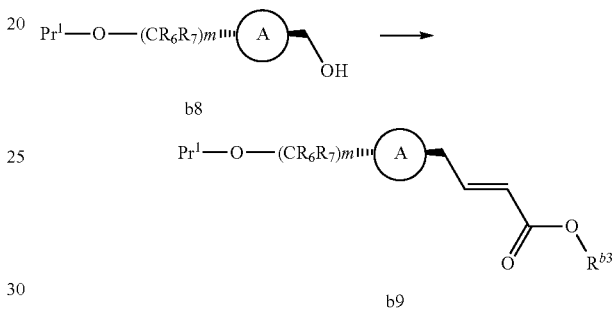

wherein $R^{b3}$ is substituted or unsubstituted alkyl, and the other symbols are as defined above.

Synthesis of the Compound b9

The compound b9 can be obtained by reacting a phosphorus compound in the presence of a base after reacting a solution of the compound b8 with an oxidant.

Examples of the reaction solvent include dichloromethane, chloroform and the like, their mixed solvents can be used as same as the single solvent.

Examples of the oxidant include Dess-Martin reagent, 2,2,6,6-tetramethyl piperidine-1-oxyl and the like. The amount of oxidant may be 1 to 3 mole equivalent(s), preferably 1 to 1.5 mole equivalent(s), for 1 mole equivalent of the compound b8.

The reaction temperature may be −78° C. to room temperature, preferably 0° C. to room temperature.

The reaction time may be 0.5 to 24 hour(s), preferably 1 to 6 hour(s).

Examples of the base include sodium hydride, potassium tert-butoxide, lithium diisopropylamine and the like. The amount of the base may be 1 to 3 mole equivalent(s), preferably 1 to 1.5 mole equivalent(s), for 1 mole equivalent of the compound b8.

Examples of the phosphorus compound include dialkylphosphonoalkyl acetate and the like. The amount of the phosphorus compound may be 1 to 3 mole equivalent(s), preferably 1 to 1.5 mole equivalent(s), for 1 mole equivalent of the compound b8.

Examples of the reaction solvent include THF, diethylether, dichloromethane and the like, and their mixed solvents can be used as same as the single solvent.

The reaction temperature may be −78° C. to reflux temperature of solvent, preferably 0° C. to room temperature.

The reaction time may be 0.5 to 12 hour(s), preferably 0.5 to 2 hour(s).

Synthesis of the Compound b10

[Formula 86]

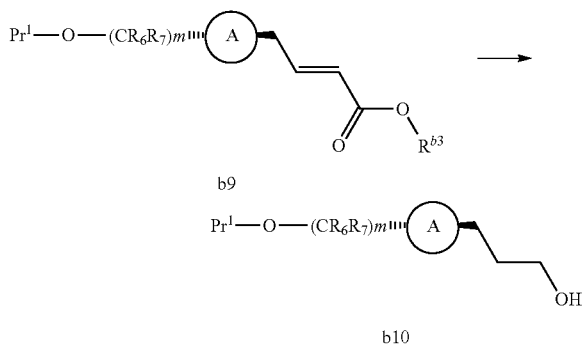

wherein, each symbols is as defined above.

The compound b10 can be obtained by reacting a solution of the compound b9 with a reductant.

Examples of the reaction solvent include THF, methanol, ethanol and the like, their mixed solvents can be used as same as the single solvent.

Examples of the reductant include sodium borohydride, lithium aluminum dydride and the like. The amount of the reductant may be 1 to 5 mole equivalent(s), preferably 2 to 4 mole equivalent(s), for 1 mole equivalent of the compound b9.

The reaction temperature may be −78° C. to room temperature, preferably 0° C. to room temperature.

The reaction time may be 0.5 to 24 hour(s), preferably 3 to 15 hours.

Synthesis of the Compound b111

[formula 87]

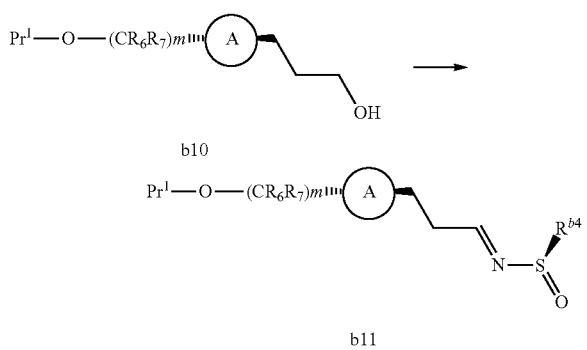

wherein $R^{b4}$ is substituted or unsubstituted alkyl, and the other symbols are as defined above.

The compound b11 can be obtained by reacting with sulfineamide compound in the presence of Lewis acid after reacting the compound b10 with an oxidant.

Examples of the reaction solvent include dichloromethane, chloroform and the like, and their mixed solvents can be used as same as the single solvent.

Examples of the oxidant include Dess-Martic reagent, 2,2,6,6-tetramethyl piperidine 1-oxyl and the like. The amount of the oxidant may be 1 to 3 mole equivalent(s), preferably 1 to 1.5 mole equivalent(s), for 1 mole equivalent of the compound b10.

The reaction temperature may be −78° C. to room temperature, preferably 0° C. to room temperature.

The reaction time may be 0.5 to 24 hour(s), preferably 1 to 6 hour(s).

Examples of Lewis acid include titanium tetraethoxide, aluminum chloride and the like. The amount of the Lewis acid may be 1 to 5 mole equivalent(s), preferably 1 to 1.5 mole equivalent(s), for 1 mole equivalent of the compound b10.

(R)-tert-butyl sulfineamide can be used in an amount of 1 to 2 mole equivalent(s), preferably 1 to 1.5 mole equivalent(s), for 1 mole equivalent of the compound b10.

Examples of the reaction solvent include toluene, THF, dichloromethane and the like, and their mixed solvents can be used as same as the single solvent.

The reaction temperature may be room temperature to 100° C., preferably room temperature to 80° C.

The reaction time may be 0.5 to 24 hour(s), preferably 0.5 or 3 hour(s).

Synthesis of the Compound b12

[Formula 88]

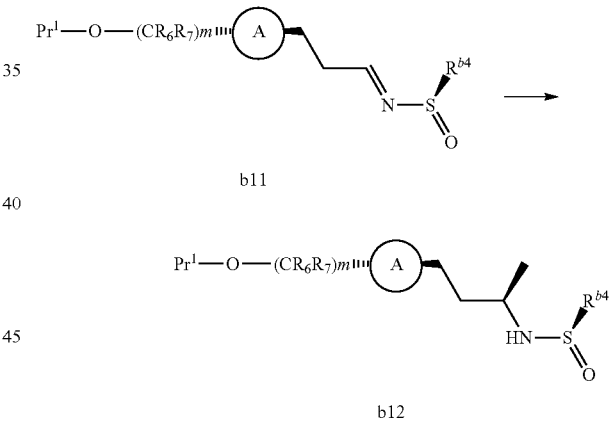

wherein, each symbols is as defined above.

The compound b12 can be obtained by reacting the compound b11 with an organic metallic reagent.

Examples of the reaction solvent include toluene, THF, dichloromethane and the like, and their mixed solvents can be used as same as the single solvent.

Examples of the organic metallic reagent include alkylmagnesium halide, alkyllithium, alkylsodium and the like. The amount of the organic metallic reagent may be 1 to 6 mole equivalent(s), preferably 1 to 4 mole equivalent(s), for 1 mole equivalent of the compound b11.

The reaction temperature may be 0° C. to 100° C., preferably 0° C. to room temperature.

The reaction time may be 1 to 24 hour(s), preferably 1 to 6 hour(s).

Synthesis of the Compound b13

[Formula 89]

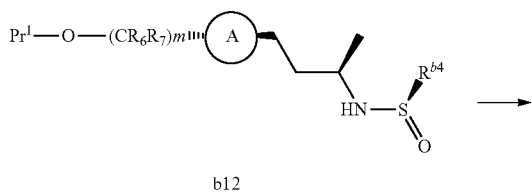

b12 b13 wherein, $R^{b5}$ is substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, or substituted or unsubstituted aromatic heterocyclyl, and the other symbols are as defined above.

The compound b13 can be obtained by reacting with an acylating agent after reacting the compound b12 with an acid.

Examples of the reaction solvent include 1,4-dioxane, THF, methanol and the like, and their mixed solvents can be used as same as the single solvent.

Examples of the acid include hydrochloric acid, TFA and the like. The amount of the acid may be 1 to 10 mole equivalent(s), preferably 3 to 5 mole equivalents, for 1 mole equivalent of the compound b12.

The reaction temperature may be 0° C. to 50° C., preferably 0° C. to room temperature.

The reaction time may be 0.5 to 24 hour(s), preferably 1 to 15 hour(s).

Examples of the acylating agent include acid anhydride, acyl halide and the like. The amount of the acylating agent may be 1 to 5 mole equivalent(s), preferably 1 to 2 mole equivalent(s), for 1 mole equivalent of the compound b12.

The reaction temperature may be 0° C. to room temperature, preferably room temperature.

The reaction time may be 0.5 to 6 hour(s), preferably 0.5 to 2 hour(s).

Synthesis of the Compound b14

[Formula 90]

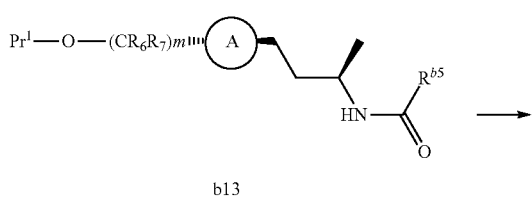

b13

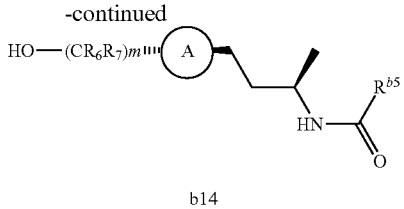

b14 wherein, each symbols is as defined above.

The compound b14 can be obtained by reacting the compound b13 with a deprotecting agent.

Examples of the reaction solvent include THF, dichloromethane, 1,4-dioxane and the like, and their mixed solvents can be used as same as the single solvent.

Examples of the deprotecting agent include tetrabutylammonium fluoride, hydrogen fluoride and the like. The amount of the deprotecting agent may be 1 to 5 mole equivalent(s), preferably 1 to 2 mole equivalent(s), for 1 mole equivalent of the compound b13.

The reaction temperature may be room temperature to 100° C., preferably room temperature to 50° C.

The reaction time may be 1 to 24 hour(s), preferably 3 to 5 hour(s).

A method for preparing the compound b16

[Formula 91]

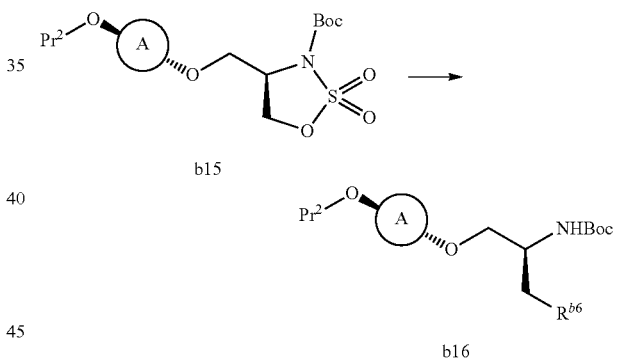

b15 b16 wherein $Pr^2$ is the hydroxyl-protecting group (e.g., benzyl, benzoyl etc.), and $R^{b6}$ is halogen, cyano, alkyloxy and the like.

Step 1

The compound b16 can be obtained by reacting the compound b15 with a nucleophile.

Examples of the reaction solvent include non-solvent, THF, DMF, 1,4-dioxane, NMP and the like, and their mixed solvent can be used as same as the single solvent.

Examples of the nucleophile include tetrabutylammoniumfluoride, sodium cyanide, sodium methoxide and the like. The amount of the nucleophile may be 1 to 5 mole equivalent(s), preferably 1 to 2 mole equivalent(s), for 1 mole equivalent of the compound b15.

The reaction temperature may be 0° C. to 150° C., preferably room temperature to 100° C.

The reaction time may be 1 to 24 hour(s), preferably 1 to 3 hour(s).

[Formula 92]

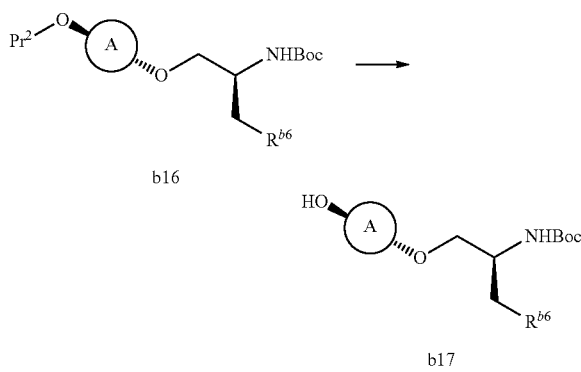

wherein, each symbol is as defined above.
Step 2
The solution of the compound b16 is catalytically reduced in the presence of a metallic catalyst to give the compound b17.

Examples of the reaction solvent include ethyl acetate, methanol, THF, 1,4-dioxane and the like, and their mixed solvents can be used as same as the single solvent.

Examples of the metallic catalyst include palladium-carbon, palladium hydrate, palladium chloride and the like. The amount of the metallic catalyst can be 0.001 to 1 mole equivalent, preferably 0.05 to 0.2 mole equivalent, for 1 mole equivalent of the compound b16.

The reaction temperature may be room temperature to reflux temperature of the solvent, preferably room temperature to 50° C.

The reaction time may be 0.5 to 48 hour(s), preferably 0.5 to 5 hour(s).

A method for preparing the compound b19

[Formula 93]

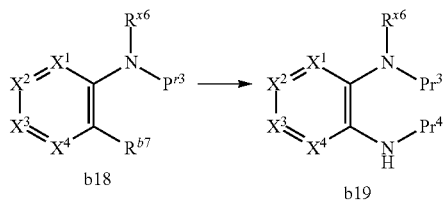

wherein $Pr^3$ and $Pr^4$ are each independently the amino-protecting group (e.g., benzyl, benzoyl etc.), and the other symbols are as defined above.

The compound b19 can be obtained by reacting the solution of the compound b18 with an amine in presence of a metallic catalyst, a ligand, and a base.

Examples of the reaction solvent may be toluene, DMF, 1,4-dioxane, NMP and the like, and their mixed solvent can be used as same as the single solvent.

Examples of the base may be sodium tert-butoxide, potassium tert-butoxide, sodium hydride, potassium phosphate and the like. The amount of the a base may be 1 to 5 mole equivalent(s), preferably 1 to 2 mole equivalent(s), for 1 mole equivalent of the compound b18.

Examples of the metallic catalyst may be tris(dibenzilidenacetone)palladium(0), palladium acetate and the like, the amount of the metallic catalyst may be 0.001 to 1 mole equivalent, preferably 0.05 to 0.5 mole equivalent, for 1 mole equivalent of the compound b18.

Examples of the ligand may be 2, 2'-bis(diphenylphosphino)-1,1'-binaphthyl, diphenylphosphinoferrocene, 2-dicyclohexylphosphino-2',4',6'-triisopropylbiphenyl and the like. The amount of the ligand may be 0.001 to 1 mole equivalent, preferably 0.1 to 0.5 mole equivalent, for 1 mole equivalent of the compound b18.

The reaction temperature may be 0° C. to reflux temperature of the solvent, preferably room temperature to 130° C.

The reaction time may be 0.5 to 24 hour(s), preferably 0.5 to 3 hour(s).

A method for preparing the compound b21

[Formula 94]

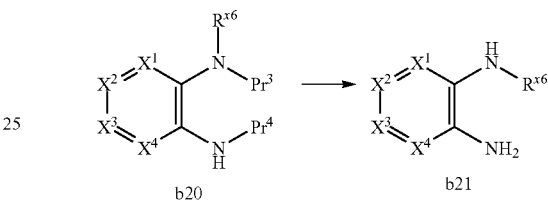

wherein, each symbol is as defined above.

The solution of the compound b20 is catalytically reduced in the presence of a metallic catalyst to give the compound b21.

Examples of the reaction solvent include methanol, ethanol, THF, dioxane, water and the like, and their mixed solvents can be used as same as the single solvent.

Examples of the metallic catalyst include palladium-carbon, palladium hydrate, platinum oxide and the like. The amount of the metallic catalyst may be 0.001 to 1 mole equivalent, preferably 0.05 to 0.5 mole equivalent, for 1 mole equivalent of the compound b20.

The reaction temperature may be 0° C. to reflux temperature of the solvent, preferably room temperature to 80° C.

The reaction time may be 0.5 to 24 hour(s), preferably 0.5 to 2 hour(s).

The compound of the present invention has ACC2 inhibitory activity. Moreover, the compound of the present invention can be a medicine which is reduced the side effect, because of having high ACC2 selectivity as against ACC1. Additionally, the compound of the present invention can be a medicine which is rescued the side effect, because of low cardiovascular or MBI risks. A pharmaceutical composition comprising the compound of the present invention is very useful for preventing or treating a disease associated with ACC2. Examples of the diseases associated with ACC2 means a disease induced by malonyl-CoA produced by ACC2 are metabolic syndrome, obesity, diabetes, insulin resistance, abnormal glucose tolerance, diabetic peripheral neuropathy, diabetic nephropathy, diabetic retinal disease, diabetic macroangiopathy, hyperlipidemia, hypertension, cardiovascular illness, arteriosclerosis, atherosclerosis, cardiac arrest, cardiac infarction, infectious disease, neoplasm and the like. A pharmaceutical composition comprising the compound of the present invention is very useful as a medicine for preventing or treating these disease.

A compound of the present invention has not only ACC2 inhibitory activity but also usefulness as a medicine and any or all good characters selected from the followings:

a) weak CYP enzyme (e.g., CYP1A2, CYP2C9, CYP2C19, CYP2D6, CYP3A4 etc.) inhibition.
b) good drug kinetics such as high bioavailability, appropriate clearance and the like.
c) high metabolic stability.
d) no irreversible CYP enzyme (e.g., CYP3A4) inhibition in the range of the concentration as a measuring condition described in the specification.
e) no mutagenicity.
f) low cardiovascular risk.
g) high water solubility.

The pharmaceutical composition of the invention can be administered orally or parenterally as an anti-obesity agent or anorectic agent. In the case of oral administration, it may be in any usual form such as tablets, granules, powders, capsules and the like. When the compound is parenterally administered, any usual form such as injections and the like is preferable. Oral administration is especially preferable because the compounds of the present invention show a high oral absorbability.

The pharmaceutical composition may be manufactured by mixing an effective amount of the compound of the present invention with various pharmaceutical additives suitable for the administration form, such as excipients, binders, moistening agents, disintegrants, lubricants and the like.

Although the dosage of the pharmaceutical composition of the invention as an anti-obesity agent or anorectic agent should be determined in consideration of the patient's age and body weight, the type and degree of diseases, the administration route and the like, a usual oral dosage for an adult is 0.05 to 100 mg/kg/day, preferable is 0.1 to 10 mg/kg/day. For parenteral administration, although the dosage highly varies with administration routes, a usual dosage is 0.005 to 10 mg/kg/day, preferably 0.01 to 1 mg/kg/day. The dosage may be administered in one to several divisions per day.

EXAMPLES

The present invention is further explained by the following examples, reference examples, preparation examples and test examples, which are not intended to limit the scope of this invention.

The abbreviations used in the present description stand for the following meanings.
Ac: acetyl
Bu: butyl
dba: dibenzylideneacetone
DMF: N,N-dimethylformamide
Et: ethyl
HATU: O-(7-azabenzotriazole-1-yl)-1,1,3,3-tetramethyl uronium hexafluorophosphate
Me: methyl
NMP: N-methyl-2-pyrrolidone
$Pd_2(dba)_3$: tris(dibenzylideneacetone)bispalladium
Ph: phenyl
Tf: trifluoromethanesulfonyl
THF: tetrahydrofuran
$Boc_2O$: di-tert-butyl dicarbonate
TBDPS: tert-butyldiphenylsilyl $^1$H NMR spectra of the examples were measured on 300 MHz or 400 MHz in ds-DMSO or $CDCl_3$.

"RT" in the examples or the tables represents "Retention Time" by LC/MS: Liquid Chromatography/Mass Spectrometry. LC/MS data of the compounds were measured under the following condition.

Method 1: Column: Gemini-NX (5 μm, i.d. 4.6×50 mm (Phenomenex)
Flow rate: 3.0 mL/min
UV detection wavelength: 254 nm
Mobile phase: [A] is 0.1% formic acid-containing aqueous solution, [B] is 0.1% formic acid-containing acetonitrile solution
Gradient: Linear gradient of 5% to 100% solvent [B] for 3.5 minutes was performed, and 100% solvent [B] was maintained for 0.5 minutes.

Method 2: Column: Shim-pack XR-ODS (2.2 μm, i.d. 50×3.0 mm (Shimadzu)
Flow late: 1.6 mL/min
UV detection wavelength: 254 nm
Mobile phase: [A] is 0.1% formic acid-containing aqueous solution, [B] is 0.1% formic acid-containing acetonitrile solution
Gradient: Linear gradient of 10% to 100% solvent [B] for 3 minutes was performed, and 100% solvent [B] was maintained for 0.5 minutes.

Method 3: Column: ACQUITY UPLC® BEH C18 (1.7 μm, i.d. 2.1×50 mm (Waters)
Flow rate: 0.55 mL/min
UV detection wavelength: 254 nm
Mobile phase: [A] is 0.1% formic acid-containing aqueous solution, and [B] is 0.1% formic acid-containing acetonitrile solution
Gradient: Linear gradient of 5% to 100% solvent [B] for 3 minutes was performed, and 100% solvent [B] was maintained for 0.5 minutes.

Method 4: Column: ACQUITY UPLC® BEH C18 (1.7 μm i.d. 2.1×50 mm (Waters)
Flow rate: 0.8 mL/min
UV detection wavelength: 254 nm
Mobile phase: [A] is 0.1% formic acid-containing aqueous solution, and [B] is 0.1% formic acid-containing acetonitrile solution
Gradient: Linear gradient of 5% to 100% solvent [B] for 3.5 minutes was performed, and 100% solvent [B] was maintained for 0.5 minutes.

Method 5: Column: Shim-pack XR-ODS (2.2 μm, i.d. 50×3.0 mm (Shimadzu)
Flow rate: 1.6 mL/min
UV detection wavelength: 254 nm
Mobile phase: [A] is 0.1% formic acid-containing aqueous solution, and [B] is 0.1% formic acid-containing acetonitrile solution
Gradient: Linear gradient of 10% to 100% solvent [B] for 8 minutes was performed, and 100% solvent [B] was maintained for 0.5 minutes.

Method 6: Column: ACQUITY UPLC® BEH C18 (1.7 μm i.d. 2.1×50 mm (Waters)
Flow rate: 0.55 mL/min
UV detection wavelength: 254 nm
Mobile phase: [A] is 0.1% formic acid-containing aqueous solution, [B] is 0.1% formic acid-containing acetonitrile solution
Gradient: Linear gradient of 5% to 100% solvent [B] for 8 minutes was performed, and 100% solvent [B] was maintained for 0.5 minutes.

Example 2 Preparation of Compound a18

Step 1 Preparation of Compound a9

[Formula 95]

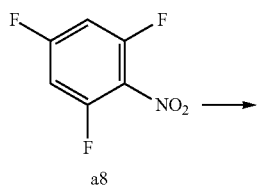

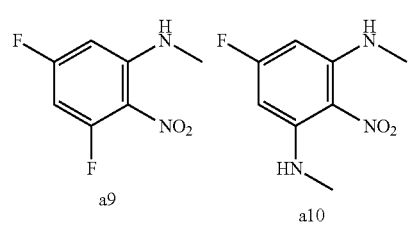

To the THF (20 ml) solution of Compound a8 (2 g, 11.29 mmol), trimethylamine (3.44 ml, 24.85 mmol) and methylamine (33% ethanol solution, 1.547 ml, 12.42 mmol) were added sequentially while cooling in ice. The reaction mixture was stirred at 0° C. for 10 hours. Brine (100 ml) was added to the reaction mixture, and the reaction mixture was extracted with ethyl acetate (100 ml) twice. The organic layer was dried over sodium sulfate. The solvent was condensed under reduced pressure to afford Compound a9 (2.2 g, 90% purity, 93%) as a mixture with Compound a10.

$^1$H-NMR (CDCl$_3$) δ: 2.97 (d, J=5.0 Hz, 3H), 6.18-6.28 (m, 2H), 7.64 (s, 1H).

Step 2 Preparation of Compound a11

[Formula 96]

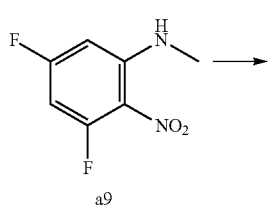

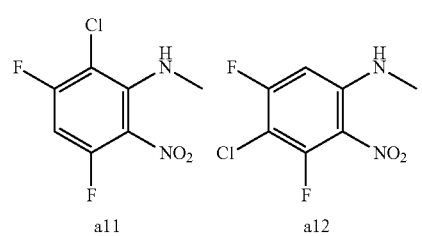

N-chlorosuccinimide (4.62 g, 34.6 mmol) was added to the acetonitrile (40 ml) solution of Compound a9 (5.92 g, 90% purity, 28.35 mmol) at 90° C., and the mixture was stirred for 1 hour. The reaction mixture was condensed under reduced pressure, and the insoluble matter was filtered. The residue was purified by silica gel column chromatography (hexane:ethyl acetate=5:1) to afford Compound a11 (2.25 g, 32%) as a yellow solid.

$^1$H-NMR (CDCl$_3$) δ: 2.94 (d, J=5.5 Hz, 3H), 5.23 (s, 1H), 6.43 (dd, J=9.9, 8.5 Hz, 1H).

Step 3 Preparation of Compound a13

[Formula 97]

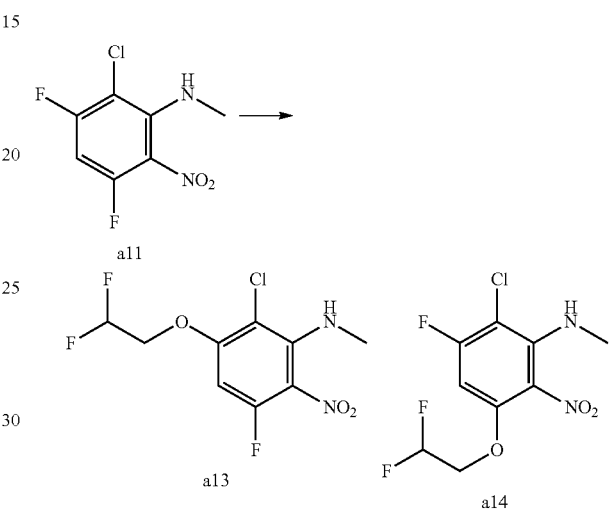

To the THF (20 mL) solution of Compound a11 (2.25 g, 10.11 mmol), 2,2-difluoroethanol (0.704 ml, 11.12 mmol), potassium carbonate (3.07 g, 22.24 mmol) and 18-crown-6 (8.02 g, 30.3 mmol) were added, and then the mixture was relaxed for 1 hour. Distilled water (30 ml) was added to the reaction mixture, and the reaction mixture was extracted with ethyl acetate (30 ml) twice. The organic layer was washed with distilled water (30 ml) twice, and brine (30 ml) once. The organic layer was dried over sodium sulfate, and the solvent was concentrated under reduced pressure. The residue was purified by silica gel column chromatography (hexane:ethyl acetate=5:1) to afford Compound a13 as the mixture with Compound a14 (1.33 g, a13:a14=2:1, 31%).

Step 4 Preparation of Compound a15

[Formula 98]

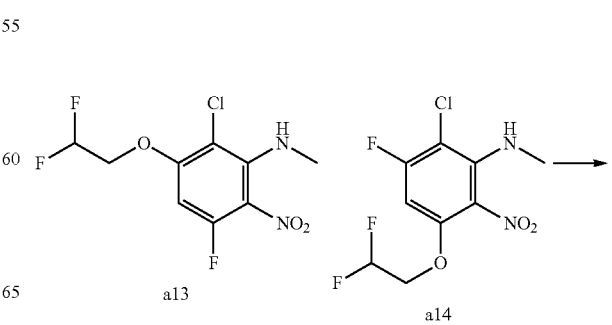

-continued

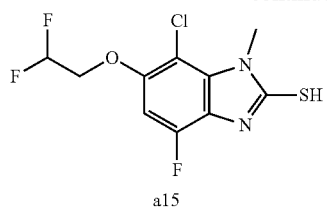

To the THF (20 ml) solution of the mixture of Compound a13 and Compound a14 (1.33 g, 4.67 mmol, a13:a14=2:1), 5% Pt/C (50% wet, 300 mg, 0.038 mmol) was added, and the mixture was stirred for 14 hours under hydrogen atmosphere. After filtered by celite, the solvent was concentrated under reduced pressure. Imidazole (0.636 g, 9.35 mmol) and 1,1'-thiocarbonyldiimidazole (0.999 g, 5.61 mmol) were added to the THF (20 ml) solution of the residue, and the mixture was refluxed for 2 hours. Distilled water was added to the reaction mixture, and the reaction mixture was extracted with ethyl acetate. The organic layer was washed with brine twice, and dried over sodium sulfate. The solvent was concentrated under reduced pressure. The residue was suspended with ethyl acetate, and filtered to afford Compound a15 as a mixture with Compound a16 (1.05 g, a15:a16=2:1, 50%).

Step 5 Preparation of Compound a17

[Formula 99]

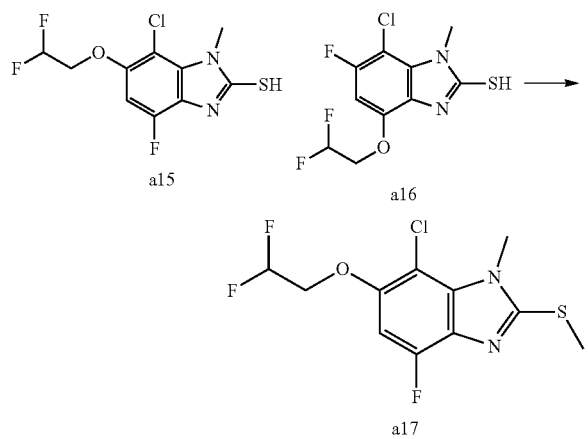

To the THF (10 ml) solution of the mixture of Compound a15 and Compound a16 (988 mg, 3.33 mmol, a15:a16=2:1), potassium carbonate (1013 mg, 7.33 mmol) and methyl iodide (0.229 ml, 3.66 mmol) were added, and the mixture was stirred at room temperature for 3 hours. After filtered by celite, the solvent was concentrated under reduced pressure. The residue was purified by silica gel column chromatography (hexane:ethyl acetate=3:1) to afford Compound a17 (581 mg, 56%) as a white solid.

$^1$H-NMR (CDCl$_3$) δ: 2.80 (s, 3H), 4.00 (s, 3H), 4.23 (td, J=13.0, 4.1 Hz, 2H), 6.14 (tt, J=55.0, 4.1 Hz, 1H), 6.68 (d, J=10.7 Hz, 1H).

Step 6 Preparation of Compound a18

[Formula 100]

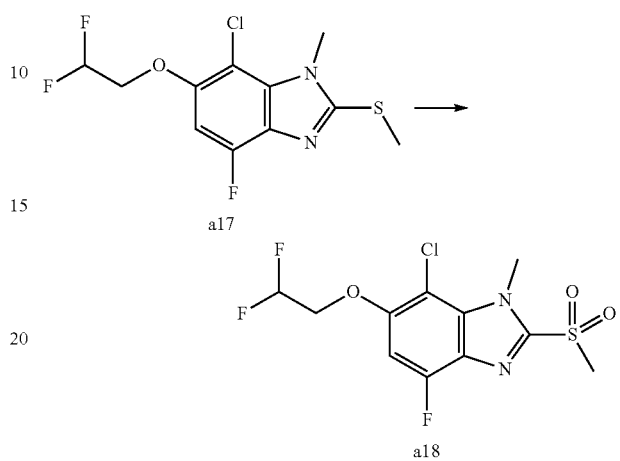

To the dichloromethane (10 ml) solution of Compound a17 (580 mg, 1.867 mmol), m-chloroperbenzoic acid (1012 mg, 4.11 mmol) was added, and the mixture was stirred at room temperature for 5 hours. Distilled water (50 ml) was added to the reaction mixture, and the reaction mixture was extracted with ethyl acetate (50 ml) twice. The organic layer was washed with 1 mol/L sodium hydrate aqueous solution (50 ml) five times and brine (50 ml) once. The organic layer dried over sodium sulfate, and then the solvent was concentrated under reduced pressure. The residue was suspended with ethyl acetate, and filtered to afford Compound a18 (640 mg, 100%) as a white solid.

$^1$H-NMR (CDCl$_3$) δ: 3.59 (s, 3H), 4.29 (td, J=12.8, 4.1 Hz, 2H), 4.45 (s, 3H), 6.16 (tt, J=54.8, 4.1 Hz, 1H), 6.85 (d, J=10.5 Hz, 1H).

Example 3 Preparation of Compound a26

Step 1 Preparation of Compound a20

[Formula 101]

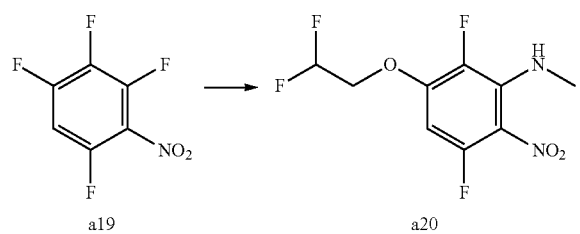

To the THF (150 ml) solution of Compound a19 (21.63 g, 111 mmol), potassium carbonate (33.7 g, 244 mmol) and methylamine (33% ethanol solution, 14.49 ml, 116 mmol) were sequentially added while cooling in ice, the mixture was stirred at 0° C. for 20 minutes. After filtered by celite, the solvent was concentrated under reduced pressure. The residue was diluted with ethyl acetate (200 ml). The organic layer was washed with brine (200 ml) three times, and dried with sodium sulfate. The solvent was concentrated under reduced pressure. To the THF (150 ml) solution of the obtained solid residue, potassium carbonate (30.6 g, 222 mmol), 2,2-difluoroethanol (7.02 ml, 111 mmol) and 18-crown-6 (35.2 g, 133 mmol) were added, and then the mixture was refluxed for 1 hour. After filtered by celite, the solvent was concentrated under reduced pressure. The residue was purified by silica gel chromatography (hexane:ethyl acetate=5:1) to afford Compound a20 (21.1 g, 71%) as a yellow solid.

$^1$H-NMR (CDCl$_3$) δ: 3.18 (dd, J=6.9, 5.4 Hz, 3H), 4.26 (td, J=12.7, 4.0 Hz, 2H), 5.93-6.28 (m, 2H), 6.83 (s, 1H).

Step 2 Preparation of Compound a21

[Formula 102]

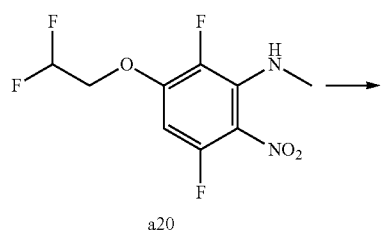

a20

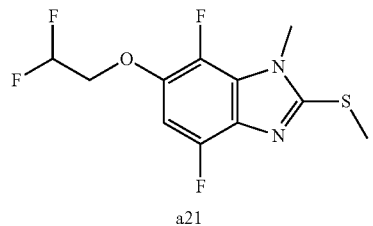

a21

To the ethanol (10 ml) suspension of Compound a21 (2.03 g, 7.57 mmol), THF (10 mL), zinc (2.475 g, 37.8 mmol) and ammonium chloride (2.025 g, 37.8 mmol) were added, and the mixture was stirred at room temperature for 2 hours. The reaction mixture was filtered by celite, and the solvent was concentrated under reduced pressure. To the THF (20 ml) solution of the obtained residue, imidazole (1.546 g, 22.71 mmol) and 1,1'-thiocarbonyldiimidazole (1.619 g, 9.08 mmol) were added, and the mixture was stirred for 1 hour while refluxing. Potassium carbonate (2.092 g, 15.14 mmol) and methyl iodide (0.568 ml, 9.08 mmol) were added to the reaction solution, and the mixture was further stirred at room temperature for 3 hours. The reaction mixture was filtered by celite, and the solvent was concentrated under reduced pressure. The residue was purified by silica gel column chromatography (hexane:ethyl acetate=2:1) to afford Compound a21 (1.83 g, 82%) as a white solid.

$^1$H-NMR (CDCl$_3$) δ: 2.80 (s, 3H), 3.84 (s, 3H), 4.25 (td, J=13.1, 4.1 Hz, 2H), 6.10 (tt, J=55.0, 4.1 Hz, 1H), 6.66 (dd, J=10.5, 6.0 Hz, 1H).

Step 3 Preparation of Compound a22

[Formula 103]

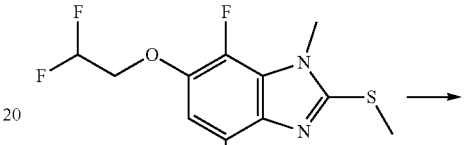

a21

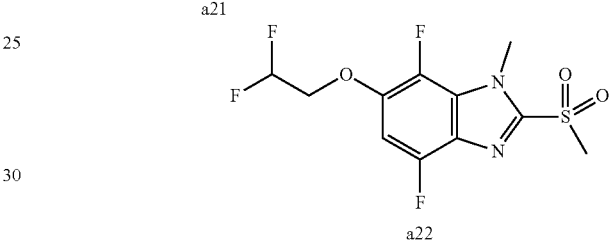

a22

To the dichloromethane (30 ml) solution of Compound a21 (1.8 g, 6.12 mmol), m-chloroperbenzoic acid (3.32 g, 13.46 mmol) was added, and the mixture was stirred at room temperature for 3 hours. Distilled water (200 ml) was added to the reaction mixture, and the reaction mixture was extracted with ethyl acetate (200 ml) twice. The organic layer was washed with 0.1 mol/L sodium hydrate aqueous solution (200 ml) five times, and brine (200 ml) once. The organic layer was dried over sodium sulfate, and the solvent was concentrated under reduced pressure. The residue was suspended with ethyl acetate and filtered to afford Compound a22 (2 g, 100%) as a white solid.

$^1$H-NMR (CDCl$_3$) δ: 3.58 (s, 3H), 4.29 (s, 3H), 4.32 (dt, J=4.0, 12.9 Hz, 2H), 6.12 (tt, J=54.8, 4.0 Hz, 1H), 6.84 (dd, J=10.3, 5.9 Hz, 1H).

Example 5 Preparation of Compound a43

[Formula 104]

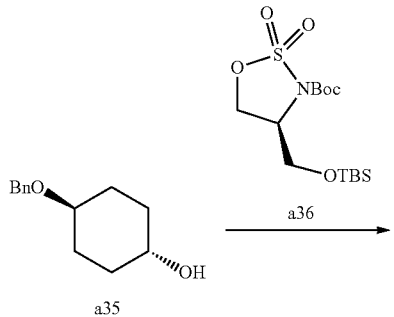

a35    a36

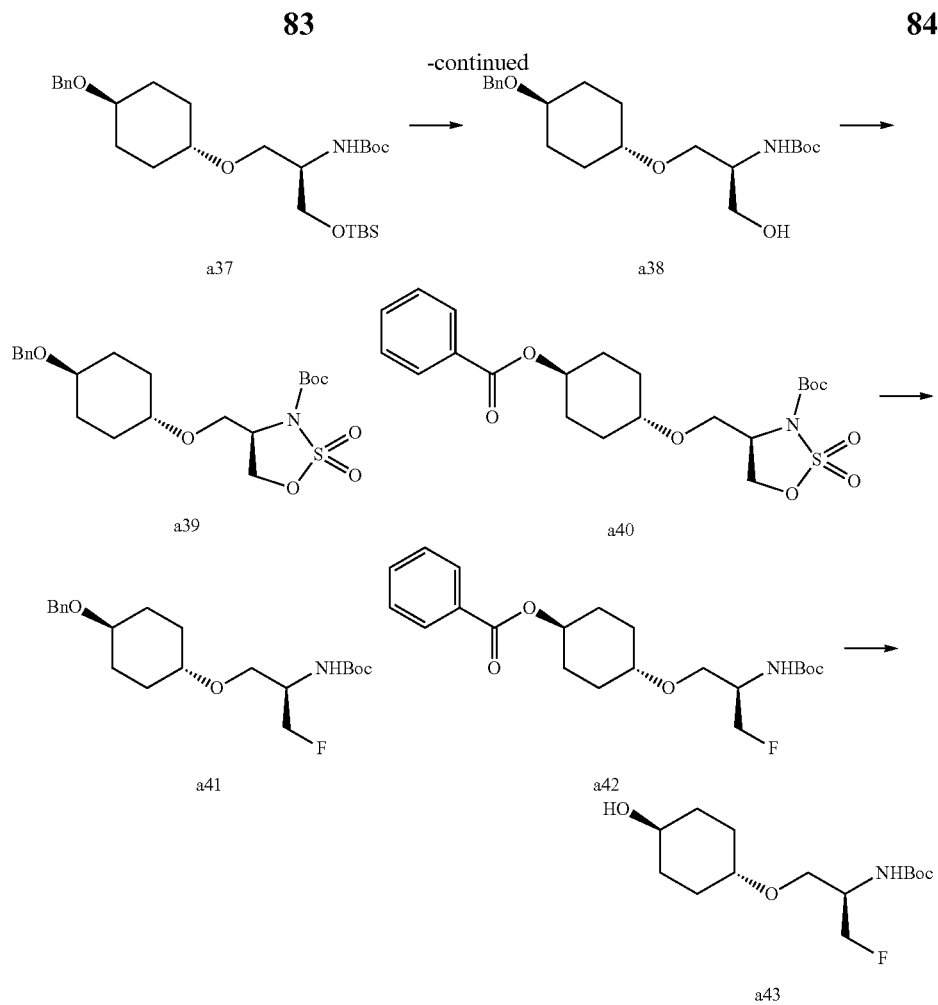

Step 1 Preparation of Compound a37

The DMF (13.5 ml) solution of Compound a35 (1.35 g, 6.55 mmol) was cooled with ice bath, sodium hydride (0.315 g, 7.87 mmol) was added thereto, and the mixture was stirred at same temperature for 30 minutes. Compound a36 (2.65 g, 7.21 mmol) was added thereto, and the reaction mixture was stirred at room temperature for 1 hour. Additionally, Compound a36 (0.482 g, 1.31 mmol) was added thereto, and the reaction mixture was stirred at 60° C. for 1 hour. After cooled to room temperature, 2 mol/L hydrochloric acid (13.1 mL, 26.2 mmol) was added thereto, and the reaction mixture was stirred at room temperature for 1 hour. The reaction mixture was neutralized with sodium carbonate, and then extracted with ethyl acetate. The organic layer was washed with water, and the solvent was concentrated under reduced pressure. The obtained residue was purified by silica gel chromatography (hexane-ethyl acetate) to afford Compound a37 (1.06 g, yield 33%).

[M+H]=494.20, Method Condition 3: retention time 3.35 min

Step 2 Preparation of Compound a38

Compound a37 (400 mg, 0.810 mmol) was dissolved in tetrabutylammoniumfluoride (1 mol/L, THF solution, 1 mL, 1.00 mmol). The reaction mixture was stirred at room temperature for 16 hours. The reaction solution was concentrated under reduced pressure, and the obtained residue was purified by silica gel column chromatography (hexane-ethyl acetate) to afford Compound a38 (272 mg, yield 89%).

[M+H]=380.15, Method Condition 3: retention time 2.29 min

Step 3 Preparation of a Mixture of Compound a39 and a40

The dichloromethane solution of imidazole (293 mg, 4.30 mmol) was cooled with ice bath, and thionyl chloride (0.094 mL, 1.29 mmol) was added thereto, and the mixture was stirred at room temperature for 1 hour. The reaction mixture was cooled to −15° C., and the dichloromethane (8 ml) solution of Compound a38 (272 mg, 0.717 mmol) was added thereto dropwise. The reaction mixture was stirred at room temperature for 3 hours. 10% citric acid aqueous solution was added to the reaction mixture, and the reaction mixture was extracted. The organic layer was washed with water, and the solvent was concentrated under reduced pressure. The obtained residue was dissolved in dichloromethane (4 mL), sodium metaperiodate (399 mg, 1.86 mol) and ruthenium oxide hydrate (2.4 mg, 0.016 mmol) were added thereto while cooling in ice. The reaction mixture was stirred at room temperature for 2 hours. The reaction mixture was diluted with ethyl acetate, and the insoluble matter was filtered off. The filtrate was extracted, and the organic layer was washed with water, and then the solvent was concentrated under reduced pressure. The obtained residue was purified by silica gel column chromatography (hexane-ethyl acetate) to afford a mixture of Compound a39 (148 mg, yield 47%) and Compound a40 (84 mg, yield 26%). Wherein, the ratio of both was calculated based on the area ratio (1.00: 0.55) of completely independent two signals at δ4.26 ppm (2H, s, Compound a39) and δ5.00-5.10 ppm (1H, m, Compound a40) in $^1$H-NMR.

85

Step 4 Preparation of a Mixture of Compound a41 and a42

The mixture of Compound a39 (141 mg, 0.320 mmol) and Compound a40 (80 mg, 0.176 mmol) was dissolved in tetrabutylammoniumfluoride (1 mol/L, THF solution, 0.991 mL, 0.991 mmol), and the mixture was stirred at room temperature for 21 hours. 10% citric acid aqueous solution (2 mL) was added to the reaction mixture, and the reaction mixture was stirred at room temperature for 1 hour. The reaction mixture was extracted with ethyl acetate, and the organic layer was concentrated under reduced pressure. The obtained residue was purified by silica gel column chromatography (hexane-ethyl acetate) to afford a mixture of Compound a41 (110 mg, yield 90%) and Compound a42 (63 mg, yield 90%). Wherein, the ration of both was calculated based on the area ratio (1.00:0.55) of completely independent two signals at δ4.78-4.92 ppm (1H, m, Compound a41) and δ5.00-5.10 ppm (1H, m, Compound a42) in $^1$H-NMR.

Step 5 Preparation of Compound a43

The mixture of Compound a41 (108 mg, 0.283 mmol) and Compound a42 (62 mg, 0.156 mmol) was dissolved in ethyl acetate (5 mL). 10% palladium-carbon catalyst (wetted with 50% water, 56 mg, 0.013 mmol) was added to the reaction mixture under nitrogen atmosphere, and the reaction mixture was stirred under hydrogen atmosphere (1 atmosphere) at room temperature for 24 hours. The reaction mixture was filtered, and the filtrate was concentrated under reduced pressure. The obtained crude product of a mixture of Compound a43 and unreacted Compound a42 was dissolved in THF (2 mL) and methanol (2 mL). 2 mol/L sodium hydrate aqueous solution (0.283 mL, 0.566 mmol) was added to the reaction mixture, and the reaction mixture was stirred at room temperature for 4.5 hours. The reaction mixture was concentrated, and extracted with ethyl acetate. After concentrated under reduced pressure, the obtained residue was purified by silica gel column chromatography (hexane-ethyl acetate) to afford Compound a43 (121 mg, yield 95%).

$^1$H-NMR (CDCl$_3$) δ: 1.29-1.38 (4H, m), 1.45 (9H, s), 1.91-2.03 (4H, m), 3.27-3.33 (1H, m), 3.48 (1H, ddd, J=9.4, 6.0, 1.8 Hz), 3.59 (1H, ddd, J=9.4, 4.0, 1.3 Hz), 3.67-3.73 (1H, m), 3.88-3.97 (1H, m), 4.40 (1H, ddd, J=47.4, 9.0, 6.0 Hz), 4.39-4.60 (1H, m), 4.82-4.88 (1H, m).

Example 6 Preparation of Compound a44-2

[Formula 105]

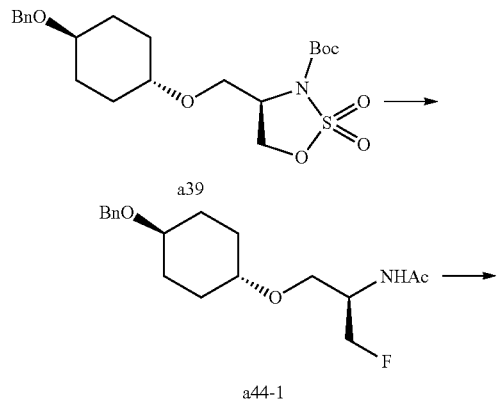

86

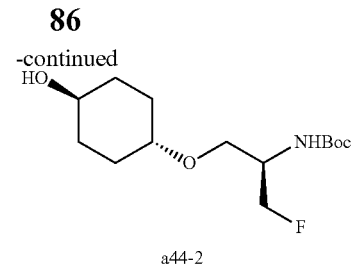

Step 1 Preparation of Compound a44-1

The THF (0.4 mL) solution of Compound a39 (44 mg, 0.10 mmol) was dissolved in tetrabutylammoniumfluoride (1 mol/L, THF solution, 0.12 mL, 0.120 mmol), and the reaction mixture was stirred at room temperature for 1 hour. Saturated ammonium chloride solution (2 mL) was added to the reaction solution, and the reaction mixture was stirred at room temperature for 1 hour. The reaction mixture was extracted with ethyl acetate, and the organic layer was concentrated under reduced pressure. The obtained residue was dissolved in 4 mol/L hydrochloric acid-ethyl acetate (0.25 mL), and the mixture was stirred at room temperature for 1 hour. The reaction mixture was concentrated under reduced pressure, and the obtained crude product was dissolved in THF (0.4 mL). Acetic acid anhydride (0.014 mL, 0.149 mmol) and triethylamine (0.028 mL, 0.199 mmol) were added to the reaction solution at room temperature. The reaction mixture was stirred for 30 minutes. Saturated ammonium chloride solution was added to the reaction mixture, and the reaction mixture was extracted. The organic layer was washed with water, and the organic layer was concentrated under reduced pressure. The obtained residue was purified by silica gel column chromatography (hexane-ethyl acetate) to afford Compound a44-1 (25 mg, yield 78%).

Step 2 Preparation of Compound a44-2

Compound a44-1 (49 mg, 0.152 mmol) was dissolved in methanol (0.5 mL). 10% palladium-carbon catalyst (wetted with 50% water, 16 mg) was added thereto under nitrogen atmosphere, and the mixture was stirred under hydrogen atmosphere (1 atmosphere) at room temperature for 2 hours. The reaction mixture was filtered, and the filtrate was concentrated under reduced pressure. The obtained residue was purified by silica gel column chromatography (hexane-ethyl acetate) to afford Compound a44-2 (36 mg, yield 100%).

$^1$H-NMR (CDCl$_3$) δ: 1.28-1.36 (4H, m), 1.95-2.03 (4H, m), 2.01 (3H, s), 3.31 (1H, m), 3.49 (1H, m), 3.59 (1H, m), 3.69 (1H, m), 4.28 (1H, m), 4.32-4.60 (2H, m), 5.83 (1H, br.s).

Example 9 Preparation of Compound a61

[Formula 106]

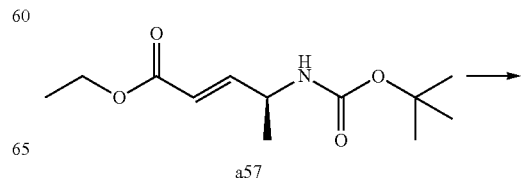

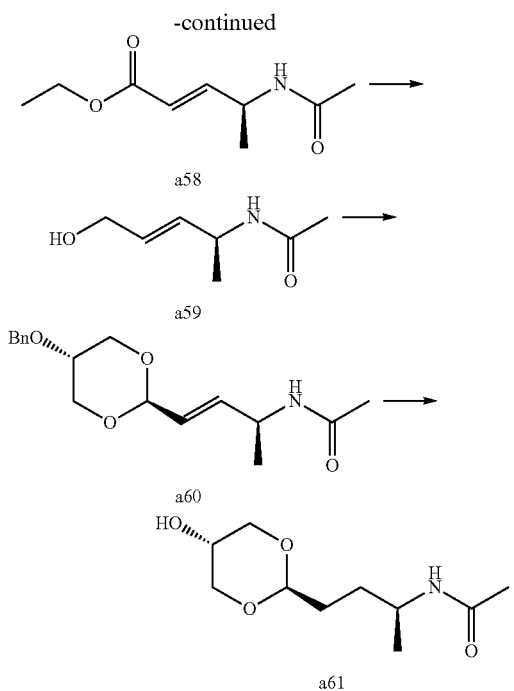

Step 1 Preparation of Compound a58

Compound a57 (131 mg, 0.54 mmol; WO201005562) was dissolved in dichloromethane (2.5 mL), and 1 mol/L diisobutylaluminum hydride (2.16 ml, 2.16 mmol) was added thereto at −78° C. The reaction mixture was stirred at room temperature for 1 hour. Ethyl acetate (0.4 ml), saturated Rochelle's salt and ethyl acetate (5 ml) were added to the reaction mixture, and the mixture was stirred for 1 hour at room temperature. The reaction mixture was concentrated under reduced pressure, and extracted with dichloromethane. The organic layer was washed with water and brine, and then dried over anhydrous sodium sulfate. The solvent was distilled off under reduced pressure, the resulting residue was purified by silica gel column chromatography (chloroform-methanol) to afford Compound a58 (63 mg, 58% yield).

$^1$H NMR (CDCl$_3$) δ: 1.28 (t, J=7.2 Hz, 3H), 1.29 (d, J=7.2 Hz, 3H), 2.01 (s, 3H), 4.17 (q, J=7.2 Hz, 2H), 4.74 (m, 1H), 5.42 (br.s, 1H), 5.89 (d, J=15.6 Hz, 1H), 6.87 (dd, J=4.8, 15.6 Hz, 1H).

Step 2 Preparation of Compound a59

Compound a58 (440 mg, 2.04 mmol) was dissolved in dichloromethane (4 mL), and trifluoroacetic acid (1.57 ml, 20.4 mmol) was added at 0° C. The mixture was stirred for 30 minutes. The reaction mixture was concentrated under reduced pressure, and triethylamine (847 μl, 6.11 mmol) and acetic anhydride (385 μl, 4.07 mmol) were added to the dichloromethane solution of the resulting residue (3.0 mL). The mixture was stirred for 1 hour. Water was added to the reaction mixture and the mixture was extracted with dichloromethane. The organic layer was washed with 2 mol/L hydrochloric acid and saturated brine, and dried over anhydrous sodium sulfate. The solvent was distilled off under reduced pressure, and the resulting residue was dissolved in THF—H$_2$O (2 ml; 1:1). 2 mol/L sodium hydroxide was added thereto. The reaction solution was stirred at room temperature for 30 minutes. Water was added to the reaction mixture, and the mixture was extracted with dichloromethane. The organic layer was washed with water and brine, and dried over anhydrous sodium sulfate. The organic layer was concentrated under reduced pressure. The obtained residue was purified by silica gel column chromatography (chloroform-methanol) to afford Compound a59 (220 mg, 75% yield).

$^1$H NMR (CDCl$_3$) δ: 1.25 (d, J=6.8 Hz, 3H), 1.40 (s, 1H), 1.99 (s, 3H), 4.55 (br.s, 2H), 4.60 (m, 1H), 5.32 (s, 1H), 5.68 (m, 1H), 5.76 (m, 1H).

Step 3 Preparation of Compound a60

Compound a59 (40 mg, 0.279 mmol) was dissolved in dichloromethane (2 mL) and manganese dioxide (484 mg, 5.56 mmol) was added thereto, and the mixture was stirred for 1 hour. The reaction mixture was filtered, and the filtrate was concentrated under reduced pressure. The obtained residue was purified by silica gel column chromatography (hexane-ethyl acetate) to give the aldehyde compound (28 mg, 71% yield).

2-(benzyloxy) propane-1,3-diol (54 mg, 0.298 mmol) and pyridinium paratoluene sulfonate (2.5 mg, 9.9 μmol) were added to the toluene (1 ml) solution of the aldehyde, and the mixture was stirred at 90° C. for 6 hours. The reaction solution was concentrated, and the residue was purified by prep HPLC (0.1% formic acid-containing acetonitrile-water) to afford Compound a60 (3.8 mg, 6% yield) and its cis isomer (4.0 mg, 6% yield).

$^1$H NMR (CDCl$_3$) δ: 1.23 (d, J=8.4 Hz, 3H), 1.95 (s, 3H), 3.49 (dd, J=10.8, 10.8 Hz, 2H), 3.67 (m, 1H), 3.49 (dd, J=4.8, 10.8 Hz, 2H), 4.56 (s, 2H), 4.62 (m, 1H), 4.86 (d, J=4.4 Hz, 1H), 5.32 (d, J=8.4 Hz, 1H), 5.59 (ddd, J=1.6, 4.4, 15.6 Hz, 1H) 5.93 (dd, J=5.2, 15.6 Hz, 1H), 7.27-7.37 (m, 5H).

Cis isomer; $^1$H NMR (CDCl$_3$) δ: 1.24 (d, J=6.8 Hz, 3H), 1.96 (s, 3H), 3.25 (s, 1H), 3.87 (d, J=12.0 Hz, 2H), 4.23 (d, J=12.0 Hz, 2H), 4.64 (m, 1H), 4.67 (s, 2H), 5.02 (d, J=4.8 Hz, 1H), 5.36 (d, J=7.2 Hz, 1H), 5.69 (ddd, J=1.6, 4.4, 16.0 Hz, 1H) 5.98 (dd, J=4.8, 16.0 Hz, 1H), 7.27-7.39 (m, 5H).

Step 4 Preparation of Compound a61

Compound a60 (4.0 mg, 0.012 mmol) was dissolved in methanol (1 mL), and palladium hydroxide (1 mg, 0.16 mmol) was added thereto. The reaction mixture was stirred under hydrogen atmosphere for 5 hours. The reaction solution was filtered, and the filtrate was concentrated under reduced pressure to afford Compound a61 (2.6 mg, 100% yield) as a crude product.

$^1$H NMR (CDCl$_3$) δ: 1.13 (d, J=6.8 Hz, 3H), 1.45-1.68 (m, 4H), 1.95 (s, 3H), 3.67 (dd, J=10.8, 10.8 Hz, 2H), 3.67 (m, 1H), 3.88 (m, 1H), 3.97 (m, 1H), 4.16 (d, J=4.8, 10.8 Hz, 2H), 4.44 (dd, J=4.8, 4.8 Hz, 1H), 5.31 (br.s, 1H).

Example 10 Preparation of Compound a66

[Formula 107]

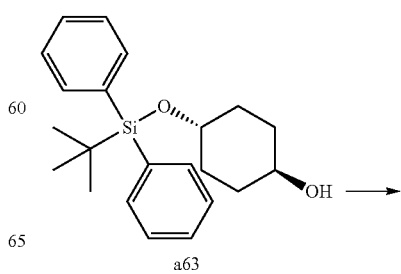

a63

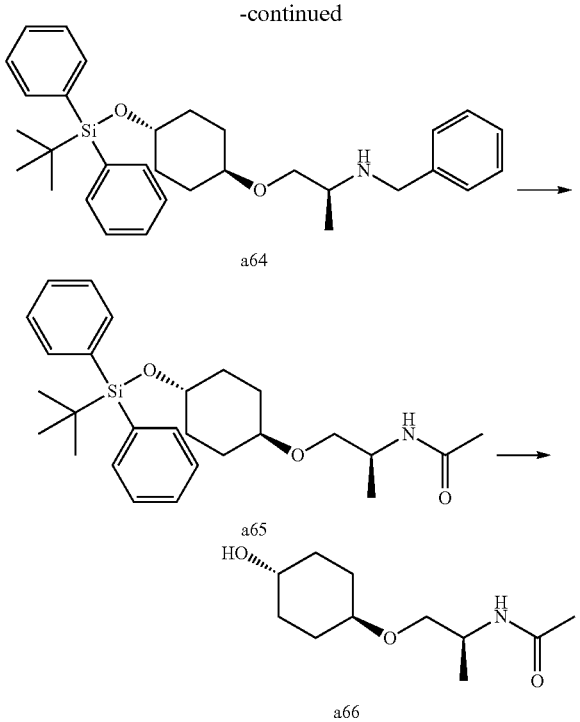

Step 1 Preparation of Compound a64

Compound a63 (3.0 g, 127 mmol) was dissolved in a mixed solution of DMF (30 mL) and THF (30 mL), and sodium hydride (0.51 g, 12.7 mmol) was added thereto while cooling in ice. The reaction mixture stirred for 30 minutes while cooling in ice. The THF (5 mL) solution of (S)-3-benzyl-4-methyl-1,2,3-oxathiazolidine-2,2-dioxide (2.31 g, 10.15 mmol) was added to the reaction solution while cooling in ice. The mixture was stirred at 40° C. for 2 hours. 2 mol/L aqueous hydrochloric acid solution (17 mL) was added thereto while cooling in ice, followed by stirring for 1 hour at room temperature. 2 mol/L sodium hydroxide solution (30 mL) was added thereto, and the mixture was extracted with ethyl acetate. The reaction solvent was evaporated under reduced pressure, and the resulting residue was purified by amino silica gel column chromatography (chloroform-methanol) to afford Compound a64 (3.7 g, 87% yield).

$^1$H NMR (CDCl$_3$) δ: 1.01 (d, J=6.0 Hz, 3H), 1.05 (m, 9H), 1.15-1.22 (m, 2H), 1.33-1.41 (m, 2H), 1.74 (m, 2H), 1.88 (m, 2H), 2.85 (m, 1H), 3.25 (m, 2H), 3.35 (dd, J=4.0, 9.2 Hz, 1H), 3.68 (m, 1H), 3.70 (d, J=13.2 Hz, 1H), 3.83 (d, J=13.2 Hz, 1H), 7.20-7.44 (m, 11H), 7.66 (d, J=6.8 Hz, 4H).

Step 2 Preparation of Compound a65

Compound a64 (50.5 g, 101 mmol) was dissolved in ethanol (505 mL), and Pd—C (11.3 g, 5.0 mmol) and ammonium formate (12.7 g, 201 mmol) were added thereto, and the mixture was stirred at 65° C. for 3 hours. Ammonium formate (6.35 g, 101 mmol) was further added thereto, and the mixture was stirred at 65° C. for 2.5 hours. The reaction mixture was filtered, and the filtrate was concentrated under reduced pressure. Saturated sodium carbonate aqueous solution was added to the residue and the mixture was extracted with ethyl acetate. The organic layer was washed with water and brine, and dried over anhydrous magnesium sulfate. The solvent was distilled off under reduced pressure, and the resulting residue was dissolved in dichloromethane (253 mL), and triethylamine (13.95 ml, 101 mmol) and acetic anhydride (10.5 ml, 111 mmol) were added thereto. The mixture was stirred at room temperature for 1.5 hours. Water was added to the reaction mixture, and the mixture was extracted with ethyl acetate. The organic layer was washed with brine and dried over anhydrous magnesium sulfate. The solvent was distilled off under reduced pressure, the resulting residue was purified by silica gel column chromatography (chloroform-methanol) to afford Compound a65 (37.75 g, 83% yield).

$^1$H NMR (CDCl$_3$) δ: 1.05 (m, 9H), 1.12 (d, J=6.8 Hz, 3H), 1.16-1.26 (m, 2H), 1.33-1.43 (m, 2H), 1.75 (m, 2H), 1.89 (m, 2H), 1.93 (s, 3H), 3.28 (m, 1H), 3.32 (m, 1H), 3.38 (dd, J=4.0, 9.2 Hz, 1H), 3.71 (m, 1H), 4.08 (m, 1H), 5.63 (m, 1H), 7.34-7.44 (m, 6H), 7.66 (d, J=6.8 Hz, 4H).

Step 3 Preparation of Compound a66

Compound a65 (30.2 g, 66.6 mmol) was dissolved in THF (100 mL) and 1 mol/L tetrabutylammonium fluoride (100 mL, 100 mmol) was added thereto, and the mixture was stirred at 70° C. for 7 hours. The reaction solution was distilled off under reduced pressure, and the resulting residue was purified by silica gel column chromatography (chloroform-methanol) to afford Compound a66 (11.65 g, 81% yield).

$^1$H NMR (CDCl$_3$) δ: 1.17 (d, J=6.8 Hz, 3H), 1.23-1.35 (m, 4H), 1.8-1.90 (m, 2H), 1.97 (s, 3H), 3.27 (m, 1H), 3.38 (dd, J=4.0, 9.6 Hz, 1H), 3.44 (dd, J=4.0, 9.6 Hz, 1H), 3.72 (m, 1H), 4.13 (m, 1H), 5.66 (br.s, 1H).

Example 12 Preparation of Compound a79

[Formula 108]

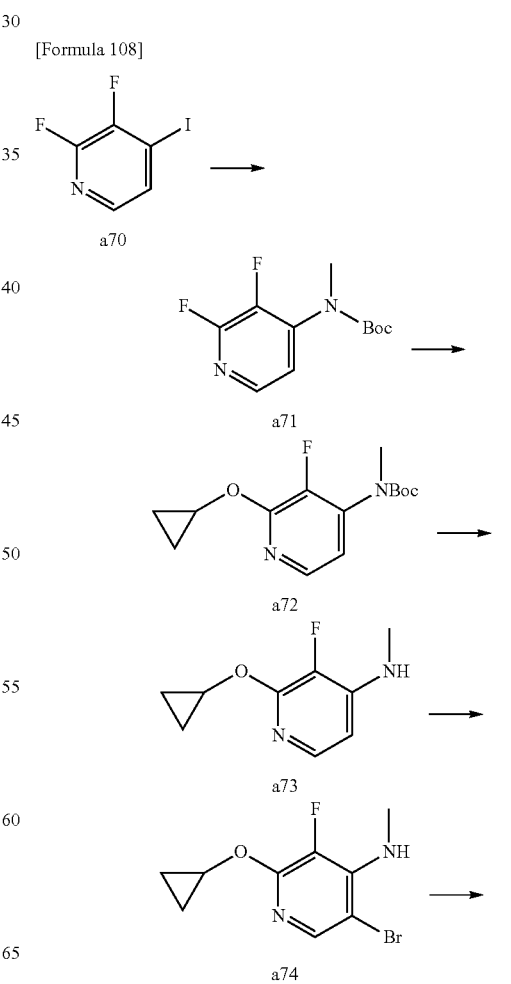

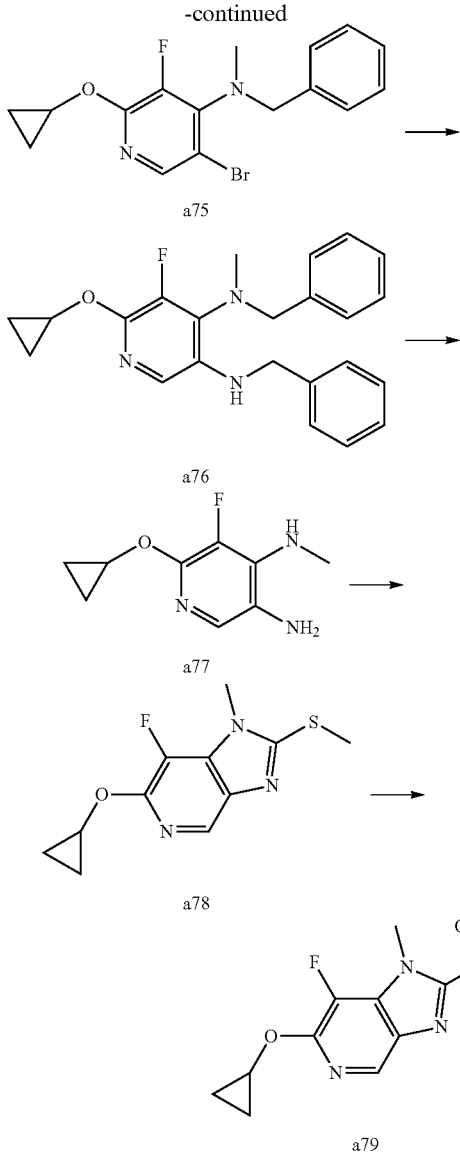

a75 a76 a77 a78 a79

Step 1 Preparation of Compound a71

Compound a70 (1.0 g, 4.15 mmol) was dissolved in dioxane (16 mL), and tertiary butyl methyl carbamate (653 mg, 4.98 mmol), 2-dicyclohexylphosphino-2',4',6'-triisopropyl-biphenyl (297 mg, 0.622 mmol), potassium phosphate (2.20 g, 10.73 mmol) and tris (dibenzylideneacetone) palladium (190 mg, 0.207 mmol) were added thereto. The mixture was stirred at 100° C. for 5 hours. Tertiary butyl methyl carbamate (218 mg, 1.66 mmol), 2-dicyclohexyl-phosphino-2',4',6'-triisopropyl biphenyl (99 mg, 0.207 mmol), potassium phosphate (0.73 g, 3.57 mmol) and tris (dibenzylideneacetone) palladium (0) (63.3 mg, 0.069 mmol) were added to the mixture and the mixture was stirred for 3 hours. Tertiary butyl methyl carbamate (435 mg, 3.32 mmol), 2-dicyclohexylphosphino-2',4',6'-triisopropyl biphenyl (99 mg, 0.207 mmol) and tris (dibenzylideneacetone) palladium (0) (63.3 mg, 0.069 mmol) were then added to the mixture and the mixture was stirred for 5.5 hours. Water was added to the reaction mixture, and the mixture was extracted with ethyl acetate. The organic layer was washed with saturated brine. The organic layer was dried over anhydrous magnesium sulfate, and the organic layer was concentrated under reduced pressure. The residue was purified by silica gel column chromatography (hexanes-ethyl acetate) to afford compound a71 (0.75 g, 74% yield).

[M+H]=244.95, Method Condition 3: retention time 2.08 min

Step 2 Preparation of Compound a72

Cyclopropanol (105 mg, 1.80 mmol) was dissolved in THF (5.0 mL) and Compound a71 (400 mg, 1.64 mmol) was added to the mixture. Potassium tert-butoxide (239 mg, 2.12 mmol) was added to the reaction mixture under ice-cooling and the mixture was stirred for 3.5 hours under ice-cooling. Water was added to the reaction mixture, and the mixture was extracted with ethyl acetate. The organic layer was washed with saturated brine, and dried over anhydrous magnesium sulfate. The solvent was evaporated under reduced pressure to afford compound a72 (440 mg) as a crude product.

[M+H]=283.30, Method Condition 3: retention time 2.18 min

Step 3 Preparation of Compound a73

Compound a72 (440 mg, 1.55 mmol) was dissolved in dichloromethane (5.0 mL) and 4 mol/L of hydrochloric acid-dioxane (10 mL, 40 mmol) was added to the mixture. Then the mixture was stirred at room temperature for 20 hours. The reaction solution was evaporated under reduced pressure, and 1 mol/L of aqueous sodium carbonate solution was added to the mixture. The mixture was extracted with ethyl acetate. The organic layer was washed with saturated brine, and dried over anhydrous magnesium sulfate. The solvent was evaporated under reduced pressure to afford compound a73 (278 mg) as a crude product. [M+H]=183.00, Method Condition 3: retention time 0.98 min Step 4 Preparation of Compound a74

Compound a73 (278 mg, 1.52 mmol) was dissolved in acetonitrile (5.0 mL), and N-bromosuccinimide (312 mg, 1.72 mmol) was added to the mixture. The mixture was stirred for 2 hours at room temperature. After vacuum evaporation of the solvent, the residue was purified by silica gel column chromatography (hexanes-ethyl acetate) to afford compound a74 (173 mg, 40% yield).

$^1$H-NMR (CDCl$_3$) δ: 0.77-0.82 (m, 4H), 3.17-3.20 (m, 3H), 4.25-4.27 (m, 1H), 4.44 (s, 1H).

[M+H]=262.85, Method Condition 3: retention time 2.09 min

Step 5 Preparation of Compound a75

Compound a74 (173 mg, 0.663 mmol) was dissolved in DMF (3.0 mL) and sodium hydride (34.5 mg, 0.861 mmol) was added to the mixture under ice-cooling, and the mixture was stirred for 5 minutes. Benzyl bromide (0.087 mL, 0.729 mmol) was added to the reaction solution, and the mixture was stirred for 1.5 hours under ice-cooling. Sodium hydride (3.5 mg, 0.086 mmol) and benzyl bromide (0.009 mL, 0.0757 mmol) were added thereto, and the mixture was stirred for 50 minutes. Water was added to the reaction mixture, and the mixture was extracted with ethyl acetate. The organic layer was washed with saturated brine, and the organic layer was dried over anhydrous magnesium sulfate. After the solvent was evaporated under reduced pressure, the residue was purified by silica gel column chromatography (hexane-ethyl acetate) to afford compound a75 (174 mg, 75% yield).

[M+H]=350.90, Method Condition 3: retention time 2.86 min

Step 6 Preparation of Compound a76

Compound a75 (170 mg, 0.484 mmol) was dissolved in toluene (4.0 mL), and sodium tert-butoxide (93.0 mg, 0.968 mmol), tris (dibenzylideneacetone) palladium (0) (44.3 mg, 0.048 mmol), 2,2'-bis (diphenylphosphino)-1, 1'-binaphthyl (60.3 mg, 0.097 mmol) and benzyl amine (0.212 mL, 1.938 mmol) were added to the mixture. The mixture was stirred at 100° C. for 2 hours. Its salt was removed by filtration, and the reaction solution was evaporated under reduced pressure. The residue was purified by silica gel column chromatography (hexane-ethyl acetate) to afford compound a76 (140 mg, 76% yield).

[M+H]=378.05, Method Condition 3: retention time 2.83 min

Step 7 Preparation of Compound a77

Compound a76 (140 mg, 0.371 mmol) was dissolved in methanol (3.0 mL), and palladium-carbon (96.0 mg, 0.115 mmol) and ammonium formate (234 mg, 0.371 mmol) were added to the mixture. The mixture was stirred at 60° C. for 45 minutes. The reaction mixture was cooled to room temperature and dichloromethane (5.0 mL) was added to the mixture. The insoluble was removed by Celite filtration. The solvent was evaporated under reduced pressure to afford compound a77 (69.0 mg) as a crude product.

Step 8 Preparation of Compound a78

Compound a77 (69.0 mg, 0.349 mmol) was dissolved in THF (3.0 mL) and triethylamine (0.206 mL, 1.484 mmol) and 1, 1'-thiocarbonyldiimidazole (74.2 mg, 0.408 mmol) were added to the mixture. The mixture was stirred at room temperature for 2 hours. Triethylamine (0.100 mL, 0.722 mmol) and 1,1'-thiocarbonyldiimidazole (20.0 mg, 0.112 mmol) were added to the mixture, and the mixture was stirred at room temperature for 1 hour. Methyl iodide (0.500 mL, 8.00 mmol) was added to the mixture, and the mixture was stirred for 2 hours at room temperature. The solvent was distilled off under reduced pressure, and the residue was purified by silica gel column chromatography (hexane-ethyl acetate) to afford compound a78 (36.0 mg, 38% yield).

[M+H]=253.95, Method Condition 3: retention time 1.87 min

Step 9 Preparation of Compound a79

Compound a78 (36.0 mg, 0.142 mmol) was dissolved in dichloromethane (2.0 mL), and 69 wt % m-chloroperoxybenzoic acid (74.6 mg, 0.298 mmol) was added thereto while cooling in ice, and the mixture was stirred at room temperature for 18 hours. 69 wt % m-chloroperbenzoic acid (25.0 mg, 0.703 mmol) was added thereto, and the mixture was stirred for 3.5 hours. 69 wt % m-chloroperoxybenzoic acid (10.0 mg, 0.281 mmol) was added thereto, and the mixture was stirred for 1.5 hours. The reaction solution was purified by silica gel column chromatography (hexane-ethyl acetate) to afford the compound a79 (35.0 mg, 86% yield).

[M+H]=285.90, Method Condition 3: retention time 1.77 min

Example 13 Preparation of Compound a85

[Formula 109]

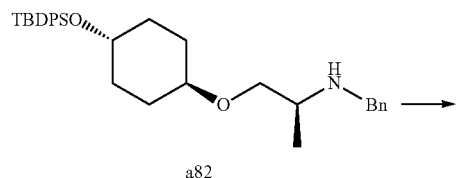

a82

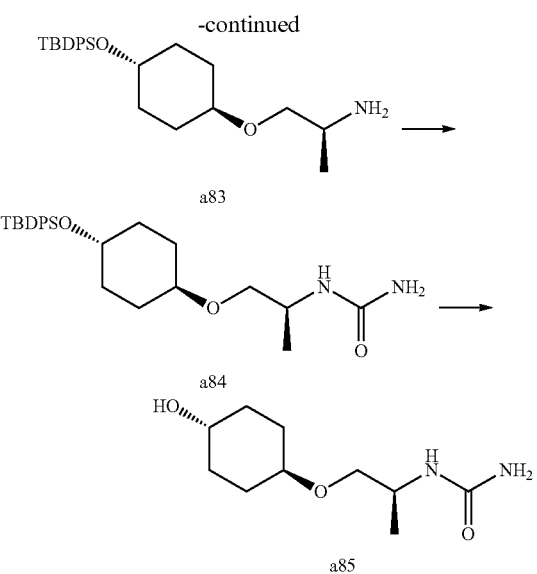

Step 1 Preparation of Compound a83

Compound a82 (5.00 g, 9.96 mmol) was dissolved in ethanol (20 mL), Palladium-carbon (0.5 g) and ammonium formate (6.28 g, 100 mmol) were added thereto, and the mixture was stirred at 80° C. for 3 hours. The insoluble matter was removed by celite filtration, and the resulting filtrate was evaporated under reduced pressure. The obtained crude product of Compound a83 was directly used for the next step.

[M+H]=412.05, Method Condition 3: retention time 2.19 min

Step 2 Preparation of Compound a84

1,1'-carbonyl diimidazole (3.23 g, 19.96 mmol) was dissolved in dimethylformamide (25 mL), and the dimethylformamide (25 mL) solution of Compound a83 was added dropwise while cooling in ice. The mixture was stirred at room temperature at 1.5 hours. 28% ammonium aqueous solution (10 mL, 129 mmol) was added thereto while cooling in ice, and the mixture was stirred at room temperature for 17 hours. 0.5 mol/L hydrochloric acid aqueous solution was added to the reaction solution, and the mixture was extracted with ethyl acetate. The organic layer was dried over anhydrous magnesium sulfate, and the solvent was evaporated under reduced pressure. The obtained residue was purified by silica gel column chromatography (hexane-ethyl acetate, chloroform-methanol) to afford Compound a84 (4.35 g, 96% yield).

[M+H]=455.10, Method Condition 3: Retention time 2.82 min $^1$H-NMR (CDCl$_3$) δ: 1.05 (s, 9H), 1.12 (d, J=6.8 Hz, 3H), 1.18-1.26 (m, 2H), 1.33-1.44 (m, 2H), 1.70-1.79 (m, 2H), 1.87-1.95 (m, 2H), 3.26-3.31 (m, 2H), 3.42 (dd, J=9.0, 3.5 Hz, 1H), 3.66-3.80 (m, 2H), 4.51-4.62 (m, 2H), 7.35-7.44 (m, 6H), 7.63-7.68 (m, 4H).

Step 3 Preparation of Compound a85

1.0 mol/L tetrabutylammonium fluoride-tetrahydrofuran solution (111 mL, 11.0 mmol) was added to Compound a84 (4.35 g, 9.57 mmol), and the mixture was refluxed for 4.5 hours. The reaction solution was evaporated under reduced pressure, and the obtained residue was purified by silica gel column chromatography (hexane-ethyl acetate, chloroform-methanol) to afford Compound a85 (510 mg, 24% yield).

¹H-NMR (MeOD) δ: 1.13 (d, J=6.8 Hz, 3H), 1.26-1.37 (m, 4H), 1.89-1.96 (m, 2H), 1.98-2.05 (m, 2H), 3.25-3.33 (m, 1H), 3.35-3.39 (m, 2H), 3.40-3.44 (m, 2H), 3.55-3.63 (m, 1H), 3.76-3.84 (m, 1H).

[M+H]=217.00, Method Condition 3: Retention time 0.72 min

Example 14 Preparation of Compound a92

[Formula 110]

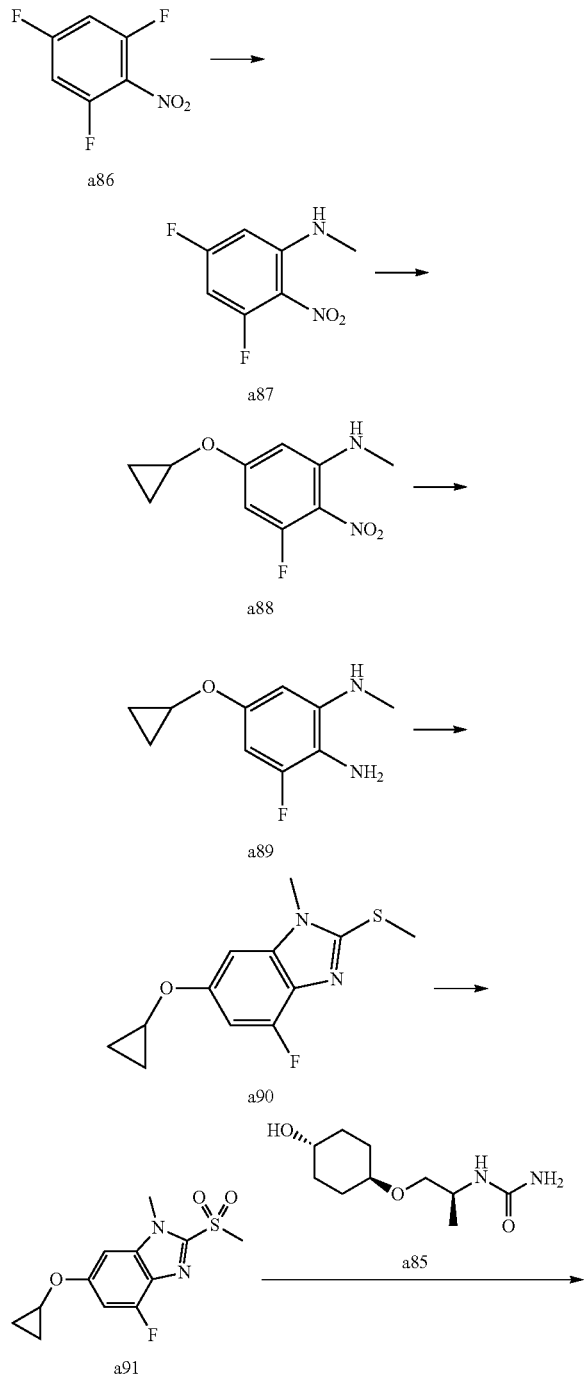

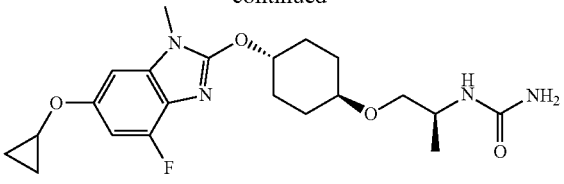

Step 1 Preparation of Compound a87

Compound a86 (1.34 mL, 11.4 mmol) was dissolved in tetrahydrofuran (20 mL), triethylamine (1.90 mL, 13.7 mmol), 2.0 mol/L monomethylamine-tetrahydrofuran solution (6.0 mL, 24.0 mmol) were added thereto while cooling in ice, and the mixture was stirred at room temperature for 20 hours. Water and saturated ammonium chloride aqueous solution were added to the reaction mixture, and the mixture was extracted with ethyl acetate. The organic solution was dried with anhydrous magnesium sulfate, and then the solvent was distilled off under reduced pressure. The resulting residue was purified by silica gel column chromatography (hexane-ethyl acetate) to afford Compound a87 (1.71 g, 80% yield).

¹H-NMR (CDCl₃) δ: 2.97 (d, J=5.0 Hz, 3H), 6.18-6.28 (m, 2H), 7.63 (brs, 1H).

[M+H]=188.95, Method Condition 3: Retention time 1.87 min

Step 2 Preparation of Compound a88

Cyclobutanol (340 mg, 5.85 mmol) was dissolved in tetrahydrofuran (10 mL), and Compound a87 (1.00 g, 5.32 mmol), potassium carbonate (1.62 g, 11.7 mmol) and 18-crownether-6 (4.22 g, 16.0 mmol) were added thereto. The mixture was stirred at 60° C. for 3 hours. Water and 1.0 mol/L hydrochloric acid aqueous solution were added to the reaction solution, and the mixture was extracted with ethyl acetate. The organic layer was dried over anhydrous magnesium sulfate, and then the solvent was distilled off. The obtained residue was purified by silica gel column chromatography (hexane-ethyl acetate) to afford Compound a88 (254 mg, 21% yield).

¹H-NMR (CDCl₃) δ: 2.96 (d, J=5.0 Hz, 3H), 3.77-3.81 (m, 1H), 6.11-6.13 (m, 1H), 6.20 (dd, J=13.6, 2.5 Hz, 1H), 7.84 (brs, 1H).

[M+H]=226.95, Method Condition 3: Retention time 2.10 min

Step 3 Preparation of Compound a89

Compound a88 (253 mg, 1.12 mmol) was dissolved in the mixed solvent of ethanol (4 mL) and tetrahydrofuran (4 mL), and zinc (732 mg, 11.2 mmol) and ammonium chloride (732 mg, 11.2 mmol) were added thereto while cooling in ice. The mixture was stirred at room temperature for 5.5 hours. The insoluble matter was removed by celite filtration, and the obtained filtrate was evaporated under reduced pressure to afford Compound a89 as a crude product.

[M+H]=197.05, Method Condition 3: Retention time 1.37 min

Step 4 Preparation of Compound a90

The crude compound a89 was dissolved in tetrahydrofuran (5 mL), and 1,1'-thiocarbonyldiimidazole (438 mg, 2.46 mmol) and imidazole (304 mg, 4.47 mmol) were added thereto. The mixture was stirred at room temperature for 16 hours. 1,1'-thiocarbonyldiimidazole (319 mg, 1.79 mmol) was added thereto, and the mixture was stirred at room temperature for 2.5 hours. Potassium carbonate (618 mg, 4.47 mmol) and methyl iodide (0.182 ml, 2.91 mmol) were added to the reaction mixture, and the mixture was stirred at room temperature for 15 hours. The insoluble matter was removed by filtration, and then the resulted filtrate was evaporated under reduced pressure. The obtained residue was purified by silica gel column chromatography (hexane-ethyl acetate) to afford Compound a90 (269 mg, 95% yield).

[M+H]=253.25, Method Condition 3: Retention time 1.91 min

Step 5 Preparation of Compound a91

Compound a90 (269 mg, 1.07 mmol) was dissolved in dichloromethane (5 mL), and 3-chloroperbenzoic acid (560 mg, 2.24 mmol) was added thereto while cooling in ice. The mixture was stirred at room temperature for 2.5 hours. The reaction solution was distilled off under reduced pressure, and the resulted residue was purified by silica gel column chromatography (hexane-ethyl acetate) to afford Compound a91 (260 mg, 86% yield).

[M+H]=284.90, Method Condition 3: Retention time 1.83 min

Step 6 Preparation of Compound a92

Compound a85 (44.9 mg, 0.208 mmol) was dissolved in dimethylformamide (1 mL), and potassium tert-butoxide (66.9 mg, 0.623 mmol) was added thereto while cooling in ice. The mixture was stirred for 10 minutes directly. The dimethylformamide (1.5 mL) solution of Compound a91 (59.0 mg, 0.280 mmol) was added thereto, and the mixture was stirred for 4 hours. Water was added to the reaction mixture, and the mixture was extracted with ethyl acetate. The organic layer was dried over anhydrous magnesium sulfate, and then the solvent was distilled off under reduced pressure. The resulted residue was purified by silica gel column chromatography (hexane-ethyl acetate, chloroform-methanol) to afford Compound a92 (58 mg, 67% yield).

$^1$H-NMR (CDCl$_3$) δ: 0.77-0.80 (m, 4H), 1.19 (d, J=6.8 Hz, 3H), 1.49-1.71 (m, 4H), 1.97-2.05 (m, 2H), 2.16-2.25 (m, 2H), 3.35-3.45 (m, 2H), 3.49-3.53 (m, 4H), 3.71-3.77 (m, 1H), 3.87 (brs, 1H), 4.50 (brs, 2H), 4.59 (brd, J=6.0 Hz, 1H), 5.16-5.24 (m, 1H), 6.62 (d, J=2.0 Hz, 1H), 6.67 (dd, J=12.0, 2.0 Hz, 1H).

[M+H]=421.05, Method Condition 3: Retention time 1.95 min

Example 15 Preparation of Compound a94

[Formula 111]

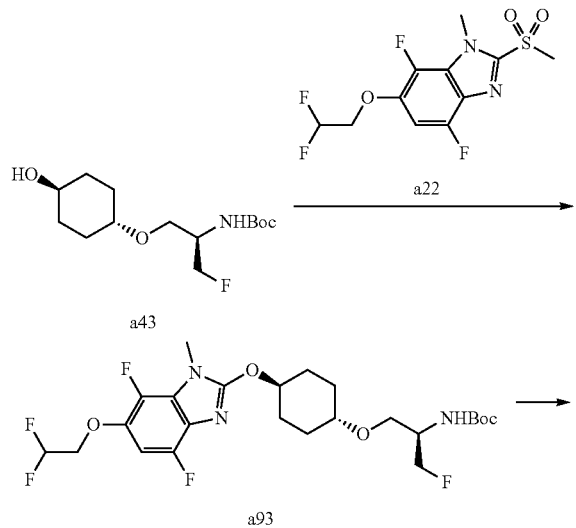

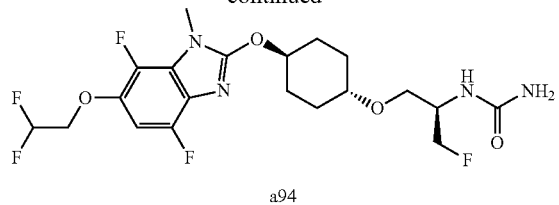

Step 1 Preparation of Compound a93

The mixture of Compound a43 (11 mg, 0.062 mmol) and Compound a22 (30 mg, 0.093 mmol) were dissolved in THF (0.7 mL). Potassium tert-butoxide (17 mg, 0.156 mmol) was added to the reaction mixture under ice-cooling, and the mixture was stirred for 1 hour. Water was added to the reaction mixture, and the mixture was extracted with ethyl acetate. After evaporated under reduced pressure, the obtained residue was purified by silica gel column chromatography (hexane-ethyl acetate) to afford Compound a93 (20 mg, 59% yield).

Step 2 Preparation of Compound a94

Compound a93 (20 mg, 0.037 mmol) was dissolved in methylene chloride (0.7 mL). Tifluoroacetic acid (0.28 mL, 3.7 mmol) was added to the reaction mixture while cooling in ice, and the mixture was stirred for 30 minutes. 2 mol/L sodium hydrate aqueous solution was added thereto, and the mixture was extracted with ethyl acetate. After evaporated under reduced pressure, and the resulted amino compound was dissolved in methylene chloride (0.7 mL). Pyridine (20 μL, 0.25 mmol) and 4-nitrophenylcarbonyl chloride (15 mg, 0.075 mmol) were added thereto at room temperature, and the mixture was stirred for 2 hours. Water was added to the reaction mixture, and the mixture was extracted with ethyl acetate. After evaporated under reduced pressure, the obtained carbamate compound was dissolved in acetonitrile (0.7 mL). DIEA (44 μL, 0.25 mmol) and ammonium chloride (13 mg, 0.25 mmol) was added to the reaction solution at room temperature, and the mixture was stirred for 1 hour. Water was added to the reaction mixture, and the mixture was extracted with ethyl acetate. After evaporated under reduced pressure, the resulted residue was purified by silica gel column chromatography (chloroform-methanol) to afford Compound a94 (13.6 mg, 57% yield).

$^1$H-NMR (CDCl$_3$) δ: 1.58 (m, 2H), 1.67 (m, 2H), 2.02 (m, 2H), 2.17 (m, 2H), 3.45 (m, 1H), 3.55 (m, 1H), 3.62 (m, 1H), 3.70 (s, 3H), 4.11 (m, 1H), 4.23 (dt, J=4.0, 13.2 Hz, 2H), 4.39 (m, 1H), 4.43 (Br.s, 2H), 4.50 (m, 1H), 4.62 (dd, J=4.0, 8.8 Hz, 1H), 4.88 (d, J=8.4 Hz, 1H), 5.19 (m, 1H), 6.60 (tt, J=4.0, 54.8 Hz, 1H) 6.62 (dd, J=6.0, 10.4 Hz, 1H).

Example 16 Preparation of Compound a110

[Formula 112]

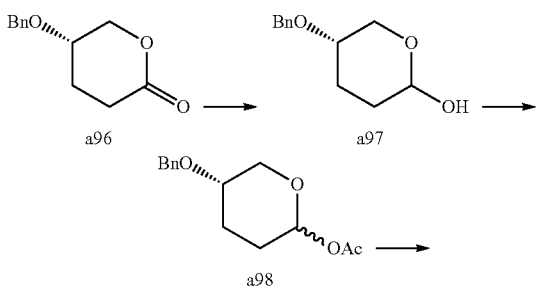

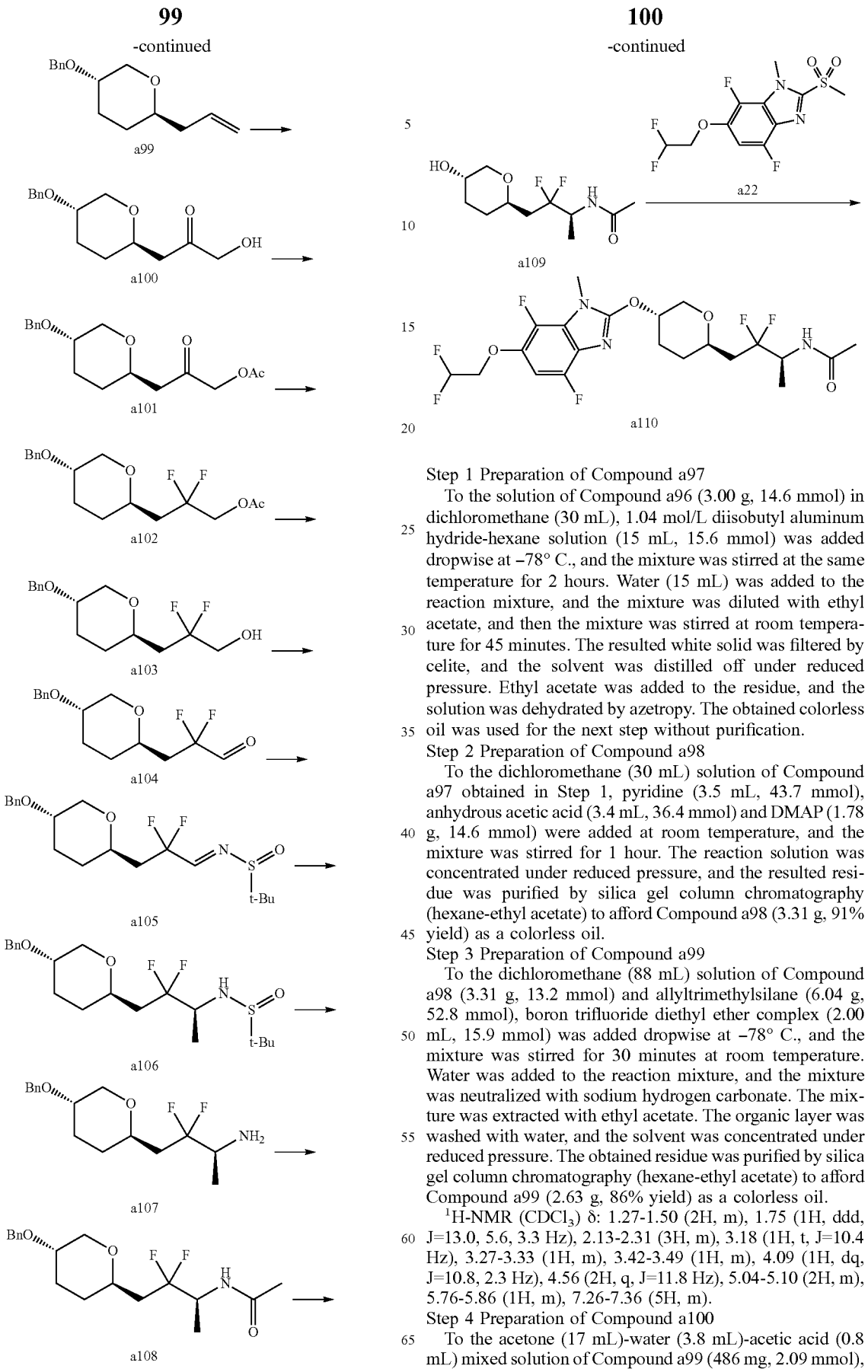

Step 1 Preparation of Compound a97

To the solution of Compound a96 (3.00 g, 14.6 mmol) in dichloromethane (30 mL), 1.04 mol/L diisobutyl aluminum hydride-hexane solution (15 mL, 15.6 mmol) was added dropwise at −78° C., and the mixture was stirred at the same temperature for 2 hours. Water (15 mL) was added to the reaction mixture, and the mixture was diluted with ethyl acetate, and then the mixture was stirred at room temperature for 45 minutes. The resulted white solid was filtered by celite, and the solvent was distilled off under reduced pressure. Ethyl acetate was added to the residue, and the solution was dehydrated by azetropy. The obtained colorless oil was used for the next step without purification.

Step 2 Preparation of Compound a98

To the dichloromethane (30 mL) solution of Compound a97 obtained in Step 1, pyridine (3.5 mL, 43.7 mmol), anhydrous acetic acid (3.4 mL, 36.4 mmol) and DMAP (1.78 g, 14.6 mmol) were added at room temperature, and the mixture was stirred for 1 hour. The reaction solution was concentrated under reduced pressure, and the resulted residue was purified by silica gel column chromatography (hexane-ethyl acetate) to afford Compound a98 (3.31 g, 91% yield) as a colorless oil.

Step 3 Preparation of Compound a99

To the dichloromethane (88 mL) solution of Compound a98 (3.31 g, 13.2 mmol) and allyltrimethylsilane (6.04 g, 52.8 mmol), boron trifluoride diethyl ether complex (2.00 mL, 15.9 mmol) was added dropwise at −78° C., and the mixture was stirred for 30 minutes at room temperature. Water was added to the reaction mixture, and the mixture was neutralized with sodium hydrogen carbonate. The mixture was extracted with ethyl acetate. The organic layer was washed with water, and the solvent was concentrated under reduced pressure. The obtained residue was purified by silica gel column chromatography (hexane-ethyl acetate) to afford Compound a99 (2.63 g, 86% yield) as a colorless oil.

$^1$H-NMR (CDCl$_3$) δ: 1.27-1.50 (2H, m), 1.75 (1H, ddd, J=13.0, 5.6, 3.3 Hz), 2.13-2.31 (3H, m), 3.18 (1H, t, J=10.4 Hz), 3.27-3.33 (1H, m), 3.42-3.49 (1H, m), 4.09 (1H, dq, J=10.8, 2.3 Hz), 4.56 (2H, q, J=11.8 Hz), 5.04-5.10 (2H, m), 5.76-5.86 (1H, m), 7.26-7.36 (5H, m).

Step 4 Preparation of Compound a100

To the acetone (17 mL)-water (3.8 mL)-acetic acid (0.8 mL) mixed solution of Compound a99 (486 mg, 2.09 mmol), the acetone (9.4 mL)-water (3.1 mL) mixed solution of potassium permanganate (537 mg, 3.40 mmol) was added at room temperature, and the mixture was stirred overnight. Ethanol (1 mL) was added to the reaction solution, and the insoluble matter was removed by celite filtration. The filtered solid was washed with ethyl acetate, and the filtrate was concentrated under reduced pressure. Toluene was added to the concentrated residue, and the solution was dehydrated by azeotropy. The concentrated residue was diluted with ethyl acetate, and the insoluble matter was filtrated. The filtrate was concentrated under reduced pressure to afford a mixture of Compound a100 and Compound a99 at the rate of 73 to 27. The obtained compound was used for the next reaction without further purification.

[M+H]=265.05, Method Condition 3: retention time 1.65 min

Step 5 Preparation of Compound a101

To the ethyl acetate (5.5 mL) solution of the mixture of Compound a100 and Compound a99 obtained in Step 4, triethylamine (0.406 mL, 2.93 mmol), anhydrous acetic acid (0.237 mL, 2.51 mmol) and DMAP (77.0 mg, 0.628 mmol) were added at room temperature, and the mixture was stirred at room temperature for 40 minutes. The reaction mixture was diluted with ethyl acetate, and the organic layer was washed with water. The organic layer was evaporated under reduced pressure, and the obtained residue was purified by silica gel column chromatography (hexane-ethyl acetate) to afford Compound a101 (298 mg, 47% yield) as a colorless oil.

$^1$H-NMR (CDCl$_3$) δ: 1.33-1.50 (2H, m), 1.79 (1H, dt, J=10.0, 2.7 Hz), 2.03-2.23 (4H, m), 2.44 (1H, dd, J=15.3, 4.6 Hz), 2.61 (1H, dd, J=15.3, 7.8 Hz), 3.18 (1H, t, J=10.5 Hz), 3.41-3.46 (1H, m), 3.69-3.73 (1H, m), 4.04 (1H, dq, J=10.9, 2.3 Hz), 4.49-4.75 (4H, m), 7.25-7.37 (5H, m).

Step 6 Preparation of Compound a102

To the dichloromethane (6 mL) of Compound a101 (296 mg, 0.966 mmol), N,N-diethylaminosulfur trifluoride (0.38 mL, 2.90 mmol) was added at 0° C., and the mixture was stirred at room temperature for 19 hours. N,N-diethylaminosulfur trifluoride (0.255 mL, 1.93 mmol) was added thereto, and the mixture was further stirred 24 hours. Ice was added to the reaction mixture, and the mixture was neutralized with sodium hydrogen carbonate. The mixture was extracted with ethyl acetate. The organic layer was concentrated under reduced pressure, and the obtained residue was purified by silica gel column chromatography (hexane-ethyl acetate) to afford Compound a102 (145 mg, 46% yield) as a colorless oil.

Additionally, Compound a101 (87.3 mg, recovery ratio: 30%) was recovered, and dissolved in dichloromethane (1.6 mL), and N,N-diethylaminosulfur trifluoride (0.188 mL, 1.43 mmol) was added thereto. The mixture was stirred for 65 hours. The reaction mixture was performed in the same procedure as the above treatment to afford Compound a102 (50.0 mg, 53% yield) as a colorless oil.

$^1$H-NMR (CDCl$_3$) δ: 1.38-1.54 (2H, m), 1.77 (1H, dd, J=12.8, 2.4 Hz), 1.93-2.24 (6H, m), 3.17 (1H, t, J=10.5 Hz), 3.39-3.57 (2H, m), 4.05 (1H, dq, J=10.9, 2.3 Hz), 4.22-4.38 (2H, m), 4.55 (2H, dd, J=22.3, 11.9 Hz), 7.23-7.39 (7H, m).

Step 7 Preparation of Compound a103

To the THF (4 mL) solution of Compound a102 (142 mg, 0.432 mmol), 1.00 mol/L diisobuthylaluminium hydride-hexane solution (0.95 ml, 0.95 mmol) was added dropwise at −78° C., and the mixture was stirred at room temperature for 20 minutes. Water (1 mL) was added to the reaction mixture. The organic layer was diluted with ethyl acetate, and the mixture was stirred at room temperature for 45 minutes. The precipitated white solid was removed by celite filtration, and the filtrate was evaporated under reduced pressure. Ethyl acetate was added to the concentrated residue, and the solution was dehydrated by azeotropy. The obtained colorless oil was used for the next step without further purification.

Also, to the THF (2 mL) solution of Compound a102 (50.0 mg, 0.152 mmol), 1.00 mol/L diisobuthylaluminium hydride-hexane solution (0.54 mL, 0.54 mmol) was added dropwise at −78° C., and the mixture was stirred at room temperature for 1 hour. Water (0.54 mL) was added to the reaction mixture. The organic layer was diluted with ethyl acetate, and the mixture was stirred at room temperature for 45 minutes. The precipitated white solid was removed by celite filtration, and then the filtrate was evaporated under reduced pressure. Ethyl acetate was added to the concentrated residue, and the solution was dehydrated by azeotropy. The obtained colorless oil was used for the next step without further purification.

Step 8 Preparation of Compound a104

To the dichloromethane (2.0 mL) solution of Compound a103 obtained in Step 7, Dess-Martin reagent (220 mg, 0.519 mmol) was added at room temperature, and the mixture was stirred for 22 hours.

Also, to the dichloromethane (2.0 mL) solution of the another compound a102 obtained in the above Step 9, Dess-Martin reagent (77.0 mg, 0.182 mmol) was added at room temperature, and the mixture was stirred for 17 hours. The combined two reaction solutions were concentrated, and the mixture was diluted with ethyl acetate. The solution was filtered by celite to remove the insoluble matter. The filtrate was concentrated, and the mixture was diluted with ethyl acetate (4 mL) and hexane (4 mL). The reaction solution was filtered by celite to remove the insoluble matter. The filtrate was evaporated under reduced pressure, and the resulted yellow oil was used for the next step without further purification.

Step 9 Preparation of Compound a105

To the dichloromethane (6 mL) solution of Compound a104 obtained in Step 8, anhydrous copper sulfate (420 mg, 2.63 mmol) and (S)-2-methylpropane-2-sulfinamide (106 mg, 0.877 mmol) were added, and the mixture was refluxed for 23 hours. The reaction mixture was cooled to room temperature, and the insoluble matter was removed by celite filtration. The filtrate was concentrated, and the resulted residue was purified by silica gel column chromatography (hexane-ethyl acetate) to afford Compound a105 (161 mg, 71% yield) as a colorless oil.

[M+H]=388.05, Method Condition 3: Retention time 2.49 min

Step 10 Preparation of Compound a106

To the dichloromethane (3 mL) solution of Compound a105 (159 mg, 0.411 mmol), 3 mol/L methylmagnesium bromide-diethylether solution (0.27 mL, 0.27 mmol) was added dropwise at −78° C., and the mixture was stirred for 1 hour. The reaction mixture was raised the temperature to −15° C., furthermore 3 mol/L methylmagnesium bromide-diethylether solution (0.27 mL, 0.27 mmol) was added dropwise thereto. The mixture was stirred at room temperature for 30 minutes. The reaction mixture was diluted with water, and 2 mol/L hydrochloric acid aqueous solution was added to adjust to pH5 of the reaction solution. The mixture was extracted with ethyl acetate. The organic layer was washed with water, and then the solvent was concentrated under reduced pressure. The obtained residue was purified by silica gel column chromatography (hexane-ethyl acetate) to afford Compound a106 (44.8 mg, 27% yield) as a yellow oil.

¹H-NMR (CDCl₃) δ: 1.20 (9H, s), 1.34 (3H, d, J=6.8 Hz), 1.37-1.55 (2H, m), 1.71-1.77 (1H, m), 1.88-2.03 (1H, m), 2.14-2.31 (2H, m), 3.21 (1H, t, J=10.5 Hz), 3.43-3.48 (1H, m), 3.59 (1H, dd, J=14.1, 5.2 Hz), 3.70 (1H, dd, J=15.3, 7.2 Hz), 4.02-4.20 (2H, m), 4.55 (2H, dd, J=25.0, 11.9 Hz), 7.27-7.39 (5H, m).

Step 11 Preparation of Compound a107

To the methanol (1 mL) solution of Compound a106 (43.2 mg, 0.107 mmol), 4 mol/L hydrochloric-dioxane solution (0.027 mL, 0.107 mmol) was added at room temperature, and the mixture was stirred for 20 minutes. The reaction solution was concentrated, and the precipitated white solid was used for the next step without further purification.

[M+H]=300.05, Method Condition 3: Retention time 1.35 min

Step 12 Preparation of Compound a108

To the THF (1 mL) solution of compound a107 obtained in Step 11, 2 mol/L sodium hydrate aqueous solution and anhydrous acetic acid (0.015 mL, 0.161 mmol) were added at room temperature, and the mixture was stirred for 30 minutes. The reaction solution was diluted with water, and extracted with ethyl acetate. The organic layer was washed with water, and the solvent was concentrated under reduced pressure. The obtained residue was purified by silica gel column chromatography (hexane-ethyl acetate) to afford Compound a108 (32.3 mg, 88% yield) as a colorless oil.

[M+H]=342.10, Method Condition 3: Retention time 1.94 min

Step 13 Preparation of Compound a109

To the methanol (4 mL) solution of Compound a108 (32.3 mg, 0.095 mmol), 20% palladium hydrate (wetted 50% with water, 24.8 mg, 0.018 mmol) was added at room temperature, the mixture was stirred under hydrogen atmosphere (1 atmosphere) for 6 hours. The hydrogen atmosphere into the reaction container was interchanged nitrogen atmosphere, and the reaction mixture was filtered by celite. The filtrate was concentrated under reduced pressure, and the obtained residue was purified by silica gel column chromatography (chloroform-methanol) to afford Compound a109 (22.2 mg, 93% yield) as a white solid.

[M+H]=130.05, Method Condition 3: Retention time=1.00 min

Step 14 Preparation of Compound a110

To the THF (2 mL) solution of Compound a22 (22.2 mg, 0.088 mmol) and Compound a109 (28.8 mg, 0.088 mmol), potassium tert-butoxide (20.8 mg, 0.186 mmol) was added at 0° C., and the mixture was stirred at room temperature for 1 hour. Ice was added to the reaction solution, and the mixture was extracted with ethyl acetate. The organic layer was washed with water, and concentrated under reduced pressure. The obtained residue was purified by silica gel column chromatography (chloroform-methanol) to afford Compound a110 (30.4 mg, 69% yield) as a white solid.

¹H-NMR (CDCl₃) δ: 1.23 (3H, d, J=6.8 Hz), 1.63-1.72 (2H, m), 1.87-2.10 (5H, m), 2.17-2.31 (1H, m), 2.47-2.51 (1H, m), 3.40 (1H, t, J=10.4 Hz), 3.70 (4H, d, J=8.5 Hz), 4.23 (2H, dt, J=3.9, 13.0 Hz), 4.29-4.35 (1H, m), 4.40-4.55 (1H, m), 5.11-5.21 (1H, m), 5.82 (1H, d, J=9.7 Hz), 6.09 (1H, tt, J=55.0, 4.1 Hz), 6.62 (1H, dd, J=10.6, 6.1 Hz).

Compound I-194 to I-252 were synthesized according to the same procedure as described above examples. The chemical formula and physical constants thereof were shown below.

TABLE 1

| Example No. | Structure | Method | Retention time (min) | [M + H] |
|---|---|---|---|---|
| I-194 | 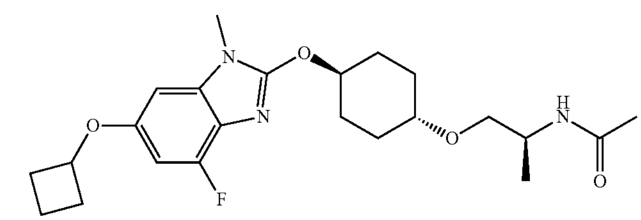 [SMILES: CC(=O)N[C@@H](C)CO[C@H]1CC[C@H](Oc2nc3c(F)cc(OC4CCC4)cc3n2C)CC1] | 2 | 2.14 | 434.25 |
| I-195 | 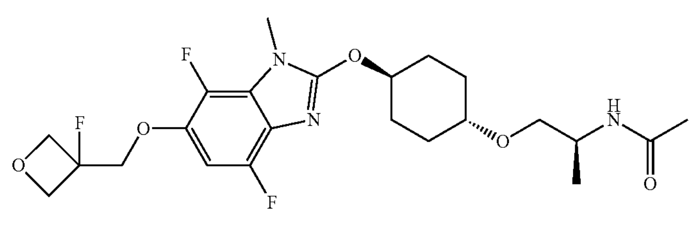 [SMILES: CC(=O)N[C@@H](C)CO[C@H]1CC[C@H](Oc2nc3c(F)cc(OCC4(F)COC4)c(F)c3n2C)CC1] | 3 | 1.92 | 486 |
| I-196 | 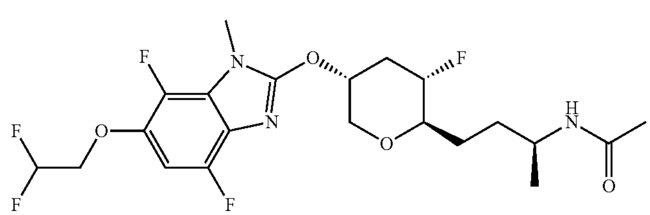 [SMILES: CC(=O)N[C@@H](C)CC[C@H]1OC[C@H](Oc2nc3c(F)cc(OCC(F)F)c(F)c3n2C)C[C@@H]1F] | 3 | 1.95 | 480.23 |

TABLE 2

| ID | Structure | | | |
|---|---|---|---|---|
| I-197 | (structure) | 3 | 1.6 | 403.05 |
| I-198 | (structure) | 2 | 1.82 | 421.25 |
| I-199 | (structure) | 3 | 1.54 | 403.15 |
| I-200 | (structure) | 3 | 2.14 | 436.05 |
| I-201 | (structure) | 2 | 2 | 438.25 |
| I-202 | (structure) | 3 | 1.78 | 416.1 |
| I-203 | (structure) | 3 | 1.94 | 468.05 |

TABLE 3

| ID | Structure | a | b | c |
|---|---|---|---|---|
| I-204 | 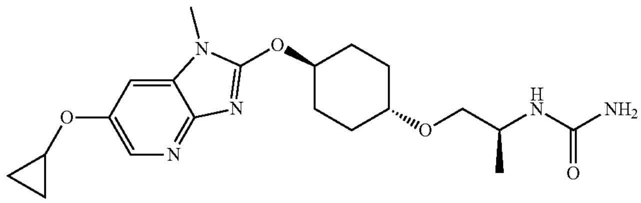 [SMILES: C[C@@H](CO[C@H]1CC[C@H](Oc2nc3ncc(OC4CC4)cc3n2C)CC1)NC(N)=O] | 3 | 1.47 | 404.1 |
| I-205 | 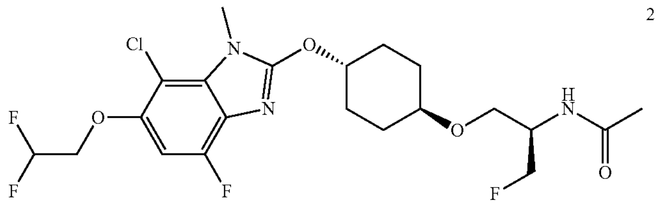 | 2 | 2.13 | 496.4 |
| I-206 | 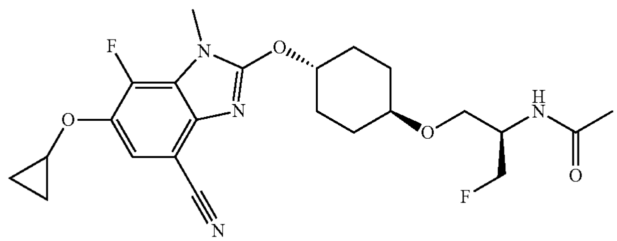 [SMILES: CC(=O)N[C@@H](CF)CO[C@H]1CC[C@H](Oc2nc3c(C#N)cc(OC4CC4)c(F)c3n2C)CC1] | 2 | 2.16 | 463.2 |
| I-207 | 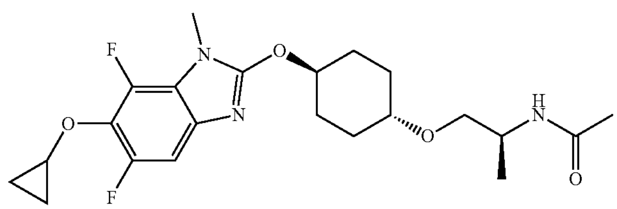 [SMILES: CC(=O)N[C@@H](C)CO[C@H]1CC[C@H](Oc2nc3cc(F)c(OC4CC4)c(F)c3n2C)CC1] | 3 | 2.18 | 438.05 |
| I-208 | 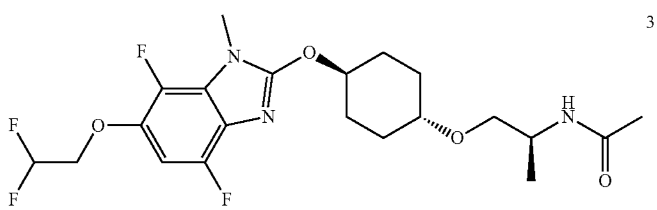 | 3 | 2.05 | 465.05 |
| I-209 | 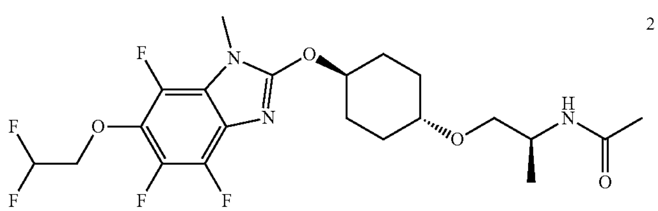 | 2 | 2.07 | 480.45 |
| I-210 | 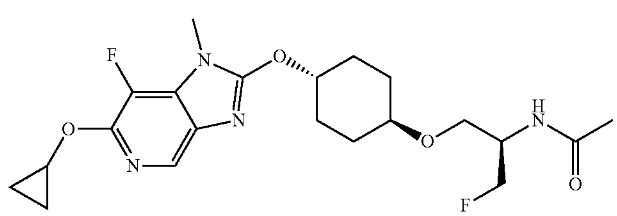 [SMILES: CC(=O)N[C@@H](CF)CO[C@H]1CC[C@H](Oc2nc3cnc(OC4CC4)c(F)c3n2C)CC1] | 2 | 1.85 | 439.25 |

TABLE 4

| ID | Structure | A | B | C |
|---|---|---|---|---|
| I-211 | 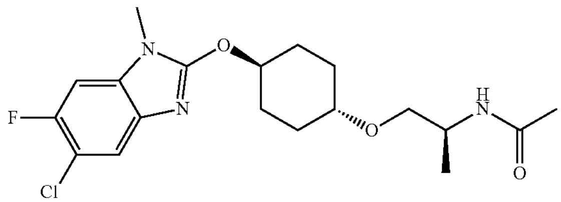 | 6 | 3.83 | 397.95 |
| I-212 | 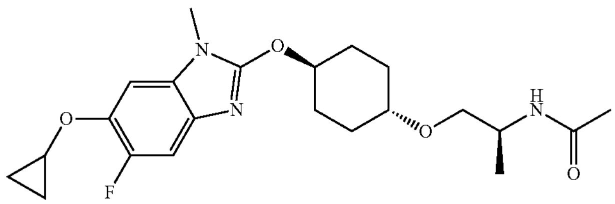 [SMILES: CC(=O)N[C@@H](C)CO[C@H]1CC[C@H](Oc2nc3cc(F)c(OC4CC4)cc3n2C)CC1] | 2 | 1.75 | 420.25 |
| I-213 | 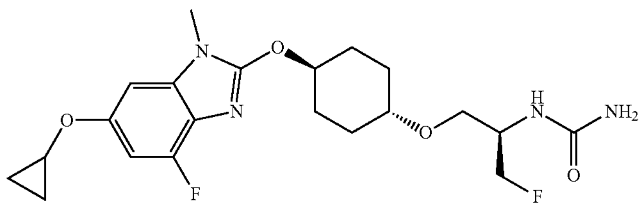 [SMILES: Cn1c(O[C@H]2CC[C@H](OC[C@H](CF)NC(N)=O)CC2)nc2c(F)cc(OC3CC3)cc21] | 3 | 1.96 | 439.15 |
| I-214 | 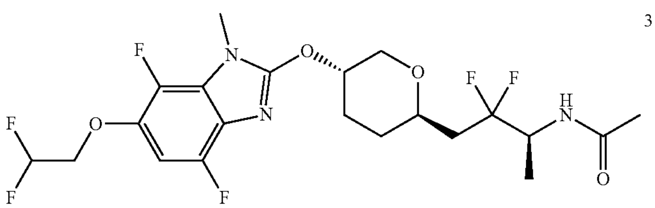 | 3 | 2.08 | 498.1 |
| I-215 | 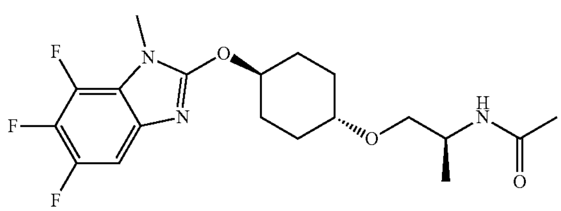 [SMILES: CC(=O)N[C@@H](C)CO[C@H]1CC[C@H](Oc2nc3cc(F)c(F)c(F)c3n2C)CC1] | 3 | 2.11 | 400.05 |
| I-216 | 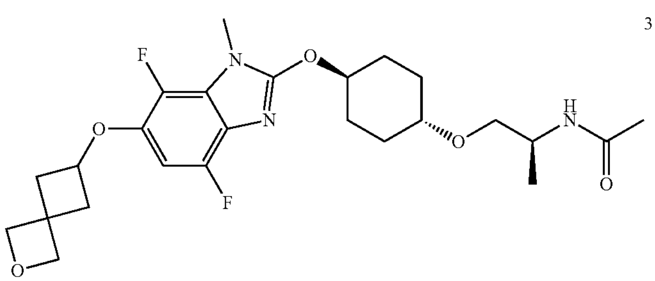 | 3 | 1.97 | 494.05 |
| I-217 | 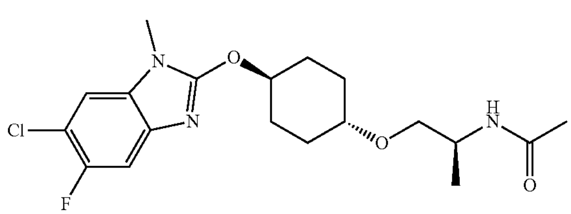 [SMILES: CC(=O)N[C@@H](C)CO[C@H]1CC[C@H](Oc2nc3cc(F)c(Cl)cc3n2C)CC1] | 6 | 3.89 | 398 |

TABLE 5

| ID | Structure | | | |
|---|---|---|---|---|
| I-218 | 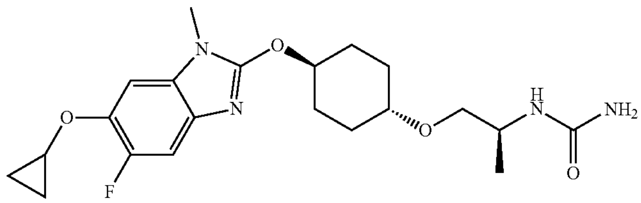 [SMILES: C[C@@H](CO[C@H]1CC[C@H](Oc2nc3cc(F)c(OC4CC4)cc3n2C)CC1)NC(N)=O] | 2 | 1.65 | 421.2 |
| I-219 | 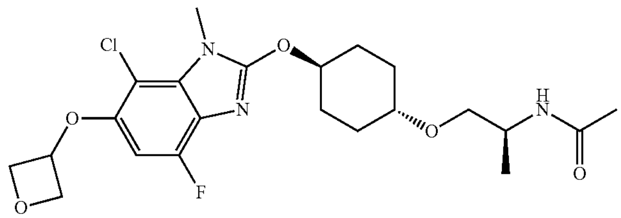 [SMILES: CC(=O)N[C@@H](C)CO[C@H]1CC[C@H](Oc2nc3c(F)cc(OC4COC4)c(Cl)c3n2C)CC1] | 3 | 1.96 | 470.1 |
| I-220 | 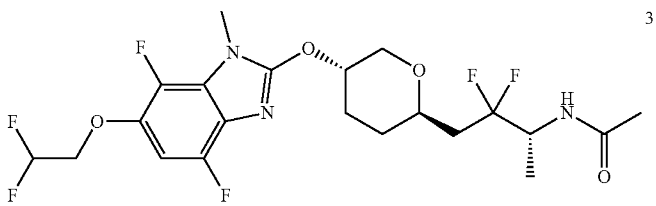 | 3 | 2.07 | 498.1 |
| I-221 | 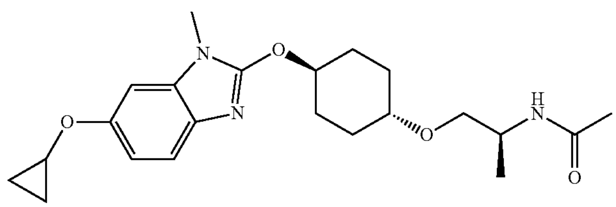 [SMILES: CC(=O)N[C@@H](C)CO[C@H]1CC[C@H](Oc2nc3ccc(OC4CC4)cc3n2C)CC1] | 3 | 1.67 | 402.25 |
| I-222 | 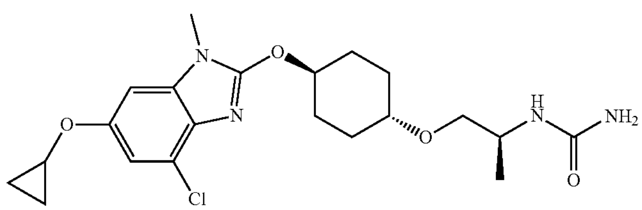 | 3 | 2.03 | 437 |
| I-223 | 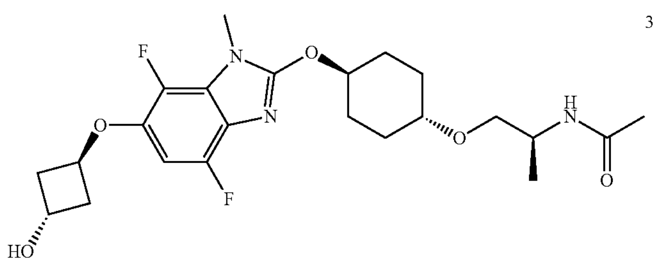 | 3 | 1.65 | 468.25 |
| I-224 | 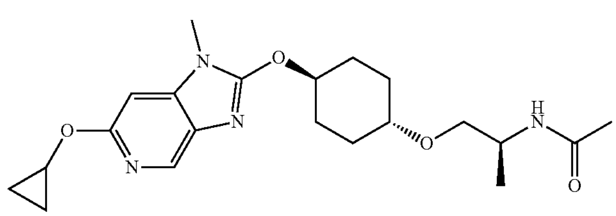 [SMILES: CC(=O)N[C@@H](C)CO[C@H]1CC[C@H](Oc2nc3cnc(OC4CC4)cc3n2C)CC1] | 2 | 1.11 | 403.65 |

TABLE 6
| | | | | | |
|---|---|---|---|---|---|
| I-225 | 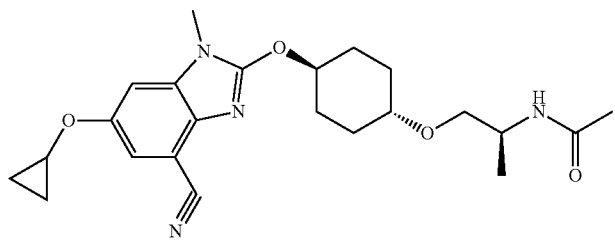 [SMILES: CC(=O)N[C@@H](C)CO[C@H]1CC[C@H](Oc2nc3c(C#N)cc(OC4CC4)cc3n2C)CC1] | | 3 | 2.07 | 427.1 |
| I-226 | 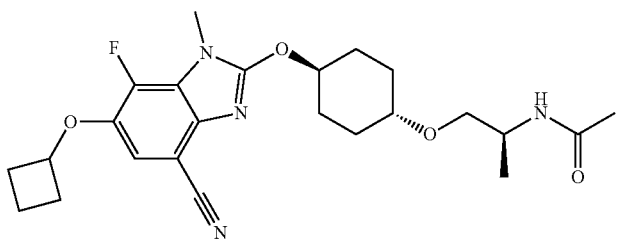 [SMILES: CC(=O)N[C@@H](C)CO[C@H]1CC[C@H](Oc2nc3c(C#N)cc(OC4CCC4)c(F)c3n2C)CC1] | | 2 | 2.31 | 459.25 |
| I-227 | 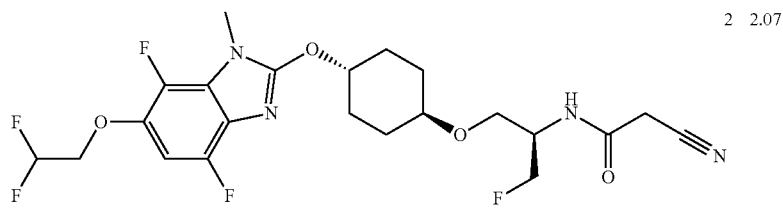 | | 2 | 2.07 | 505.2 |
| I-228 | 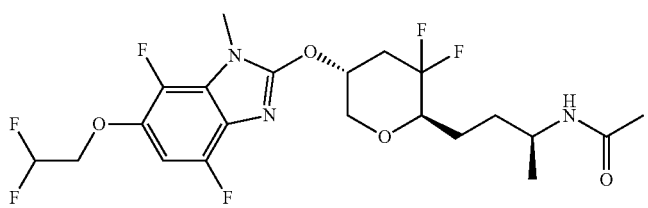 [SMILES: CC(=O)N[C@@H](C)CC[C@H]1OC[C@H](Oc2nc3c(F)cc(OCC(F)F)c(F)c3n2C)CC1(F)F] | | 3 | 2 | 498.31 |
| I-229 | 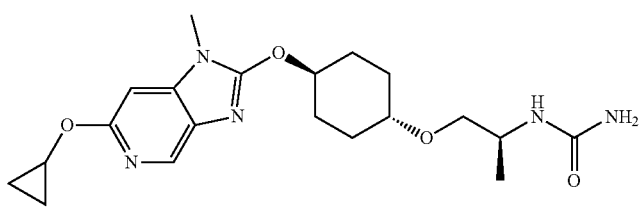 [SMILES: C[C@@H](CO[C@H]1CC[C@H](Oc2nc3cnc(OC4CC4)cc3n2C)CC1)NC(N)=O] | | 2 | 1.04 | 404.5 |
| I-230 | 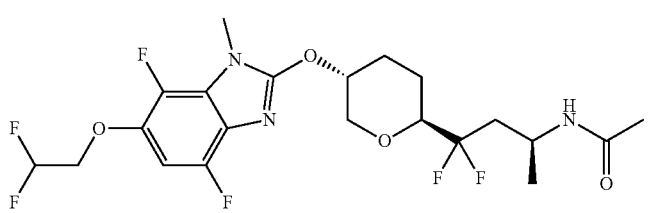 [SMILES: CC(=O)N[C@@H](C)CC(F)(F)[C@@H]1CC[C@@H](Oc2nc3c(F)cc(OCC(F)F)c(F)c3n2C)CO1] | | 3 | 2.06 | 498.05 |
| I-231 | 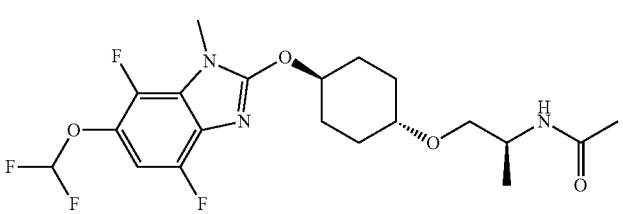 [SMILES: CC(=O)N[C@@H](C)CO[C@H]1CC[C@H](Oc2nc3c(F)cc(OC(F)F)c(F)c3n2C)CC1] | | 3 | 2.1 | 448.05 |

TABLE 7

| ID | Structure | a | b | c |
|---|---|---|---|---|
| I-232 | 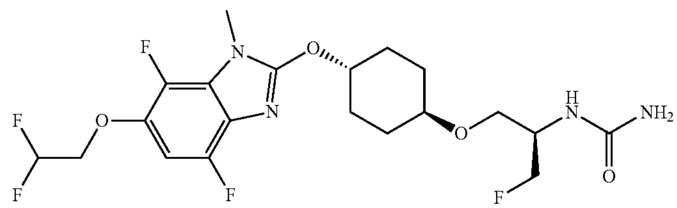 [SMILES: Cn1c(O[C@H]2CC[C@H](OC[C@H](CF)NC(N)=O)CC2)nc2c(F)cc(OCC(F)F)c(F)c21] | 2 | 1.89 | 481.45 |
| I-233 | 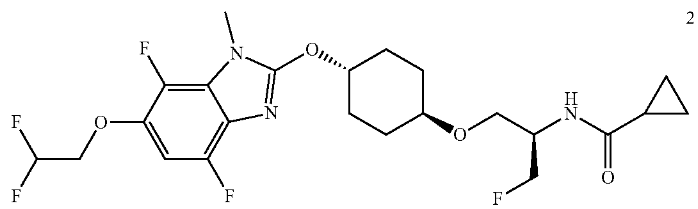 | 2 | 2.18 | 506.2 |
| I-234 | 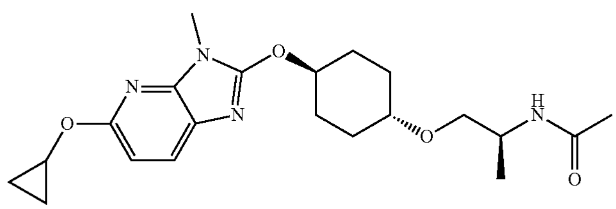 [SMILES: CC(=O)N[C@@H](C)CO[C@H]1CC[C@H](Oc2nc3ccc(OC4CC4)nc3n2C)CC1] | 2 | 1.77 | 403.6 |
| I-235 | 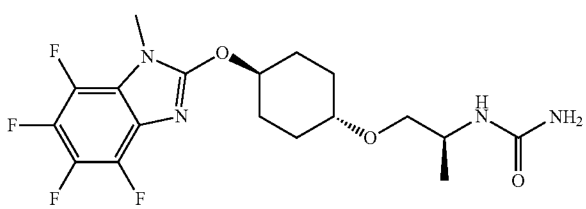 [SMILES: C[C@@H](CO[C@H]1CC[C@H](Oc2nc3c(F)c(F)c(F)c(F)c3n2C)CC1)NC(N)=O] | 2 | 2.02 | 419.4 |
| I-236 | 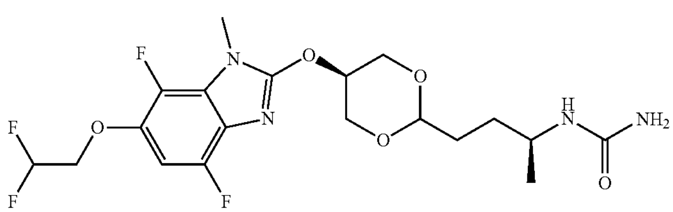 | 3 | 1.83 | 465.05 |
| I-237 | 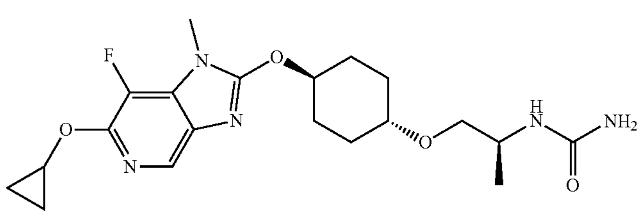 [SMILES: C[C@@H](CO[C@H]1CC[C@H](Oc2nc3cnc(OC4CC4)c(F)c3n2C)CC1)NC(N)=O] | 3 | 1.81 | 422.05 |
| I-238 | 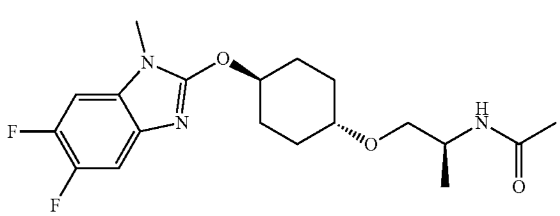 [SMILES: CC(=O)N[C@@H](C)CO[C@H]1CC[C@H](Oc2nc3cc(F)c(F)cc3n2C)CC1] | 2 | 1.8 | 382.2 |

TABLE 8

| ID | Structure | A | B | C |
|---|---|---|---|---|
| I-239 | 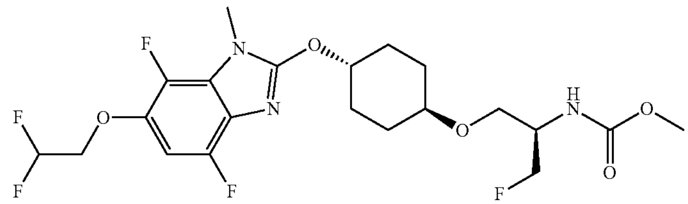 [SMILES: COC(=O)N[C@@H](CF)CO[C@H]1CC[C@H](Oc2nc3c(F)cc(OCC(F)F)c(F)c3n2C)CC1] | 2 | 2.21 | 496.4 |
| I-240 | 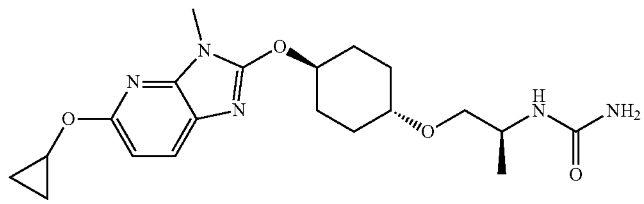 [SMILES: C[C@@H](CO[C@H]1CC[C@H](Oc2nc3ccc(OC4CC4)nc3n2C)CC1)NC(N)=O] | 2 | 1.66 | 404.6 |
| I-241 | 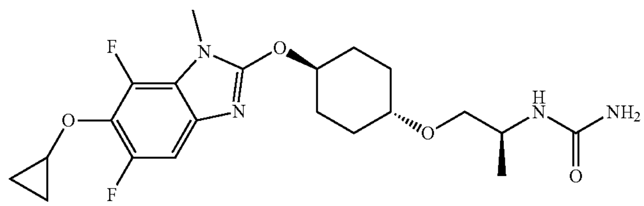 [SMILES: C[C@@H](CO[C@H]1CC[C@H](Oc2nc3cc(F)c(OC4CC4)c(F)c3n2C)CC1)NC(N)=O] | 3 | 2.07 | 439.05 |
| I-242 | 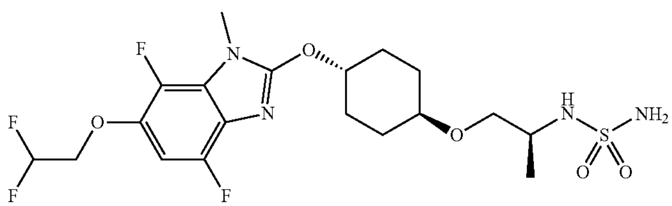 [SMILES: C[C@@H](CO[C@H]1CC[C@H](Oc2nc3c(F)cc(OCC(F)F)c(F)c3n2C)CC1)NS(N)(=O)=O] | 3 | 1.94 | 499.21 |
| I-243 | 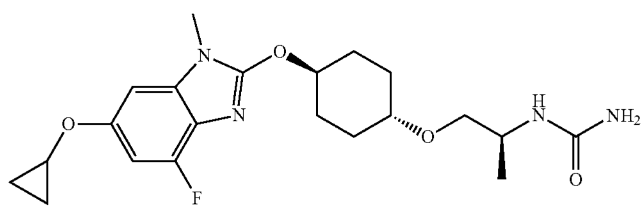 [SMILES: C[C@@H](CO[C@H]1CC[C@H](Oc2nc3c(F)cc(OC4CC4)cc3n2C)CC1)NC(N)=O] | 2 | 1.85 | 421.2 |
| I-244 | 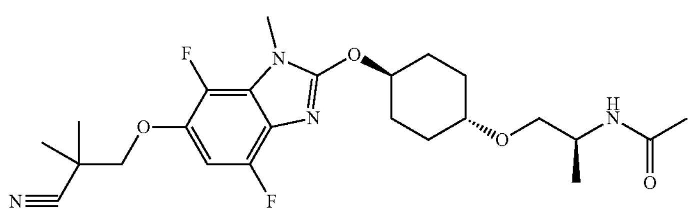 [SMILES: CC(=O)N[C@@H](C)CO[C@H]1CC[C@H](Oc2nc3c(F)cc(OCC(C)(C)C#N)c(F)c3n2C)CC1] | 6 | 4.04 | 479.1 |
| I-245 | 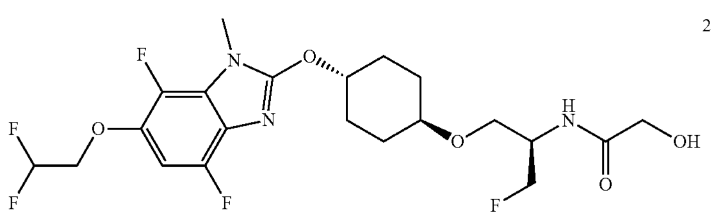 | 2 | 1.92 | 496.2 |

TABLE 9

| ID | Structure | a | b | c |
|---|---|---|---|---|
| I-246 | 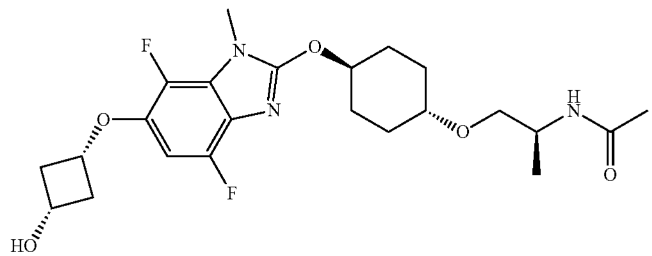 [SMILES: CC(=O)N[C@@H](C)CO[C@H]1CC[C@H](Oc2nc3c(F)cc(O[C@H]4C[C@@H](O)C4)c(F)c3n2C)CC1] | 3 | 1.71 | 468.1 |
| I-247 | 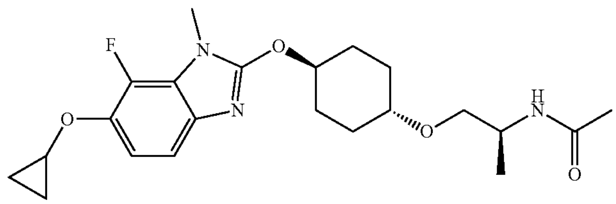 [SMILES: CC(=O)N[C@@H](C)CO[C@H]1CC[C@H](Oc2nc3ccc(OC4CC4)c(F)c3n2C)CC1] | 2 | 1.94 | 420.25 |
| I-248 | 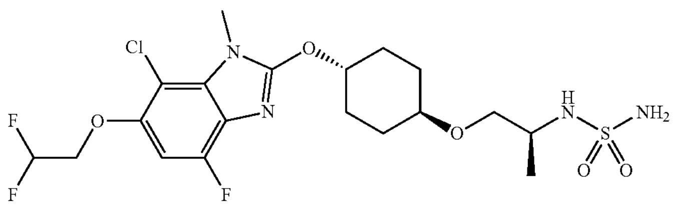 | 3 | 2.07 | 515.15 |
| I-249 | 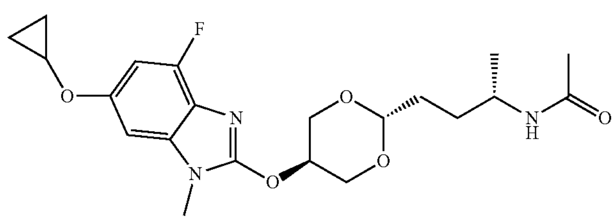 [SMILES: CC(=O)N[C@@H](C)CC[C@H]1OC[C@H](Oc2nc3c(F)cc(OC4CC4)cc3n2C)CO1] | 4 | 1.85 | 422.2 |
| I-250 | 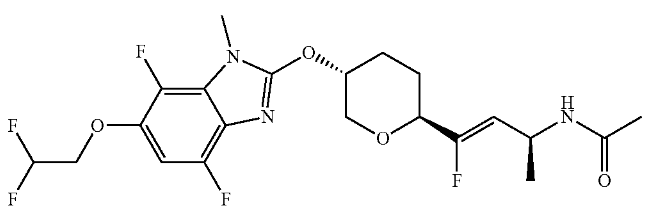 [SMILES: CC(=O)N[C@@H](C)/C=C(\F)[C@@H]1CC[C@@H](Oc2nc3c(F)cc(OCC(F)F)c(F)c3n2C)CO1] | 3 | 2.02 | 478.05 |
| I-251 | 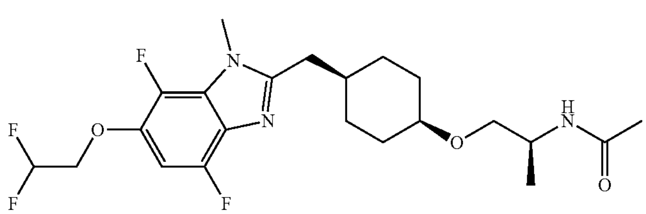 [SMILES: CC(=O)N[C@@H](C)CO[C@H]1CC[C@@H](Cc2nc3c(F)cc(OCC(F)F)c(F)c3n2C)CC1] | 2 | 1.74 | 460.25 |
| I-252 | 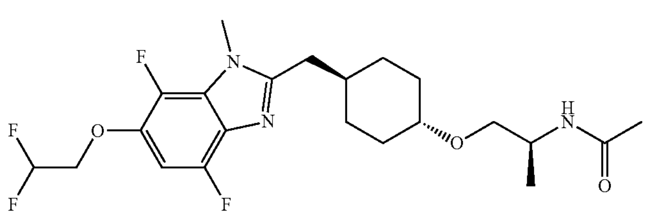 [SMILES: CC(=O)N[C@@H](C)CO[C@H]1CC[C@H](Cc2nc3c(F)cc(OCC(F)F)c(F)c3n2C)CC1] | 2 | 1.8 | 460.25 |

The Biological Test Examples of the present invention are described as follows.

Preparation Example 1: Preparation of Recombinant Human ACC2

After a cDNA encoding human ACC2 (27 amino acid residue to 2458 amino acid residues from the N-terminus) was cloned from human kidney cDNA library (Clontech), human ACC2 gene containing His-tag sequence at 5' terminus was inserted into pFastBac1 (Invitrogen). Recombinant baculovirus was generated using Bac-to-Bac baculovirus expression system (Invitrogen) according to the manufacturer's protocol. To express human ACC2, Sf-9 cells were infected with recombinant baculovirus. After infected cells were disrupted, the filtrated lysate was subjected to Ni-affinity chromatography and anion-exchange chromatography. The fractions containing human ACC2 protein were pooled as recombinant human ACC2 solution.

Preparation Example 2: Preparation of Recombinant Human ACC1

After a cDNA encoding human ACC1 (1 amino acid residue to 2346 amino acid residues from the N-terminus) was cloned from human liver cDNA library (BioChain), human ACC1 gene containing myc-tag and His-tag sequence at 3' terminus was inserted into pIEXBAC3 (Novagen). Recombinant baculovirus was generated using Flash-BACGOLD system (Oxford Expression Technologies) according to the manufacturer's protocol. To express human ACC1, Sf-9 cells were infected with recombinant baculovirus. After infected cells were disrupted, the filtrated lysate was subjected to Ni-affinity chromatography and anion-exchange chromatography. The fractions containing human ACC1 protein were pooled as recombinant human ACC1 solution.

Test Example 1: The Measurement of Inhibitory Activity on Human ACC1 and the ACC2

Recombinant human ACC1 and recombinant human ACC2, which were prepared by the method mentioned above, were preincubated with assay buffer solution (50 mM HEPES-KOH (pH 7.4), 10 mM magnesium chloride, 6-10 mM potassium citrate, 4 mM reduced form of glutathione, 1.5 mg/ml bovine serum albumin) for one hour. Then, 0.2 μL of each this invention compound solution (in DMSO) were dispensed to 384-well microplate, 5 μL of the preincubated enzyme solution and 5 μL of substrate solution (50 mM HEPES-KOH (pH 7.4), 1 mM ATP, 0.8 mM acetyl CoA and 25-50 mM potassium bicarbonate) were added to microplate. After centrifugation and shaking, the reaction mixtures were incubated in a humidified box at room temperature for 1 to 3 hours. After the incubation, the enzyme reactions were stopped by the addition of EDTA. Then, after the samples were cocrystallized with CHCA (α-cyano-4-hydroxy cinnamic acid) matrices on MALDI target plate, by using the matrix assist laser deionization time-of-flight mass spectrometer (MALDI-TOF MS), samples were measured in reflector negative mode. Deprotonated ions of acetyl CoA (AcCoA) of substrate and malonyl CoA (MalCoA) of the reaction product were detected, then, the conversion rates of acetyl CoA to malonyl CoA was calculated by the intensity of [MalCoA-H]−/(Intensity of [MalCoA-H].+Intensity of [AcCoA-H]—) using each signal strength. The 50% inhibitory concentration (IC50) was calculated from the inhibition rate of the enzymatic reaction at each concentration of the compounds. In addition, potassium citrate concentrations in assay buffer solution, potassium hydrogen carbonate concentrations in substrate solution and incubation time were adjusted by each lot of enzyme.

The 50% inhibitory concentration (IC50) on human ACC1 of Compound I-199, I-204, I-230, I-233, I-242, I-245, I-248, and I-252 were measured, the results of these compounds were more than 100 μM.

The inhibitory activity on human ACC2 of the each present compound is described in the following table.

TABLE 10

| Example No. | IC50(nM) |
|---|---|
| I-190 | 490 |
| I-191 | 350 |
| I-192 | 44 |
| I-193 | 4.9 |
| I-194 | 5.1 |
| I-195 | 35 |
| I-196 | 10 |
| I-197 | 13 |
| I-198 | 5.3 |
| I-199 | 730 |
| I-200 | 6.6 |
| I-201 | 4.7 |
| I-202 | 17 |
| I-203 | 110 |
| I-205 | 4.6 |
| I-206 | 12 |
| I-207 | 5.4 |
| I-208 | 8.7 |
| I-209 | 5.3 |
| I-210 | 7.2 |
| I-211 | 120 |
| I-212 | 55 |
| I-213 | 8.9 |
| I-214 | 12 |
| I-215 | 17 |
| I-216 | 57 |
| I-217 | 64 |
| I-218 | 120 |
| I-219 | 12 |
| I-220 | 180 |
| I-221 | 9.1 |
| I-222 | 17 |
| I-223 | 87 |
| I-224 | 150 |
| I-225 | 33 |
| I-226 | 6.1 |
| I-227 | 44 |
| I-228 | 13 |
| I-229 | 600 |
| I-230 | 89 |
| I-231 | 10 |
| I-232 | 11 |
| I-233 | 31 |
| I-234 | 13 |
| I-235 | 43 |
| I-236 | 9.6 |
| I-237 | 12 |
| I-238 | 83 |
| I-239 | 30 |
| I-240 | 44 |
| I-241 | 9.5 |
| I-242 | 120 |
| I-243 | 5.6 |
| I-244 | 26 |
| I-245 | 53 |
| I-246 | 78 |
| I-247 | 3.9 |
| I-248 | 160 |
| I-249 | 6.6 |
| I-250 | 21 |
| I-251 | 100 |

Test Example 2: CYP Inhibition Test

Using commercially available human hepatic microsome, and employing, as markers, 7-ethoxyresorufin O-deethylation (CYP1A2), tolbutamide methyl-hydroxylation (CYP2C9), mephenytoin 4'-hydroxylation (CYP2C19), dextromethorphan O-demethylation (CYP2D6), and terfenedine hydroxylation (CYP3A4) astypical substrate metabolism reactions of human main five CYP enzyme forms (CYP1A2, 2C9, 2C19, 2D6, 3A4), an inhibitory degree of each metabolite production amount by a test compound was assessed.

The reaction conditions were as follows: substrate, 0.5 μmol/L ethoxyresorufin (CYP1A2), 100 μmol/L tolbutamide (CYP2C9), 50 μmol/L S-mephenitoin (CYP2C19), 5 μmol/L dextromethorphan (CYP2D6), 1 μmol/L terfenedine (CYP3A4); reaction time, 15 minutes; reaction temperature, 37° C.; enzyme, pooled human hepatic microsome 0.2 mg protein/mL; test drug concentration, 1, 5, 10, 20 μmol/L (four points).

Each five kinds of substrates, human hepatic microsome, or a test drug in 50 mM Hepes buffer as a reaction solution was added to a 96-well plate at the composition as described above, NADPH, as a cofactor was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the supernatant was quantified by a fluorescent multilabel counter and tributamide hydroxide (CYP2CP metabolite), mephenytoin 4' hydroxide (CYP2C19 metabolite), dextromethorphan (CYP2D6 metabolite), and terfenadine alcohol (CYP3A4 metabolite) are quantified by LC/MS/MS.

Addition of only DMSO being a solvent dissolving a drug to a reaction system was adopted as a control (100%), remaining activity (%) was calculated at each concentration of a test drug added as the solution and IC50 was calculated by reverse presumption by a logistic model using a concentration and an inhibition rate.

Test Example 3: BA Test

An experimental material and a method for examining oral absorbability
(1) Animals used: SD rats or mice were used
(2) Breeding condition: chow and sterilized tap water were allowed to be taken in freely.
(3) Setting of a dosage and grouping: a predetermined dosage was administered orally or intravenously. Groups were formed as shown below. (A dosage varied depending on each compound)
Oral administration 1-30 mg/kg (n=2 to 3)
Intravenous administration 0.5-10 mg/kg (n=2 to 3)
(4) Preparation of administered liquid: In oral administration, a solution or suspension was administered. In intravenous administration, after solubilization, the administration was performed.
(5) Method of Administration: In oral administration, compulsory administration to the stomach was conducted using an oral probe.
In intravenous administration, administration from the caudal vein was conducted using a syringe with an injection needle.
(6) Evaluation item: Blood was chronologically collected, and then the plasma concentration of a compound of the present invention in was measured using a LC/MS/MS.
(7) Statistical analysis: With regard to a shift in plasma concentration, the plasma concentration-time area under the curve (AUC) was calculated using a nonlinear least-squares program WinNonlin®. Bioavailability (BA) was calculated from the AUCs of the oral administration group and the intravenous administration group, respectively.

Test Example 4: Metabolism Stability Test

Using commercially available pooled human hepatic microsomes, a test compound was reacted for a constant time, a remaining rate was calculated by comparing a reacted sample and an unreacted sample, thereby, a degree of metabolism in liver was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 μL of the reaction solution was added to 100 μL of a methanol/acetonitrile=1/1 (v/v), mixed and centrifuged at 3000 rpm for 15 minutes. The test compound in the supernatant was quantified by LC/MS/MS, and a remaining amount of the test compound after the reaction was calculated, letting a compound amount at 0 minute reaction time to be 100%. Hydrolysis reaction was performed in the absence of NADPH and glucuronidation reaction was in the presence of 5 mM UDP-glucuronic acid in place of NADPH, followed by similar operations.

Test Example 5: CYP3A4 Fluorescent MBI Test

The CYP3A4 fluorescent MBI test is a test of investigating enhancement of CYP3A4 inhibition of a compound by a metabolism reaction, and the test was performed using, a reaction in which 7-benzyloxytrifluoromethylcoumarin (7-BFC) was debenzylated by the CYP3A4 enzyme to produce a metabolite, 7-hydroxytrifluoromethylcoumarin (7-HFC) emitting fluorescent light.

The reaction conditions were as follows: substrate, 5.6 μmol/L 7-BFC; pre-reaction time, 0 or 30 minutes; reaction time, 15 minutes; reaction temperature, 25° C. (room temperature); CYP3A4 content (expressed in *Escherichia coli*), at pre-reaction 62.5 μmol/mL, at reaction 6.25 μmol/mL (at 10-fold dilution); test drug concentration, 0.625, 1.25, 2.5, 5, 10, 20 μmol/L (six points).

An enzyme in a K-Pi buffer (pH 7.4) and a test drug solution as a pre-reaction solution were added to a 96-well plate at the composition of the pre-reaction, a part of it was transferred to another 96-well plate so that it was 1/10 diluted by a substrate in a K-Pi buffer, NADPH as a co-factor was added to initiate a reaction as an index (without preincubation) and, after a predetermined time of a reaction, acetonitrile/0.5 mol/L Tris (trishydroxyaminomethane)=4/1 (v/v) was added to stop the reaction. In addition, NADPH was added to a remaining preincubation solution to initiate a preincubation (with preincubation) and, after a predetermined time of a preincubation, a part was transferred to another plate so that it was 1/10 diluted with a substrate and a K-Pi buffer to initiate a reaction as an index. After a predetermined time of a reaction, acetonitrile/0.5 mol/L Tris (trishydroxyaminomethane)=4/1 (v/v) was added to stop the reaction. For the plate on which each index reaction had been performed, a fluorescent value of 7-HFC which is a metabolite was measured with a fluorescent plate reader. (Ex=420 nm, Em=535 nm).

Addition of only DMSO which was a solvent dissolving a drug to a reaction system was adopted as a control (100%), remaining activity (%) was calculated at each concentration of a test drug added as the solution, and IC50 was calculated by reverse-presumption by a logistic model using a concentration and an inhibition rate. When a difference between IC50 values was 5 µmol/L or more, this was defined as (+) and, when the difference was 3 µmol/L or less, this was defined as (−).

Test Example 6: Fluctuation Ames Test

The compounds of the present invention are assessed for mutagenic property.

20 µL of freezing-stored rat typhoid *bacillus* (*Salmonella typhimurium* TA98 strain, TA100 strain) is inoculated on 10 mL of a liquid nutrient medium (2.5% Oxoid nutrient broth No. 2), and this is cultured before shaking at 37° C. for 10 hours. 9 mL of a bacterial solution of the TA98 strain is centrifuged (2000×g, 10 minutes) to remove a culturing solution, the bacteria is suspended in 9 mL of a Micro F buffer ($K_2HPO_4$: 3.5 g/L, $KH_2PO_4$: 1 g/L, $(NH_4)_2SO_4$: 1 g/L, trisodium citrate dehydrate: 0.25 g/L, $MgSO_4.7H_2O$: 0.1 g/L), the suspension is added to 110 mL of an Exposure medium (Micro F buffer containing Biotin: 8 µg/mL, histidine: 0.2 µg/mL, glucose: 8 mg/mL), and the TA100 strain is added to 120 mL of the Exposure medium relative to 3.16 mL of the bacterial solution to prepare a test bacterial solution. Each 12 µL of a test substance DMSO solution (8 stage dilution from maximum dose 50 mg/mL at 2 to 3 fold ratio), DMSO as a negative control, 50 µg/mL of 4-nitroquinoline-1-oxide DMSO solution for the TA98 strain, 0.25 µg/mL of 2-(2-furyl)-3-(5-nitro-2-furyl)acrylamide DMSO solution for the TA100 strain under the non-metabolism activating condition, 40 µg/mL of 2-aminoanthracene DMSO solution for the TA98 strain, 20 µg/mL of 2-aminoanthracene DMSO solution for the TA100 strain under the metabolism activating condition as a positive control, and 588 µL of the test bacterial solution (a mixed solution of 498 µl of the test bacterial solution and 90 µL of S9 mix under the metabolism activating condition) are mixed, and this is shaking-cultured at 37° C. for 90 minutes. 460 µL of the bacterial solution exposed to the test substance is mixed with 2300 µL of an Indicator medium (Micro F buffer containing biotin: 8 µg/mL, histidine: 0.2 µg/mL, glucose: 8 mg/mL, Bromo Cresol Purple: 37.5 µg/mL), each 50 µL is dispensed into microplate 48 wells/dose, and this is subjected to stationary culturing at 37° C. for 3 days. Since a well containing a bacterium which has obtained the proliferation ability by mutation of an amino acid (histidine) synthesizing enzyme gene turns from purple to yellow due to a pH change, the bacterium proliferation well which has turned to yellow in 48 wells per dose is counted, and is assessed by comparing with a negative control group. (−) means that mutagenicity is negative and (+) is positive.

Test Example 7: hERG Test

For the purpose of assessing risk of an electrocardiogram QT interval prolongation, effects on delayed rectifier K+ current (IKr), which plays an important role in the ventricular repolarization process of the compound of the present invention, was studied using HEK293 cells expressing human ether-a-go-go related gene (hERG) channel.

After a cell was retained at a membrane potential of −80 mV by whole cell patch clamp method using an automated patch clamp system (PatchXpress 7000A, Axon Instruments Inc.), IKr induced by depolarization pulse stimulation at +40 mV for 2 seconds and, further, repolarization pulse stimulation at −50 mV for 2 seconds is recorded. After the generated current was stabilized, extracellular solution (NaCl: 135 mmol/L, KCl: 5.4 mmol/L, $NaH_2PO_4$: 0.3 mmol/L, $CaCl_2.2H_2O$: 1.8 mmol/L, $MgCl_2.6H_2O$: 1 mmol/L, glucose: 10 mmol/L, HEPES (4-(2-hydroxyethyl)-1-piperazineethanesulfonic acid): 10 mmol/L, pH=7.4) in which the test compound has been dissolved at an objective concentration is applied to the cell under the room temperature condition for 10 minutes. From the recording IKr, an absolute value of the tail peak current was measured based on the current value at the resting membrane potential using an analysis software (DataXpress ver.1, Molecular Devices Corporation). Further, the % inhibition relative to the tail peak current before application of the test substance was calculated, and compared with the vehicle-applied group (0.1% dimethyl sulfoxide solution) to assess influence of the test substance on IKr.

Test Example 8: Solubility Test

The solubility of the compounds of the present invention were determined in 1% DMSO addition condition. The 10 mmol/L compound solution was prepared in DMSO, To the pH6.8 artificial intestinal fluid (To 0.2 mol/L potassium dihydrogen phosphate reagent 250 mL and 0.2 mol/L NaOH reagent solution 118 mL, water was added until it become 1000 mL solution) 594 µL, the compound of the present invention solution 6 µL was added. After stood at 25° C. for 16 hours, the mixture was filtered while suctioning. The filtrate was diluted two-fold with methanol/water=1/1 (V/V), and its concentration into the filtrate was measured by the absolute calibration curve method using HPLC or LC/MS/MS.

Test Example 9: Powder Solubility Test

Appropriate amounts of the test substances were put into appropriate containers. To the respective containers were added 200 µL of JP-1 fluid (sodium chloride 2.0 g, hydrochloric acid 7.0 mL and water to reach 1000 mL), 200 µL of JP-2 fluid (phosphate buffer (pH6.8) 500 mL and water 500 mL), and 200 µL of 20 mmol/L TCA (sodium taurocholate)/JP-2 fluid (TCA 1.08 g and JP-2 fluid to reach 100 mL). In the case that the test compound was dissolved after the addition of the test fluid, the bulk powder was added as appropriate. The containers were sealed, and shaken for 1 hour at 37° C. The mixtures are filtered, and 100 µL of methanol was added to each of the filtrate (100 µL) so that the filtrates were two-fold diluted. The dilution ratio was changed if necessary. The dilutions were observed for bubbles and precipitates, and then the containers were sealed and shaken. Quantification was performed by HPLC with an absolute calibration method.

Formulation Example

The following Formulation Examples are only exemplified and not intended to limit the scope of this invention.

Formulation Example 1: Tablets

| | |
|---|---|
| The compound of the present invention | 15 mg |
| Lactose | 15 mg |
| Calcium stearate | 3 mg |

The components other than calcium stearate are homogeneously mixed and dried by crushing granulation, and appropriate size granules. Then the tablets are compression-molded by the addition of calcium stearate.

Formulation Example 2: Capsules

| The compound of the present invention | 10 mg |
| Magnesium sterate | 10 mg |
| Lactose | 80 mg |

They are uniformly mixed to produce a powder medicine as a powder or fine granules. The capsule are made by filling them into a capsule container Formulation Example 3: Granules

| The compound of the present invention | 30 g |
| Lactose | 265 g |
| Magnesium stearate | 5 g |

After the above ingredients are mixed uniformly, the mixture is compressed, crushed, granulated and sieved to obtain a suitable size of granules.

INDUSTRIAL APPLICABILITY

The compounds of this invention have an ACC2 inhibitory activity, and are very useful for treatment or prevention of a disease associated with ACC2.

The invention claimed is:
1. A compound of Formula (I):

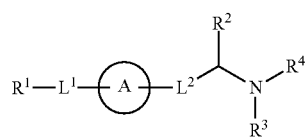

(I)

or its pharmaceutically acceptable salt,
wherein
R$^1$ is substituted or unsubstituted benzimidazol;
ring A is substituted or unsubstituted non-aromatic heterocycle;
—L$^1$— is —O—(CR$^6$R$^7$)m—, wherein the bond of left side is attached to R$^1$, and the bond of right side is attached to ring A;
—L$^2$— is (CR$^6$R$^7$)n—, wherein the bond of left side is attached to ring A, and the bond of right side is attached to the group represented by Formula:

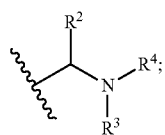

each R$^6$ is independently hydrogen, halogen, cyano, substituted or unsubstituted alkyl, substituted or unsubstituted alkenyl or substituted or unsubstituted alkynyl;

each R$^7$ is independently hydrogen, halogen, cyano, substituted or unsubstituted alkyl, substituted or unsubstituted alkenyl or substituted or unsubstituted alkynyl;
R$^6$ and R$^7$ on the same carbon atom may be taken together with the carbon atom to form ring;
each m is independently an integer of 0, 1, 2 or 3;
each n is independently an integer of 1, 2 or 3;
R$^2$ is substituted or unsubstituted alkyl;
R$^3$ is hydrogen, or substituted or unsubstituted alkyl;
R$^4$ is substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl, substituted or unsubstituted aromatic heterocyclylsulfonyl or substituted or unsubstituted sulfamoyl.

2. The compound or its pharmaceutically acceptable salt according to claim 1, wherein R$^1$ is the group represented by Formula:

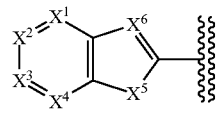

wherein
X$^1$ is C(R$^{x1}$);
X$^2$ is C(R$^{x2}$);
X$^3$ is C(R$^{x3}$);
X$^4$ is C(R$^{x4}$);
X$^5$ is N(R$^{x5}$);
X$^6$ is N;
each R$^{x1}$, R$^{x2}$, R$^{x3}$, R$^{x4}$, and R$^{x5}$ is independently hydrogen, halogen, hydroxy, carboxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted amino, substituted or unsubstituted carbamoyl, substituted or unsubstituted sulfamoyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted alkylsulfonyl, substituted or unsubstituted alkenylsulfonyl, substituted or unsubstituted alkynylsulfonyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted non-aromatic carbocyclylsulfonyl, substituted or unsubstituted aromatic carbocyclylsulfonyl, substituted or unsubstituted non-aromatic heterocyclylsulfonyl, substituted or unsubstituted aromatic heterocyclylsulfonyl, substituted or unsubstituted non-aromatic carbocyclyloxy, substituted or unsubstituted aromatic carbocyclyloxy, substituted or unsubstituted non-aromatic heterocyclyloxy, or substituted or unsubstituted aromatic heterocyclyloxy.

3. The compound or its pharmaceutically acceptable salt according to claim 2, wherein $R^1$ is the group represented by Formula:

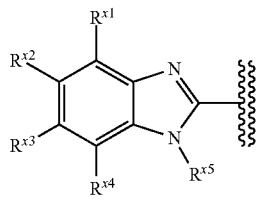

wherein $R^{x1}$, $R^{x2}$, $R^{x3}$, $R^{x4}$ and $R^{x5}$ are the same as in claim 2.

4. The compound or its pharmaceutically acceptable salt according to claim 3, wherein $R^{x1}$ is hydrogen, halogen or cyano; $R^{x2}$ is hydrogen, halogen or cyano; $R^{x3}$ is substituted or unsubstituted alkyloxy, substituted or unsubstituted non-aromatic carbocyclyloxy, substituted or unsubstituted aromatic carbocyclyloxy, substituted or unsubstituted non-aromatic heterocyclyloxy or substituted or unsubstituted aromatic heterocyclyloxy; $R^{x4}$ is hydrogen, halogen or cyano, and $R^{x5}$ is substituted or unsubstituted alkyl.

5. The compound or its pharmaceutically acceptable salt according to claim 1, wherein the group represented by the formula —$L^1$— ring A—$L^2$— is a group selected from the group consisting of:

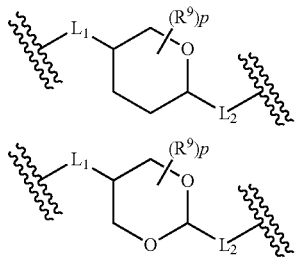

and
wherein
$R^9$ is halogen, cyano, hydroxy, carboxy, oxo, substituted or unsubstituted alkyl, substituted or unsubstituted alkyloxy or substituted or unsubstituted amino;
p is an integer of 0 to 4; and
—$L^1$— and —$L^2$— are as defined in claim 1.

6. The compound or its pharmaceutically acceptable salt according to claim 1, wherein m is 0.

7. The compound or its pharmaceutically acceptable salt according to claim 1, wherein n is 2.

8. The compound or its pharmaceutically acceptable salt according to claim 1, wherein $R^4$ is substituted or unsubstituted alkylcarbonyl, substituted or unsubstituted alkenylcarbonyl, substituted or unsubstituted alkyloxycarbonyl, substituted or unsubstituted carbamoyl, substituted or unsubstituted alkylsulfonyl or substituted or unsubstituted sulfamoyl.

9. The compound or its pharmaceutically acceptable salt according to claim 8, wherein $R^4$ is substituted or unsubstituted alkylcarbonyl.

10. The compound or its pharmaceutically acceptable salt according to claim 1, wherein Formula (I) is Formula (I'):

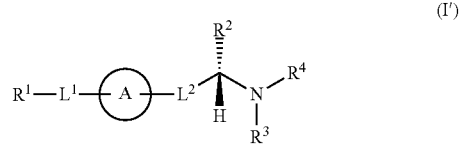

wherein $R^1$, $L^1$, ring A, $L^2$, $R^2$, $R^3$ and $R^4$ are as defined in claim 1.

11. The compound or its pharmaceutically acceptable salt according to claim 1, wherein Formula (I) is Formula (I"):

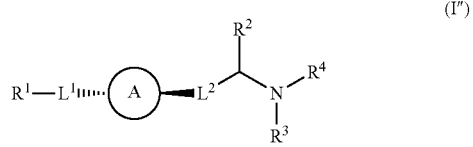

wherein $R^1$, $L^1$, ring A, $L^2$, $R^2$, $R^3$ and $R^4$ are as defined in claim 1.

12. A compound of Formula (I):

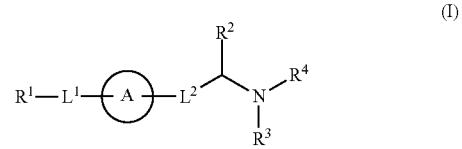

or its pharmaceutically acceptable salt,
wherein
$R^1$ is a group represented by the formula:

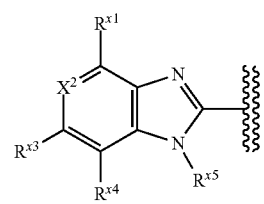

wherein $X^2$ is C(H),
$R^{x1}$ is halogen,
$R^{x3}$ is non-aromatic carbocyclyloxy,
$R^{x4}$ is hydrogen,
$R^{x5}$ is alkyl,
ring A is a group represented by the formula:

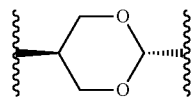

—$L^1$— is —O—,
—$L^2$— is —(CH$_2$)$_2$—, wherein, the left bond binds to ring A, and the right bond binds to a group represented by the formula:

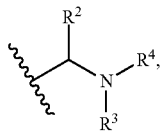

$R^2$ is alkyl or haloalkyl,
$R^3$ is hydrogen,
$R^4$ is alkylcarbonyl or carbamoyl.

13. A compound or its pharmaceutically acceptable salt selected from the group consisting of

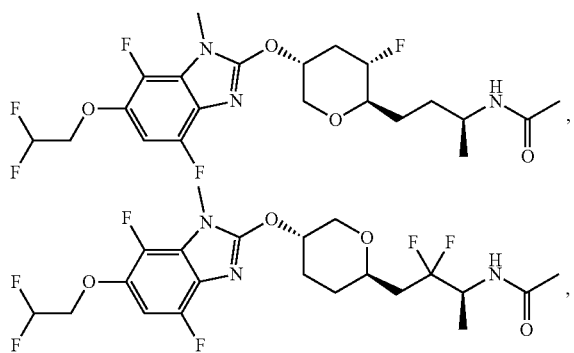

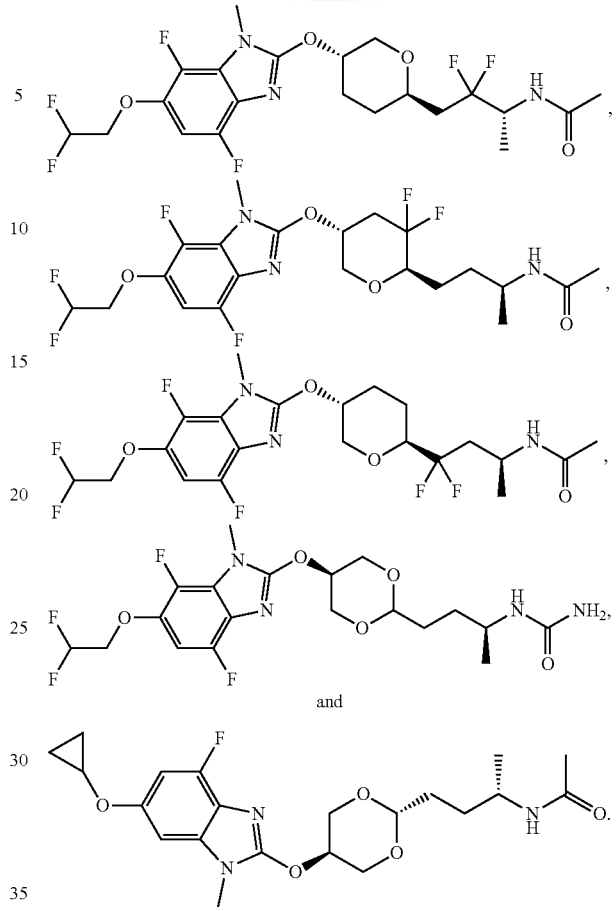

and

14. A pharmaceutical composition which comprises the compound or its pharmaceutical acceptable salt according to claim 1 and a pharmaceutically acceptable additive.

15. A method for treatment of obesity, diabetes, insulin resistance, abnormal glucose tolerance, diabetic peripheral neuropathy, diabetic nephropathy, diabetic retinal disease, or diabetic macroangiopathy, comprising administering an effective amount of the compound or its pharmaceutical acceptable salt according to claim 1 to a subject in need thereof.

* * * * *